(12) United States Patent
Culbert et al.

(10) Patent No.: US 10,293,147 B2
(45) Date of Patent: May 21, 2019

(54) TELESCOPIC PERCUTANEOUS TISSUE DILATION SYSTEMS AND RELATED METHODS

(71) Applicant: DePuy Synthes Products, Inc., Raynham, MA (US)

(72) Inventors: Brad Culbert, Rancho Santa Margarita, CA (US); Mark C. Boomer, Irvine, CA (US); Christopher Warren, Aliso Viejo, CA (US); Fausto Olmos, Laguna Niguel, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/186,963

(22) Filed: Jun. 20, 2016

(65) Prior Publication Data
US 2017/0143945 A1 May 25, 2017

Related U.S. Application Data

(63) Continuation of application No. 11/659,025, filed as application No. PCT/US2005/027431 on Aug. 2, (Continued)

(51) Int. Cl.
*A61M 29/00* (2006.01)
*A61M 25/00* (2006.01)
(Continued)

(52) U.S. Cl.
CPC ......... *A61M 29/00* (2013.01); *A61B 1/00016* (2013.01); *A61B 1/00071* (2013.01);
(Continued)

(58) Field of Classification Search
CPC .................................................... A61M 29/00
See application file for complete search history.

(56) References Cited

U.S. PATENT DOCUMENTS

| 3,486,505 A | 12/1969 | Morrison |
| 3,698,391 A | 10/1972 | Mahony |

(Continued)

FOREIGN PATENT DOCUMENTS

| EP | 0433717 A1 | 6/1991 |
| JP | 07-502419 A | 3/1995 |

(Continued)

OTHER PUBLICATIONS

Mar. 14, 2012 Supplemental European Search Report for Application No. EP5777628.

(Continued)

*Primary Examiner* — Richard G Louis
(74) *Attorney, Agent, or Firm* — BakerHostetler

(57) ABSTRACT

Tissue dilation systems are disclosed. The present systems provide percutaneous access to one or more target structures located in a patient's body. The tissue dilation systems include two or more tissue dilation tubes telescopically arranged and moveable relative to each other. The tissue dilation tubes can be preassembled prior to use by utilizing a dilation tube retention assembly which can maintain the dilation tubes in a substantially fixed position and release the tubes therefrom in order to dilate a patient's tissue. Methods of producing the present systems and using the present systems in surgical procedures are also disclosed.

30 Claims, 46 Drawing Sheets

Related U.S. Application Data 2005, now Pat. No. 9,387,313, which is a continuation-in-part of application No. 10/911,215, filed on Aug. 3, 2004, now abandoned, and a continuation-in-part of application No. 11/038,784, filed on Jan. 19, 2005, now abandoned.

(60) Provisional application No. 60/674,841, filed on Apr. 26, 2005.

(51) Int. Cl.

| | |
|---|---|
| C07H 21/00 | (2006.01) |
| A61B 1/00 | (2006.01) |
| A61B 1/018 | (2006.01) |
| A61B 1/04 | (2006.01) |
| A61B 1/06 | (2006.01) |
| A61B 17/17 | (2006.01) |
| A61B 1/07 | (2006.01) |
| A61B 1/32 | (2006.01) |
| A61B 17/12 | (2006.01) |
| A61B 17/00 | (2006.01) |

(52) U.S. Cl.
CPC .......... *A61B 1/00133* (2013.01); *A61B 1/018* (2013.01); *A61B 1/04* (2013.01); *A61B 1/06* (2013.01); *A61B 1/0684* (2013.01); *A61B 1/07* (2013.01); *A61B 1/32* (2013.01); *A61B 17/17* (2013.01); *A61B 17/1757* (2013.01); *A61M 25/00* (2013.01); *C07H 21/00* (2013.01); *A61B 1/00032* (2013.01); *A61B 1/00066* (2013.01); *A61B 17/12022* (2013.01); *A61B 2017/0034* (2013.01); *A61B 2017/00991* (2013.01); *A61M 2207/00* (2013.01)

(56) References Cited

U.S. PATENT DOCUMENTS

| | | |
|---|---|---|
| 3,811,449 A | 5/1974 | Gravlee et al. |
| 3,848,601 A | 11/1974 | Ma et al. |
| 4,350,151 A | 9/1982 | Scott |
| 4,369,790 A | 1/1983 | McCarthy |
| 4,401,433 A | 8/1983 | Luther |
| 4,449,532 A | 5/1984 | Storz |
| 4,450,835 A | 5/1984 | Asnis et al. |
| 4,451,256 A | 5/1984 | Weikl et al. |
| 4,545,371 A | 10/1985 | Grossmann et al. |
| 4,545,374 A | 10/1985 | Jacobson |
| 4,573,448 A | 3/1986 | Kambin |
| 4,601,710 A | 7/1986 | Moll |
| 4,629,450 A | 12/1986 | Suzuki et al. |
| 4,686,984 A | 8/1987 | Bonnet |
| 4,790,817 A | 12/1988 | Luther |
| 4,802,479 A | 2/1989 | Haber et al. |
| 4,862,891 A | 9/1989 | Smith |
| 4,966,587 A | 10/1990 | Baumgart |
| 4,978,334 A | 12/1990 | Toye et al. |
| 4,981,482 A | 1/1991 | Ichikawa |
| 4,994,027 A | 2/1991 | Farrell |
| 5,002,557 A | 3/1991 | Hasson |
| 5,064,414 A | 11/1991 | Revane |
| 5,084,043 A | 1/1992 | Hertzmann et al. |
| 5,114,407 A | 5/1992 | Burbank |
| 5,139,486 A | 8/1992 | Moss |
| 5,158,543 A * | 10/1992 | Lazarus ............ A61B 17/3417 604/164.1 |
| 5,167,664 A | 12/1992 | Hodorek |
| 5,171,279 A | 12/1992 | Mathews |
| 5,176,651 A | 1/1993 | Allgood et al. |
| 5,176,697 A | 1/1993 | Hasson et al. |
| 5,183,464 A | 2/1993 | Dubrul et al. |
| 5,188,118 A | 2/1993 | Terwilliger |
| 5,195,506 A | 3/1993 | Hulfish |
| 5,224,952 A | 7/1993 | Deniega et al. |
| 5,241,972 A | 9/1993 | Bonati |
| 5,242,410 A | 9/1993 | Melker |
| 5,242,427 A | 9/1993 | Bilweis |
| 5,269,797 A | 12/1993 | Bonati et al. |
| 5,280,782 A | 1/1994 | Wilk |
| 5,290,243 A | 3/1994 | Chodorow et al. |
| 5,304,142 A | 4/1994 | Liebl et al. |
| 5,312,417 A | 5/1994 | Wilk |
| 5,324,261 A | 6/1994 | Amundson et al. |
| 5,342,382 A | 8/1994 | Brinkerhoff et al. |
| 5,407,430 A | 4/1995 | Peters |
| 5,441,504 A | 8/1995 | Pohndorf et al. |
| 5,454,790 A | 10/1995 | Dubrul |
| 5,472,426 A * | 12/1995 | Bonati ............... A61B 17/1604 600/564 |
| 5,474,539 A | 12/1995 | Costa et al. |
| 5,486,190 A | 1/1996 | Green |
| 5,505,710 A * | 4/1996 | Dorsey, III ........... A61M 1/008 604/158 |
| 5,512,037 A | 4/1996 | Russell et al. |
| 5,569,248 A | 10/1996 | Mathews |
| 5,569,251 A | 10/1996 | Baker et al. |
| 5,569,290 A | 10/1996 | McAfee |
| 5,613,950 A | 3/1997 | Yoon |
| 5,624,447 A | 4/1997 | Myers |
| 5,639,276 A | 6/1997 | Weinstock et al. |
| 5,647,857 A | 7/1997 | Anderson et al. |
| 5,685,856 A * | 11/1997 | Lehrer ............... A61B 17/3496 604/164.1 |
| 5,707,359 A | 1/1998 | Bufalini |
| 5,713,870 A | 2/1998 | Yoon |
| 5,728,097 A | 3/1998 | Mathews |
| 5,743,881 A * | 4/1998 | Demco ............... A61B 17/3417 604/158 |
| 5,752,969 A | 5/1998 | Cunci et al. |
| 5,772,678 A | 6/1998 | Thomason et al. |
| 5,776,156 A | 7/1998 | Shikhman |
| 5,782,800 A | 7/1998 | Yoon |
| 5,792,044 A | 8/1998 | Foley et al. |
| 5,810,259 A | 9/1998 | Sinclair |
| 5,810,721 A | 9/1998 | Mueller et al. |
| 5,810,866 A | 9/1998 | Yoon |
| 5,846,259 A | 12/1998 | Berthiaume |
| 5,851,216 A | 12/1998 | Allen |
| 5,873,854 A | 2/1999 | Wolvek |
| 5,902,231 A | 5/1999 | Foley et al. |
| 5,957,902 A | 9/1999 | Teves |
| 5,964,730 A | 10/1999 | Williams et al. |
| 5,967,783 A | 10/1999 | Ura |
| 5,976,146 A | 11/1999 | Ogawa et al. |
| 5,989,255 A | 11/1999 | Pepper et al. |
| 5,997,510 A | 12/1999 | Schwemberger |
| 6,007,519 A | 12/1999 | Rosselli |
| 6,030,364 A | 2/2000 | Durgin et al. |
| 6,033,406 A | 3/2000 | Mathews |
| 6,048,309 A | 4/2000 | Flom et al. |
| 6,053,935 A | 4/2000 | Brenneman et al. |
| 6,066,142 A | 5/2000 | Serbousek et al. |
| 6,117,174 A | 9/2000 | Nolan |
| 6,159,179 A | 12/2000 | Simonson |
| 6,162,236 A | 12/2000 | Osada |
| 6,197,041 B1 | 3/2001 | Shichman et al. |
| 6,200,322 B1 | 3/2001 | Branch et al. |
| 6,206,826 B1 | 3/2001 | Mathews et al. |
| 6,206,922 B1 | 3/2001 | Zdeblick et al. |
| 6,213,957 B1 | 4/2001 | Milliman et al. |
| 6,217,509 B1 | 4/2001 | Foley et al. |
| 6,228,058 B1 | 5/2001 | Dennis et al. |
| 6,264,676 B1 | 7/2001 | Gellman et al. |
| 6,293,909 B1 | 9/2001 | Chu et al. |
| 6,293,952 B1 | 9/2001 | Brosens et al. |
| 6,319,272 B1 | 11/2001 | Brenneman et al. |
| 6,348,053 B1 | 2/2002 | Cachia |
| 6,361,557 B1 | 3/2002 | Gittings et al. |
| 6,361,559 B1 | 3/2002 | Houser et al. |
| 6,364,897 B1 | 4/2002 | Bonutti |
| 6,368,351 B1 | 4/2002 | Glenn et al. |

(56) References Cited

U.S. PATENT DOCUMENTS

| | | | |
|---|---|---|---|
| 6,371,971 B1 * | 4/2002 | Tsugita | A61F 2/01 606/200 |
| 6,428,541 B1 | 8/2002 | Boyd et al. | |
| 6,428,556 B1 | 8/2002 | Chin | |
| 6,440,154 B2 | 8/2002 | Gellman et al. | |
| 6,447,527 B1 | 9/2002 | Thompson et al. | |
| 6,447,540 B1 | 9/2002 | Fontaine et al. | |
| 6,450,989 B2 | 9/2002 | Dubrul et al. | |
| 6,471,724 B2 | 10/2002 | Zdeblick et al. | |
| 6,475,226 B1 | 11/2002 | Belef et al. | |
| 6,478,029 B1 | 11/2002 | Boyd et al. | |
| 6,494,860 B2 | 12/2002 | Rocamora et al. | |
| 6,494,893 B2 | 12/2002 | Dubrul et al. | |
| 6,511,481 B2 | 1/2003 | Von et al. | |
| 6,520,907 B1 | 2/2003 | Foley et al. | |
| 6,554,852 B1 * | 4/2003 | Oberlander | A61B 17/0401 606/104 |
| 6,562,046 B2 | 5/2003 | Sasso | |
| 6,562,049 B1 | 5/2003 | Norlander et al. | |
| 6,582,390 B1 | 6/2003 | Sanderson | |
| 6,582,437 B2 | 6/2003 | Dorchak et al. | |
| 6,582,441 B1 | 6/2003 | He et al. | |
| 6,589,240 B2 | 7/2003 | Hinchliffe | |
| 6,592,553 B2 | 7/2003 | Zhang et al. | |
| 6,607,530 B1 | 8/2003 | Carl et al. | |
| 6,616,678 B2 | 9/2003 | Nishtala et al. | |
| 6,632,224 B2 | 10/2003 | Cachia et al. | |
| 6,635,362 B2 | 10/2003 | Zheng | |
| 6,641,564 B1 | 11/2003 | Kraus | |
| 6,648,890 B2 | 11/2003 | Culbert et al. | |
| 6,655,962 B1 | 12/2003 | Kennard | |
| 6,666,891 B2 | 12/2003 | Boehm et al. | |
| 6,679,833 B2 | 1/2004 | Smith et al. | |
| 6,685,706 B2 | 2/2004 | Padget et al. | |
| 6,689,152 B2 | 2/2004 | Balceta et al. | |
| 6,695,851 B2 | 2/2004 | Zdeblick et al. | |
| 6,719,760 B2 | 4/2004 | Dorchak et al. | |
| 6,723,096 B1 | 4/2004 | Dorchak et al. | |
| 6,743,166 B2 | 6/2004 | Berci et al. | |
| 6,746,451 B2 | 6/2004 | Middleton et al. | |
| 6,793,656 B1 | 9/2004 | Mathews | |
| 6,929,606 B2 | 8/2005 | Ritland | |
| 7,025,746 B2 | 4/2006 | Tal | |
| 7,172,612 B2 | 2/2007 | Ishikawa | |
| 7,434,325 B2 | 10/2008 | Foley et al. | |
| 7,762,995 B2 | 7/2010 | Eversull et al. | |
| 2001/0012950 A1 | 8/2001 | Nishtala et al. | |
| 2001/0027320 A1 | 10/2001 | Sasso | |
| 2001/0037126 A1 | 11/2001 | Stack et al. | |
| 2001/0049529 A1 | 12/2001 | Cachia et al. | |
| 2001/0049530 A1 | 12/2001 | Culbert et al. | |
| 2002/0001476 A1 | 1/2002 | Nagamine et al. | |
| 2002/0032462 A1 | 3/2002 | Houser et al. | |
| 2002/0087152 A1 | 7/2002 | Mikus et al. | |
| 2002/0143333 A1 | 10/2002 | Von et al. | |
| 2002/0143334 A1 | 10/2002 | Hoffmann et al. | |
| 2002/0143335 A1 | 10/2002 | Von et al. | |
| 2003/0004528 A1 * | 1/2003 | Ishikawa | A61B 17/3415 606/169 |
| 2003/0069582 A1 | 4/2003 | Culbert | |
| 2003/0083688 A1 | 5/2003 | Simonson | |
| 2003/0097132 A1 | 5/2003 | Padget et al. | |
| 2003/0139648 A1 | 7/2003 | Foley et al. | |
| 2003/0153874 A1 | 8/2003 | Tal | |
| 2003/0187431 A1 | 10/2003 | Simonson | |
| 2003/0208220 A1 | 11/2003 | Worley et al. | |
| 2003/0233102 A1 | 12/2003 | Nakamura et al. | |
| 2004/0010257 A1 | 1/2004 | Cachia et al. | |
| 2004/0019359 A1 | 1/2004 | Worley et al. | |
| 2004/0039400 A1 * | 2/2004 | Schmieding | A61B 17/0281 606/108 |
| 2004/0049223 A1 | 3/2004 | Nishtala et al. | |
| 2004/0056339 A1 | 3/2004 | Troost | |
| 2004/0059339 A1 | 3/2004 | Roehm et al. | |
| 2004/0059350 A1 | 3/2004 | Gordon et al. | |
| 2004/0106925 A1 | 6/2004 | Culbert | |
| 2004/0127906 A1 | 7/2004 | Culbert et al. | |
| 2004/0138665 A1 | 7/2004 | Padget et al. | |
| 2004/0143284 A1 | 7/2004 | Chin | |
| 2004/0147877 A1 | 7/2004 | Heuser | |
| 2004/0147950 A1 | 7/2004 | Mueller et al. | |
| 2004/0158258 A1 | 8/2004 | Bonati et al. | |
| 2004/0181222 A1 | 9/2004 | Culbert et al. | |
| 2004/0199162 A1 | 10/2004 | Von et al. | |
| 2004/0199165 A1 | 10/2004 | Culbert et al. | |
| 2004/0260289 A1 | 12/2004 | Padget et al. | |
| 2004/0260297 A1 | 12/2004 | Padget et al. | |
| 2005/0033289 A1 | 2/2005 | Warren et al. | |
| 2005/0080443 A1 * | 4/2005 | Fallin | A61B 17/3417 606/191 |
| 2006/0004398 A1 | 1/2006 | Binder et al. | |
| 2006/0020284 A1 * | 1/2006 | Foley | A61B 17/025 606/191 |
| 2006/0200186 A1 | 9/2006 | Marchek et al. | |
| 2009/0240335 A1 | 9/2009 | Arcenio et al. | |
| 2011/0208226 A1 | 8/2011 | Fatone et al. | |

FOREIGN PATENT DOCUMENTS

| | | |
|---|---|---|
| JP | 2003-010197 A | 1/2003 |
| JP | 2003-026266 A | 1/2003 |
| JP | 2004-194731 A | 7/2004 |
| WO | 93/04652 A1 | 3/1993 |
| WO | 00/67652 A2 | 11/2000 |
| WO | 2006/017507 A2 | 2/2006 |

OTHER PUBLICATIONS

Jun. 20, 2013 Office Action for Application No. 05777628.8.

International Search Report and Written Opinion received in co-pending PCT Application No. PCT/US05/27431, dated Jul. 7, 2008, 9 pages.

Feb. 7, 2011 Office Action for Japanese Application No. 2007-524917 filed on Aug. 2, 2005.

European Patent Office; Extended Search Report of related European Patent Application No. EP 05777628.8. Report dated Mar. 14, 2012.

European Examination Report, re EPO Application No. 05777628.8, dated Jan. 15, 2015.

Apr. 2, 2012 Office Action (to proceed and to respond to Search Report) for Application No. 05777628.8.

Feb. 24, 2012 Office Action for Japanese Application No. 2007-524917 filed Aug. 2, 2005.

European Examination Report, re EPO Application No. 05777628.8, dated Nov. 27, 2015.

* cited by examiner

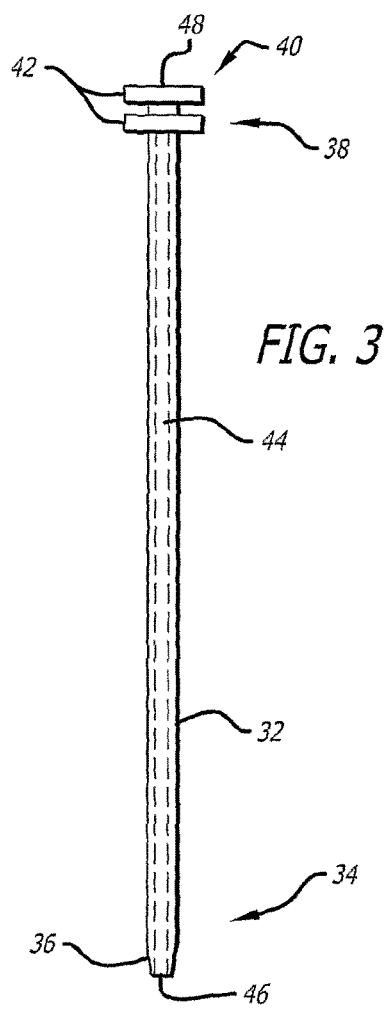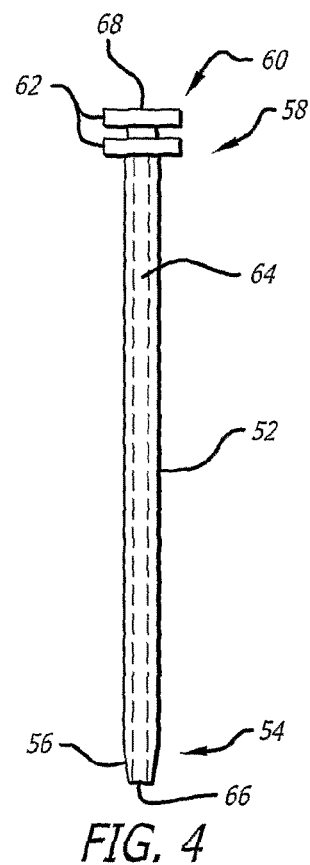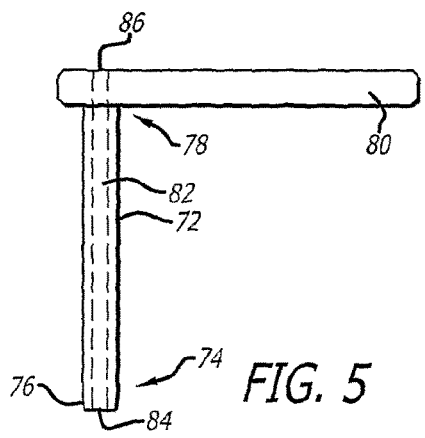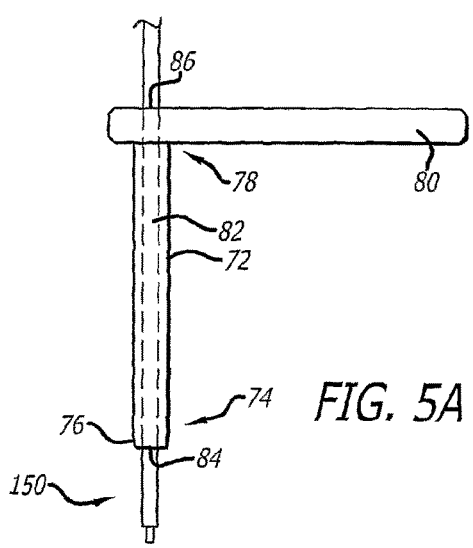
FIG. 3
FIG. 4
FIG. 5
FIG. 5A

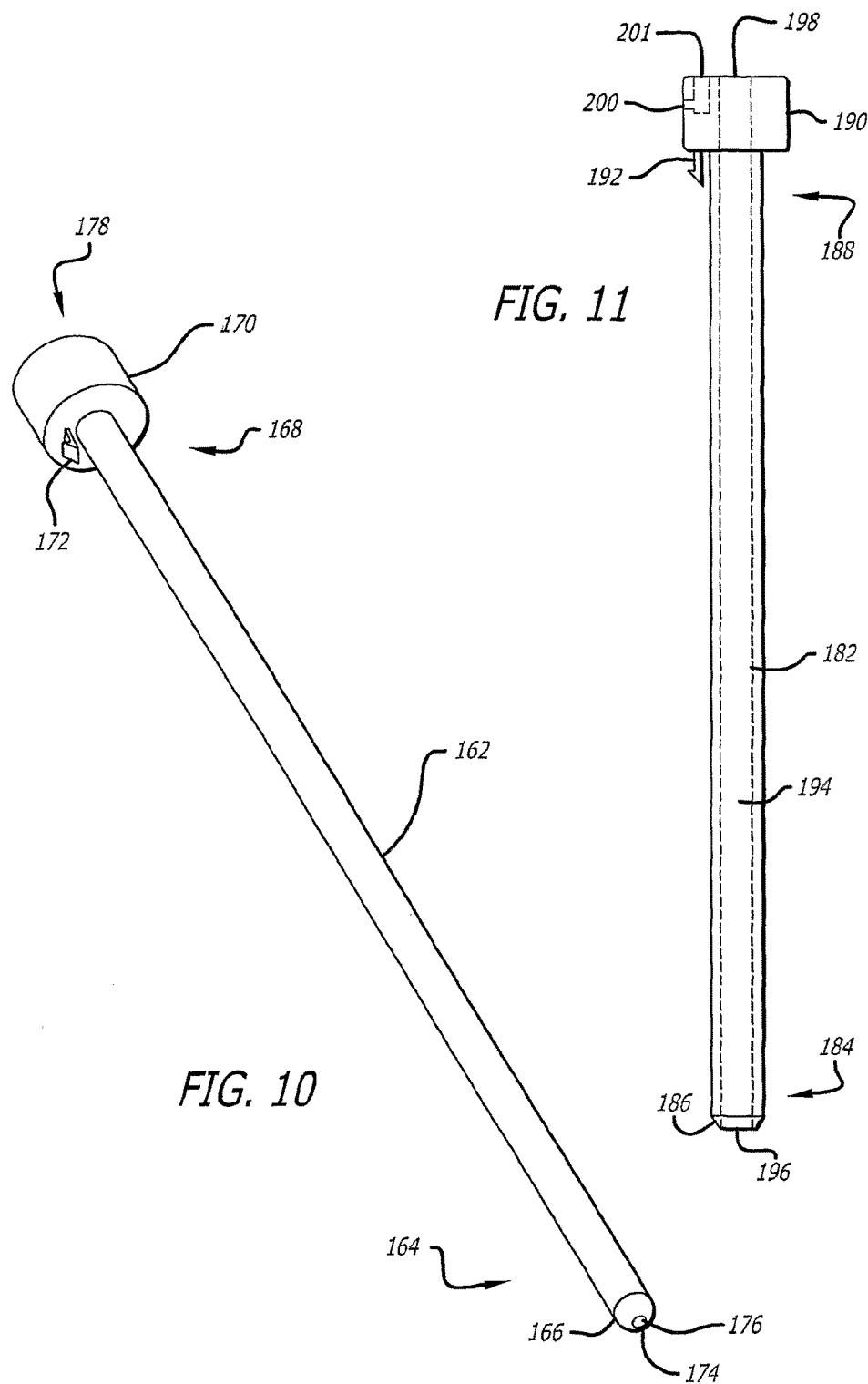

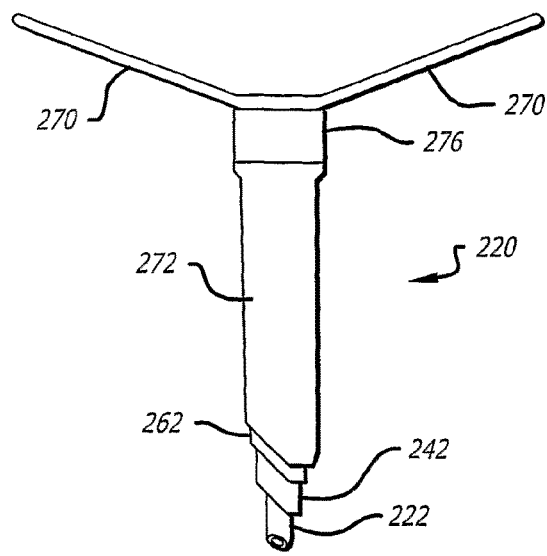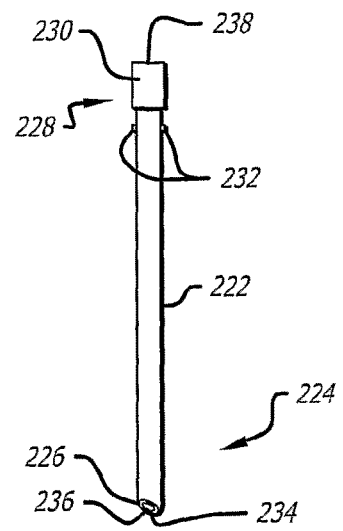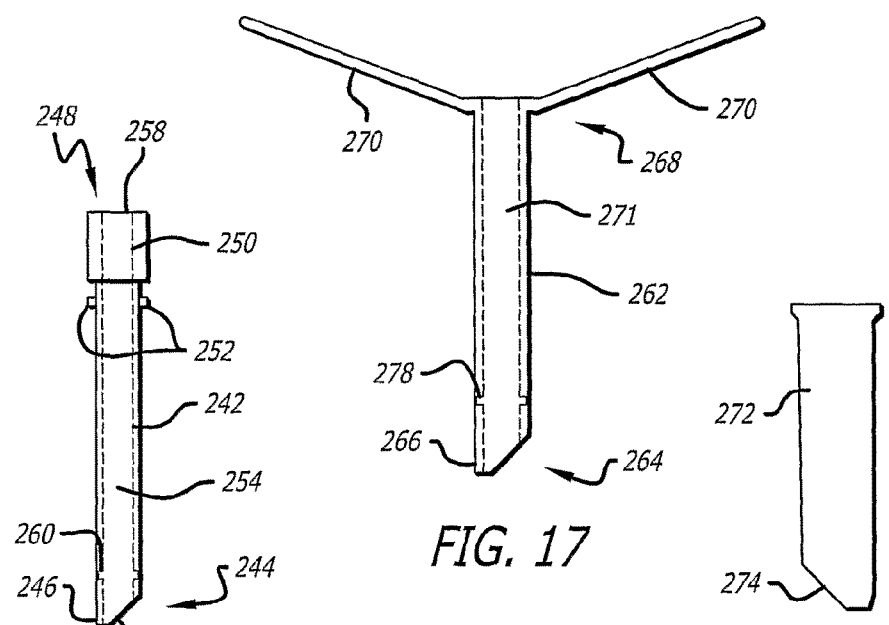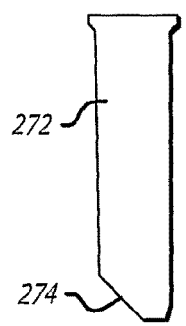
FIG. 14  FIG. 15  FIG. 16  FIG. 17  FIG. 18

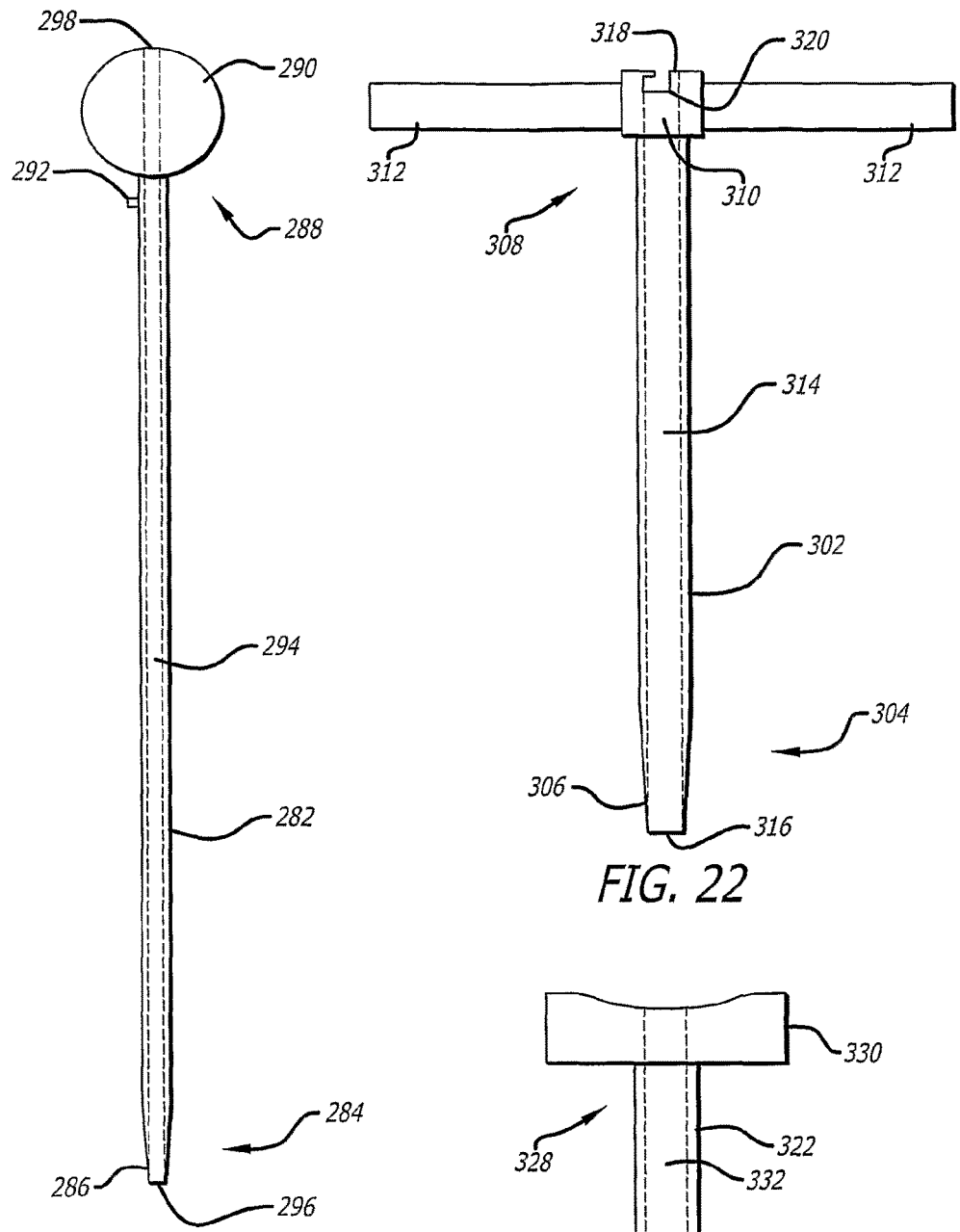
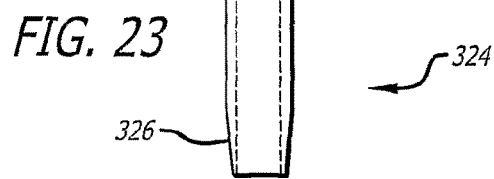
FIG. 21
FIG. 22
FIG. 23

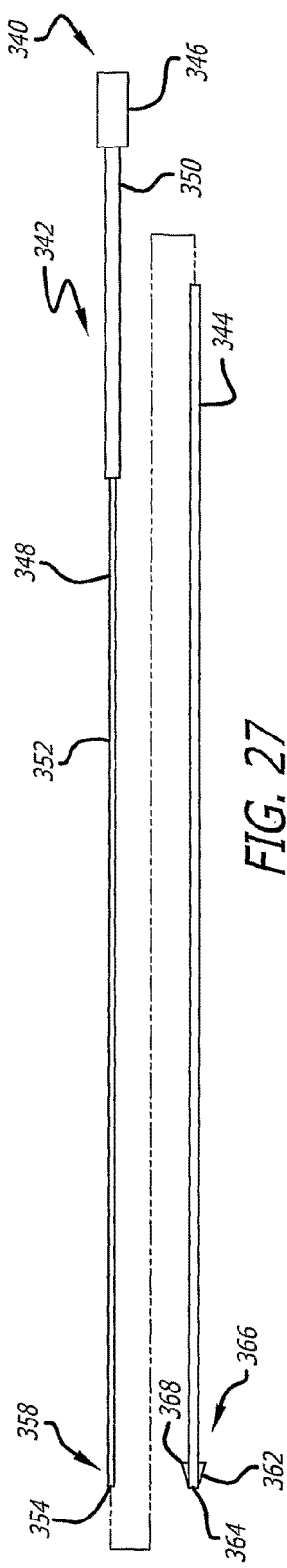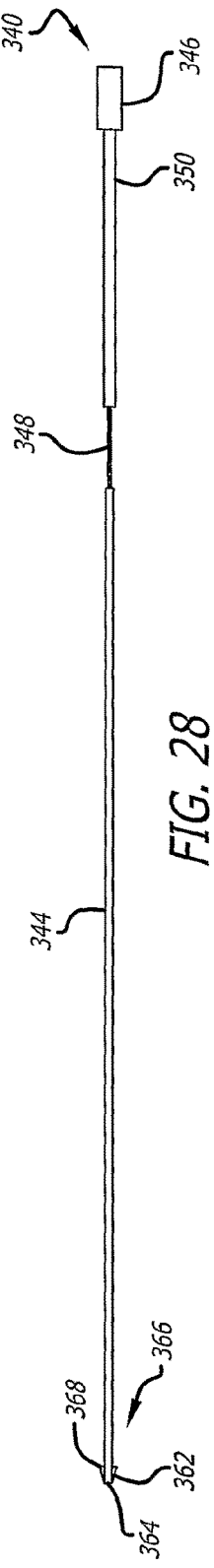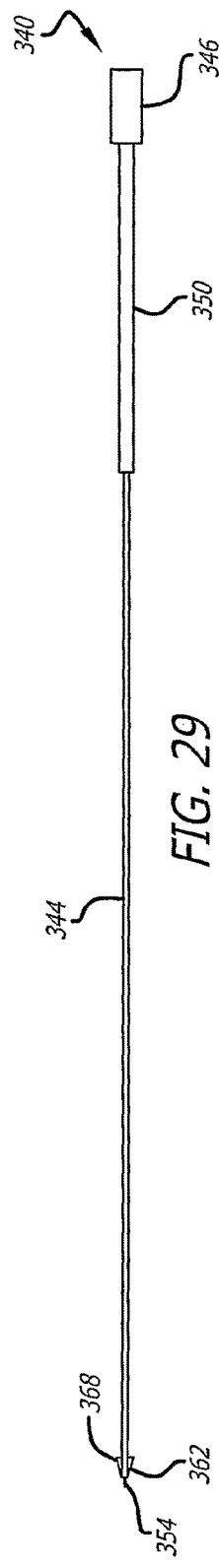

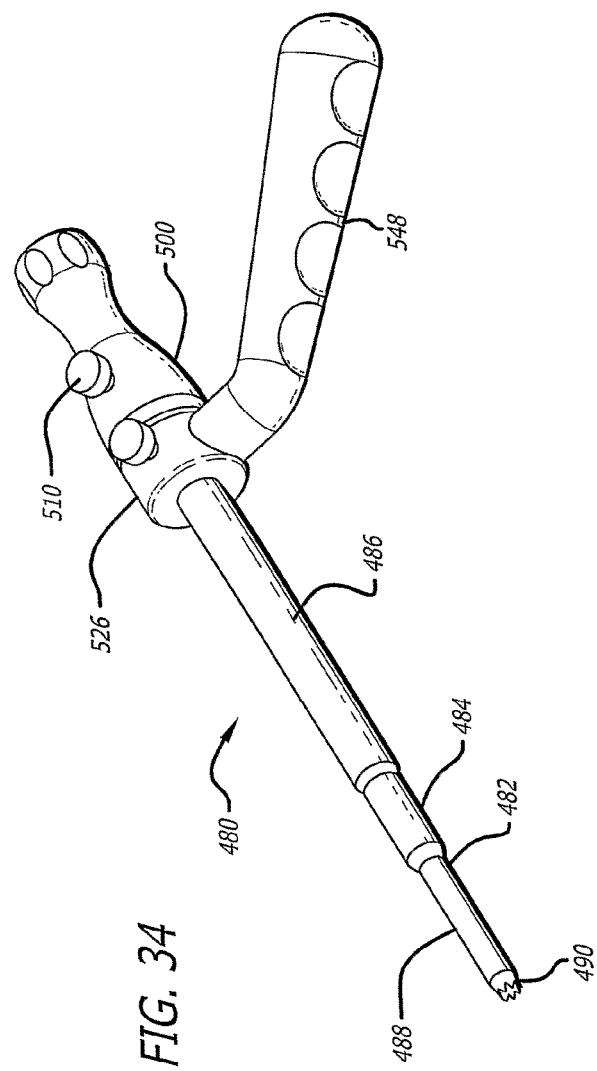
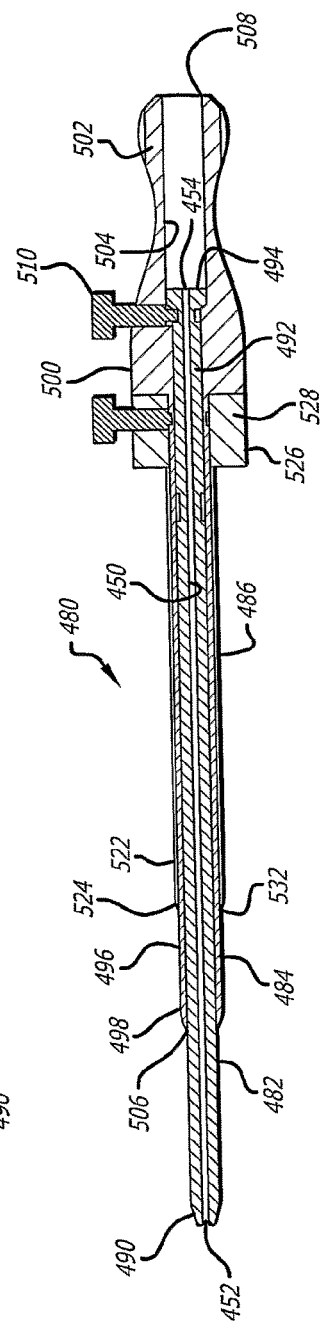
FIG. 34
FIG. 35

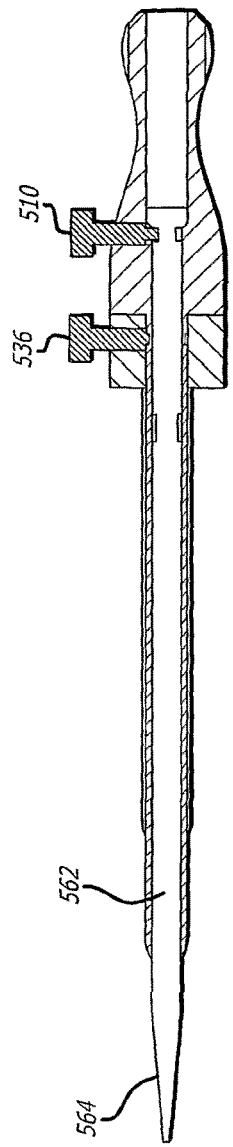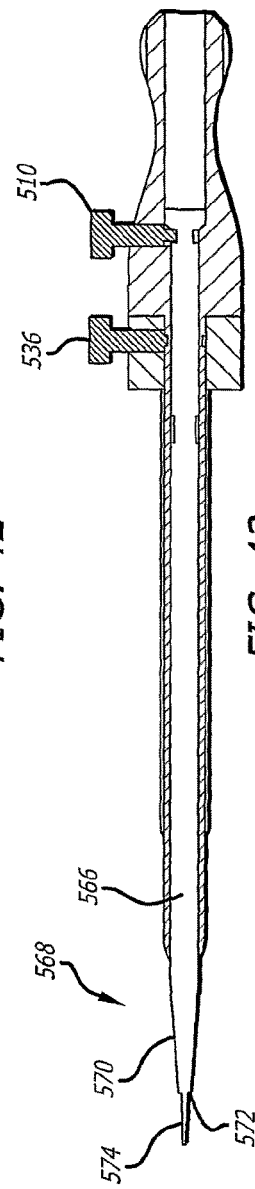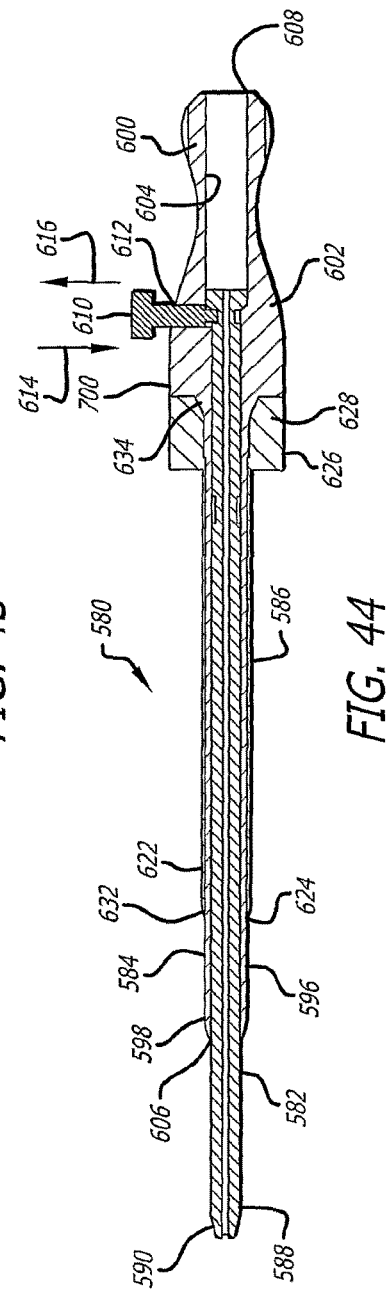

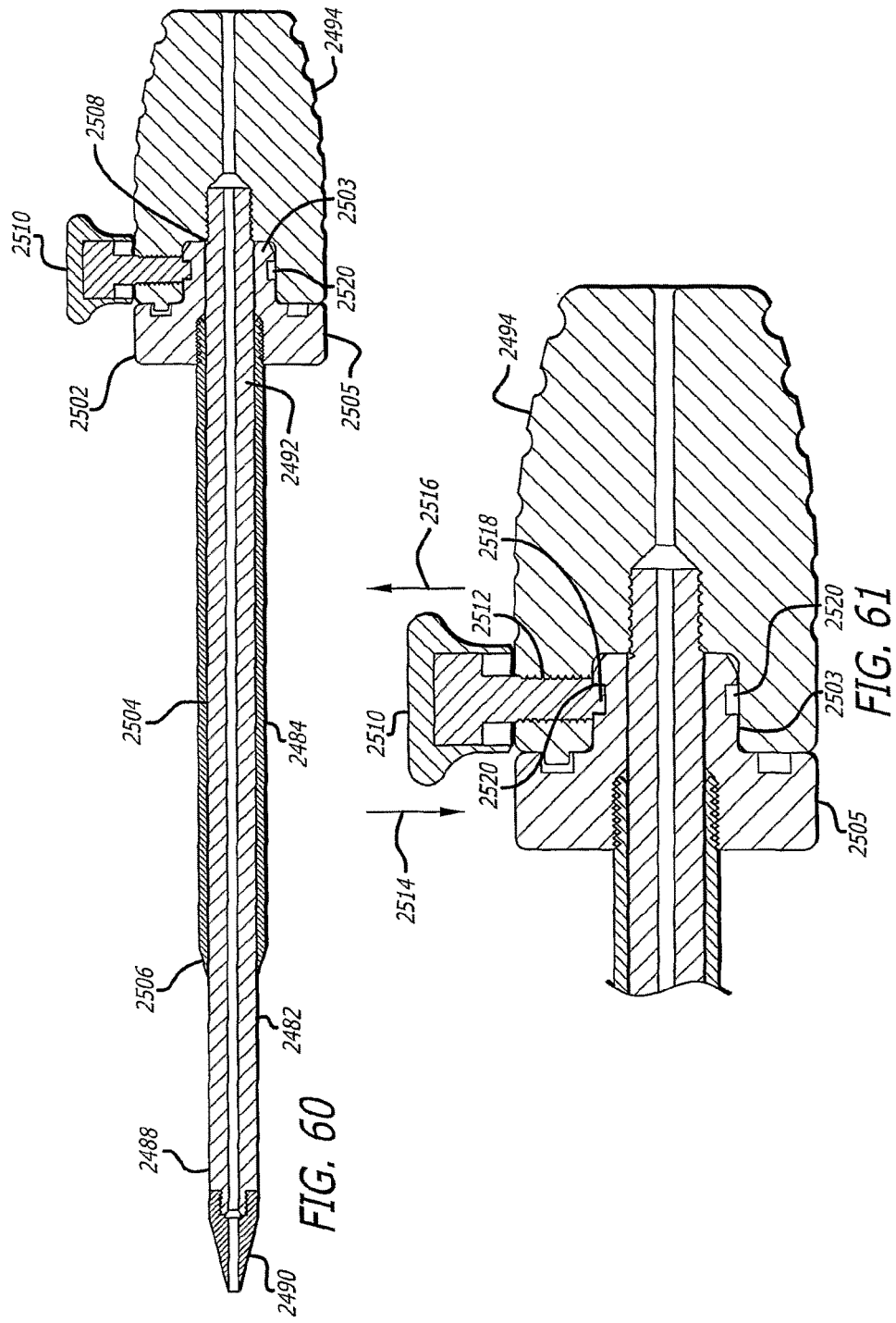

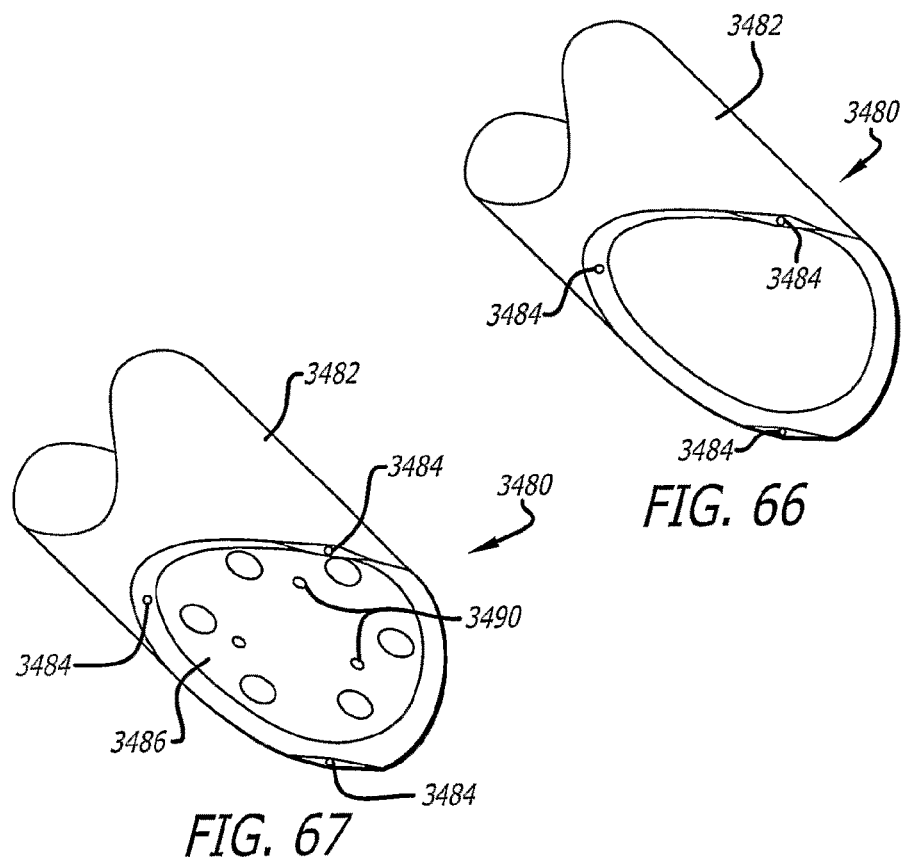
FIG. 66
FIG. 67
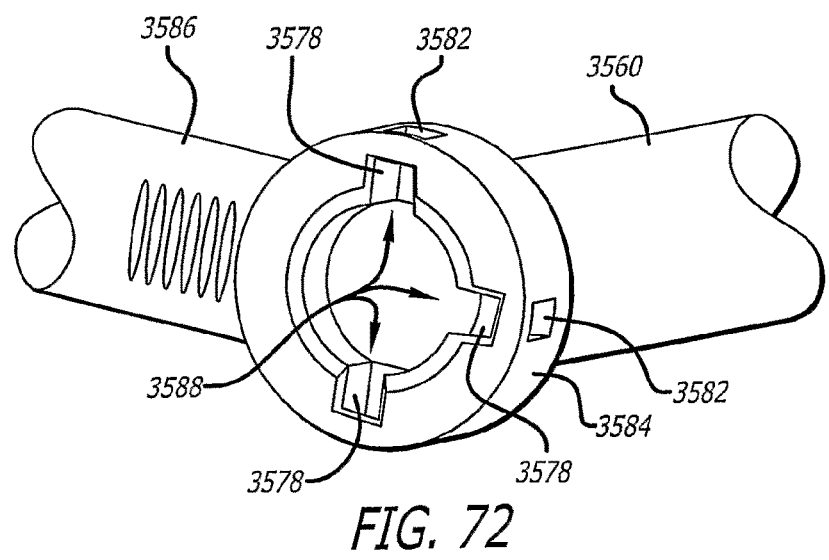
FIG. 72

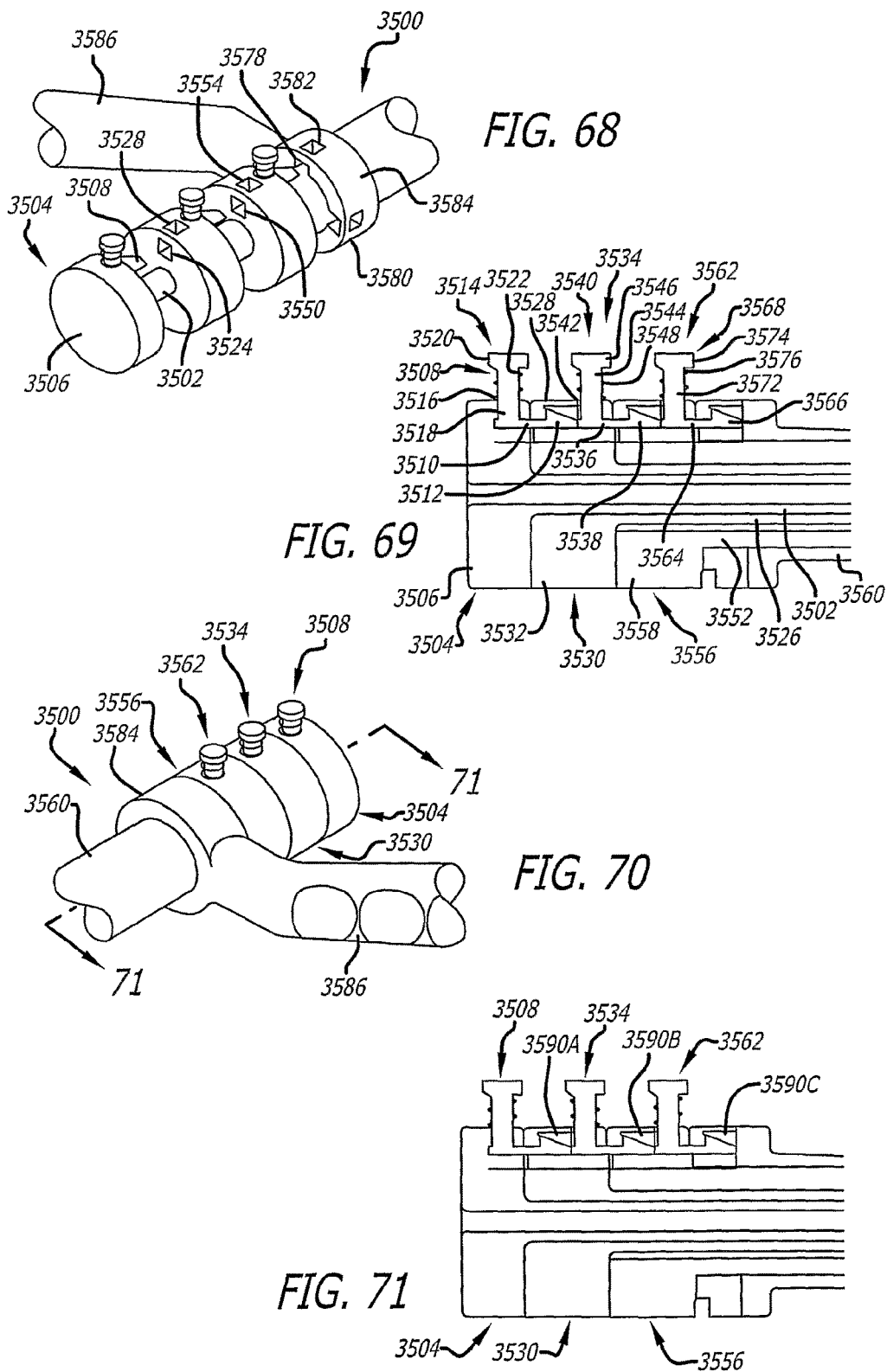

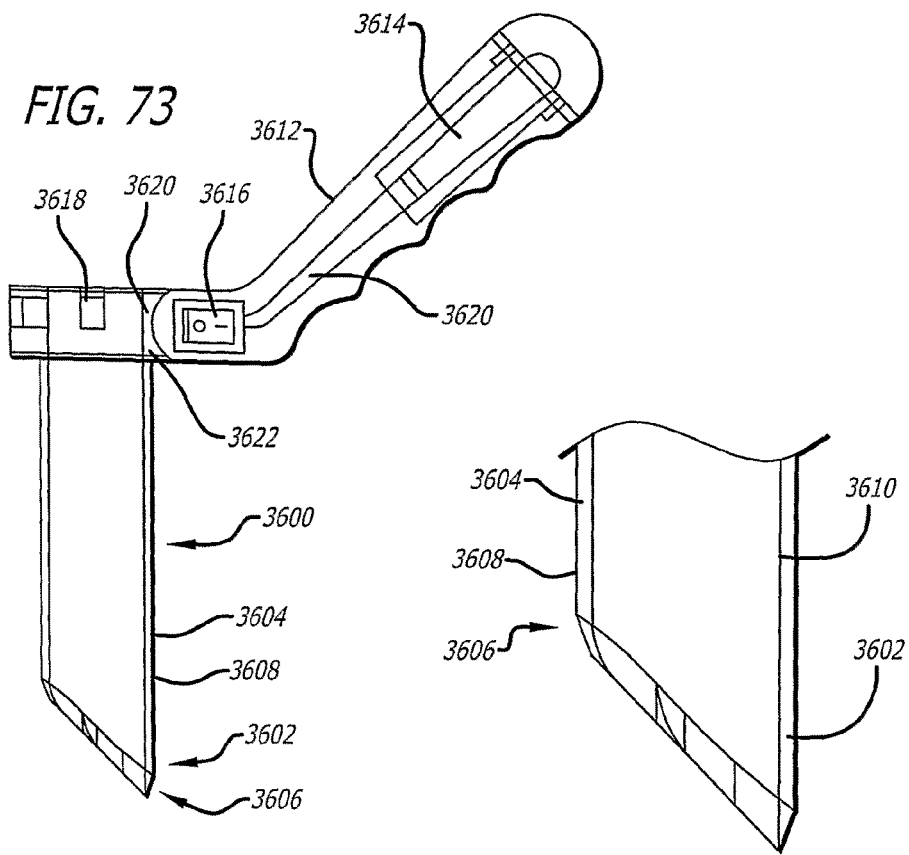
FIG. 73
FIG. 74
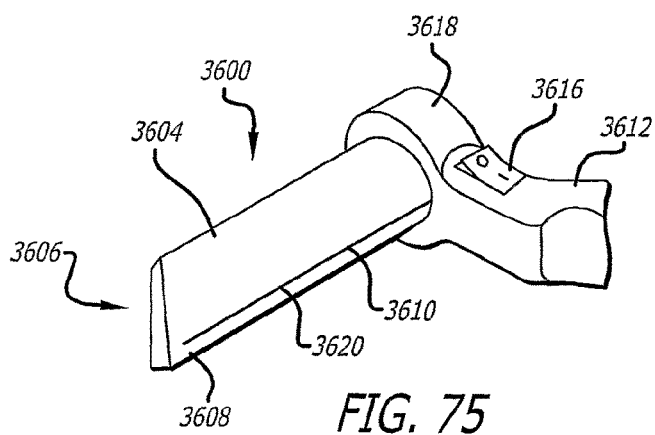
FIG. 75

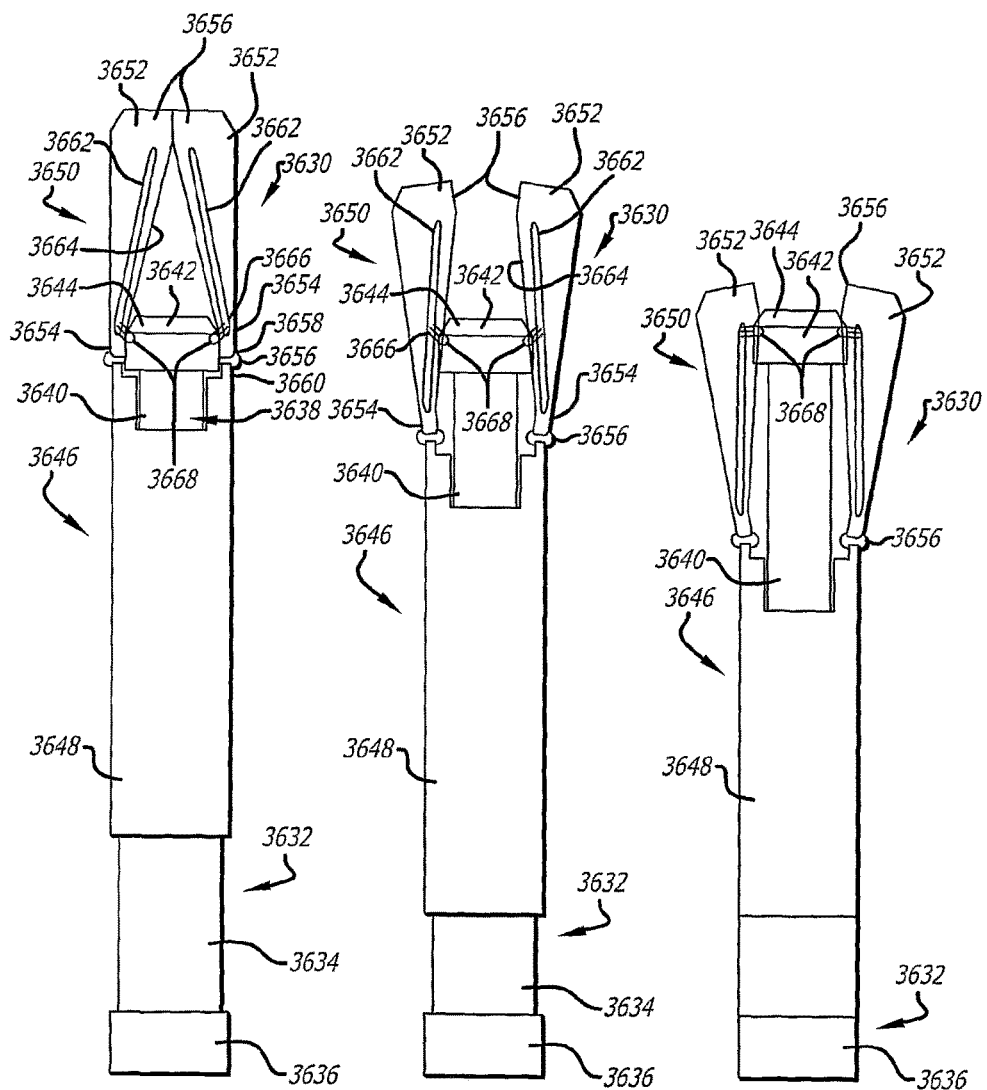

TELESCOPIC PERCUTANEOUS TISSUE DILATION SYSTEMS AND RELATED METHODS

CROSS-REFERENCE TO RELATED APPLICATIONS

This application claims the benefit of and is a continuation of U.S. application Ser. No. 11/659,025, filed Jan. 30, 2007, which is a national stage application under 35 U.S.C. § 371 of PCT Application No. PCT/US2005/027431, filed on Aug. 2, 2005, designating the United States of America and published in the English language, which claims priority under 35 U.S.C. § 119 of U.S. Provisional Application No. 60/674,841, filed Apr. 26, 2005, and PCT Application No. PCT/US2005/027431 claims the benefit of and is a continuation-in-part of U.S. application Ser. No. 11/038,784, filed Jan. 19, 2005, and claims the benefit of and is a continuation-in-part U.S. application Ser. No. 10/911,215, filed Aug. 3, 2004, the entire contents of each of which are hereby incorporated by reference.

FIELD OF THE INVENTION

The present invention generally relates to medical devices and methods. More specifically, the present invention relates to medical devices that dilate tissue of a patient to provide access through the skin to a target site of the patient for medical procedures, as well as methods of using such devices, methods of making such devices, and kits or packages containing such devices.

BACKGROUND

In order to perform a surgical procedure on a target structure of a patient, such as when accessing bony structures, including hips or proximal femurs and vertebral regions, in a patient's body, it is often necessary or at least desirable to dilate the tissue to provide access to the target structure.

One method of providing access to a target structure is to form an incision through the skin and the tissue located between the skin and the target structure and retracting the cut tissue to form an access area. Cutting the tissue is very traumatic to the tissue and is associated with prolonged recovery times and substantial patient discomfort.

Another method of dilating tissue in connection with such procedures employs dilating tissue using multiple separate cannula dilators. Typically, a set of dilators having different diameters will be used. For example, a first dilator of a relatively small outer diameter will be inserted through an incision formed in the patient's skin toward a target structure. A second cannula having an inner diameter substantially equal to the outer diameter of the first dilator will be placed over the first dilator. A third cannula having an inner diameter substantially equal to the outer diameter of the second cannula will be placed over the second cannula. This stepwise dilation of tissue proceeds until an adequate access path is provided to the target structure. This method may be understood to be similar to blunt dissection of the tissue, and may result in less trauma to the tissue and less discomfort to the patient compared to cutting the tissue. However, this method requires substantial amounts of time in terms of requiring serial steps of dilating the tissue and poses significant risks in terms of increased possibilities that the dilators may be misplaced, unorganized, become contaminated, such as by being dropped in an operating room, and the like.

Fusion of two adjacent vertebrae is a common surgical treatment for back injuries due to damage or defects in a spinal disc between two adjacent vertebrae, such as conditions due to a herniated disc or disc degeneration. The entire disc may be removed by a discectomy procedure, and may be replaced with bone or a bone substitute and/or a cage in order to prevent collapse of the disc space between the adjacent vertebrae. Early techniques for stabilizing the adjacent vertebrae included application of a plate or a rod in conjunction with screws across the adjacent vertebrae, after which the adjacent vertebrae would eventually fuse together. Other stabilizing procedures or techniques may include laminectomies, laminotomies, and foraminotomies, among others. However, such techniques commonly required prolonged periods of recovery from the extensive surgery involved.

Bone fixation devices are known that are useful for connecting two or more bone segments for the healing of broken bones, typically including an elongate pin with a distal anchor and a proximal anchor movable on the pin to accommodate different bone dimensions, and to permit tensioning of the bone segments together. A surgical procedure of attaching two or more parts of a bone with a pin-like device may be performed by making an initial incision into the tissue down to the bone, and drilling a hole through the bone parts to be joined. Such bone fixation devices can be useful for fusion of vertebrae together, because such bone fixation devices can be used to join adjacent bone segments through a single percutaneous incision or puncture, without the need to expose any other side of the bone segments to be joined. In either type of procedure, that is procedures for stabilizing vertebrae using plates and rods or bone anchors, there is substantial trauma to the surrounding tissue if a large incision is required.

Thus, there remains a need for tissue dilation systems that are easy to use and do not substantially damage tissue that has been dilated.

SUMMARY

Tissue dilation systems are described which effectively dilate body tissue or tissues of a patient to provide access to a target structure or structures in a patient so that a physician can perform a surgical or medical procedure of the target structure. The present systems employ two or more telescopically arranged dilation tubes that can be preassembled and retained in a substantially fixed position or locked configuration prior to use. Individual dilation tubes can be separately unlocked or released to successively dilate a patient's tissue and to provide access to a target structure. The present systems can be used to dilate tissue in connection with medical procedures involving bones, including vertebrae, hips or proximal femurs, the heart, kidneys, lungs, liver, stomach, and other organ and body tissues. For example, there remains a need for tissue dilation systems that are easier to use than individual dilation tubes, that provide reduced trauma compared to procedures which employ cutting of tissue, and/or that provide an access path to a target structure or structures of a patient suitable for performing a medical procedure involving the target structure or structures.

In one embodiment, a telescopic tissue dilation system comprises a first dilation tube, a second dilation tube, and a dilation tube retention assembly. The first dilation tube has a proximal end and a distal end. The second dilation tube has a proximal end, a distal end, and a lumen extending from the proximal end to the distal end. The lumen is dimensioned to accommodate at least a portion of the first dilation tube. The dilation tube retention assembly is effective in retaining the second dilation tube in a substantially fixed position relative to the first dilation tube prior to dilation of tissue of an individual, and in releasing the second dilation tube from the substantially fixed position to facilitate movement of the second dilation tube towards the distal end of the first dilation tube to dilate tissue of a patient.

In another embodiment, a method of producing a percutaneous telescopic tissue dilation system, comprises inserting a first dilation tube into a lumen of a second dilation tube; and engaging a locking assembly with the first dilation tube and second dilation tube to maintain at least one of the first dilation tube and the second dilation tube in a locked configuration.

In another embodiment, a method of dilating tissue of a patient, comprises placing a telescopic tissue dilation system, as disclosed herein, against a tissue region of a patient. The first dilation tube is advanced into the patient towards a target structure. A second dilation tube is then unlocked or released from the locked configuration and is advanced into the patient towards the target structure. One or more of the inner dilation tubes can be removed from the outermost dilation tube to provide working access to the target structure.

Any feature or combination of features described herein are included within the scope of the present invention provided that the features included in any such combination are not mutually inconsistent as will be apparent from the context, this specification, and the knowledge of one of ordinary skill in the art. In addition, any feature or combination of features may be specifically excluded from any embodiment of the present invention. Additional advantages and aspects of the present invention are apparent in the following detailed description, drawings, and claims.

BRIEF DESCRIPTION OF THE DRAWINGS

FIG. 3 is a plan view of the first or inner dilator tube of the dilation introducer of FIG. 1.

FIG. 4 is a plan view of the second or intermediate dilator tube of the dilation introducer of FIG. 1.

FIG. 5 is a plan view of the third or outer dilator tube of the dilation introducer of FIG. 1.

FIG. 5A is a plan view of an outer dilator tube of a dilation introducer with a bone drill extending from the distal end of the dilator tube.

FIG. 10 is a perspective view of the first or inner dilator tube of the dilation introducer of FIG. 8.

FIG. 11 is a perspective view of the second or intermediate dilator tube of the dilation introducer of FIG. 8.

FIG. 14 is a plan view of the dilation introducer of FIG. 13 shown in an unlocked, collapsed configuration.

FIG. 15 is a plan view of the first or inner dilator tube of the dilation introducer of FIG. 13.

FIG. 16 is a plan view of the second or intermediate dilator tube of the dilation introducer of FIG. 13.

FIG. 17 is a plan view of the third or outer dilator tube of the dilation introducer of FIG. 13.

FIG. 18 is a plan view of the plastic sleeve of the dilation introducer of FIG. 13.

FIG. 21 is a plan view of the first or inner dilator tube of the dilation introducer of FIG. 19.

FIG. 22 is a plan view of the second or intermediate dilator tube of the dilation introducer of FIG. 19.

FIG. 23 is a plan view of the third or outer dilator tube of the dilation introducer of FIG. 19.

FIG. 27 is a plan view of a guide wire assembly for use with the various embodiments of the telescoping dilation introducer of the invention, shown disassembled.

FIG. 28 is a plan view of the guide wire assembly of FIG. 27, shown partially assembled.

FIG. 29 is a plan view of the guide wire assembly of FIG. 27, shown fully assembled.

FIG. 34 is a perspective view of view of a fifth embodiment of a dilation introducer in a locked configuration, according to the present invention.

FIG. 35 is a cross-sectional view of the dilation introducer of FIG. 34.

FIG. 42 is a cross-sectional view of the dilation introducer of FIG. 34 illustrating a second variation of the first inner dilator.

FIG. 43 is a cross-sectional view of the dilation introducer of FIG. 34 illustrating a third variation of the first inner dilator.

FIG. 44 is a cross-sectional view through yet another embodiment of the dilation introducer in a locked configuration.

FIG. 60 is a longitudinal cross sectional view of the dilation introducer in FIG. 59.

FIG. 61 is a magnified longitudinal cross sectional view through the latching and anti-rotation features of the dilation introducer in FIG. 59 shown in a locked configuration.

FIG. 66 is a perspective of another variation of the outer dilator tube of the embodiment of FIGS. 8-12, with an angled tip and spikes.

FIG. 67 is a perspective view of the outer dilator tube of FIG. 66, with a parallel guide with spikes.

FIG. 68 is a perspective view of a fifth embodiment of a dilation introducer in an unlocked configuration, according to the present invention.

FIG. 69 is a sectional view of a portion of the dilation introducer of FIG. 68.

FIG. 70 is a perspective view of a variation of the dilation introducer of FIG. 68, shown in a locked configuration, according to the present invention.

FIG. 71 is a sectional view of a portion of the dilation introducer of FIG. 68 taken along line 71-71 of FIG. 70.

FIG. 72 is a top perspective view of the head end of the handle of the dilation introducer of FIG. 68, showing multiple locking locations.

FIG. 73 is a schematic diagram of a variation of the dilation introducer of FIG. 68, with a light emitter and switch for the light emitter.

FIG. 74 is an enlarged view of the tip of the dilation introducer of FIG. 73.

FIG. 75 is a perspective view of another variation of the dilation introducer of FIG. 73, with an exterior groove for one or more elongated energy conducting members.

FIG. 76 is a side elevational view of a telescoping expander sleeve shown in an extended, unexpanded configuration.

FIG. 77 is a side elevational view of the telescoping expander sleeve of FIG. 76 shown in an intermediate partially collapsed, partially expanded configuration.

FIG. 78 is a side elevational view of the telescoping expander sleeve of FIG. 76 shown in a fully collapsed, fully expanded configuration.

DETAILED DESCRIPTION

Figure 1:
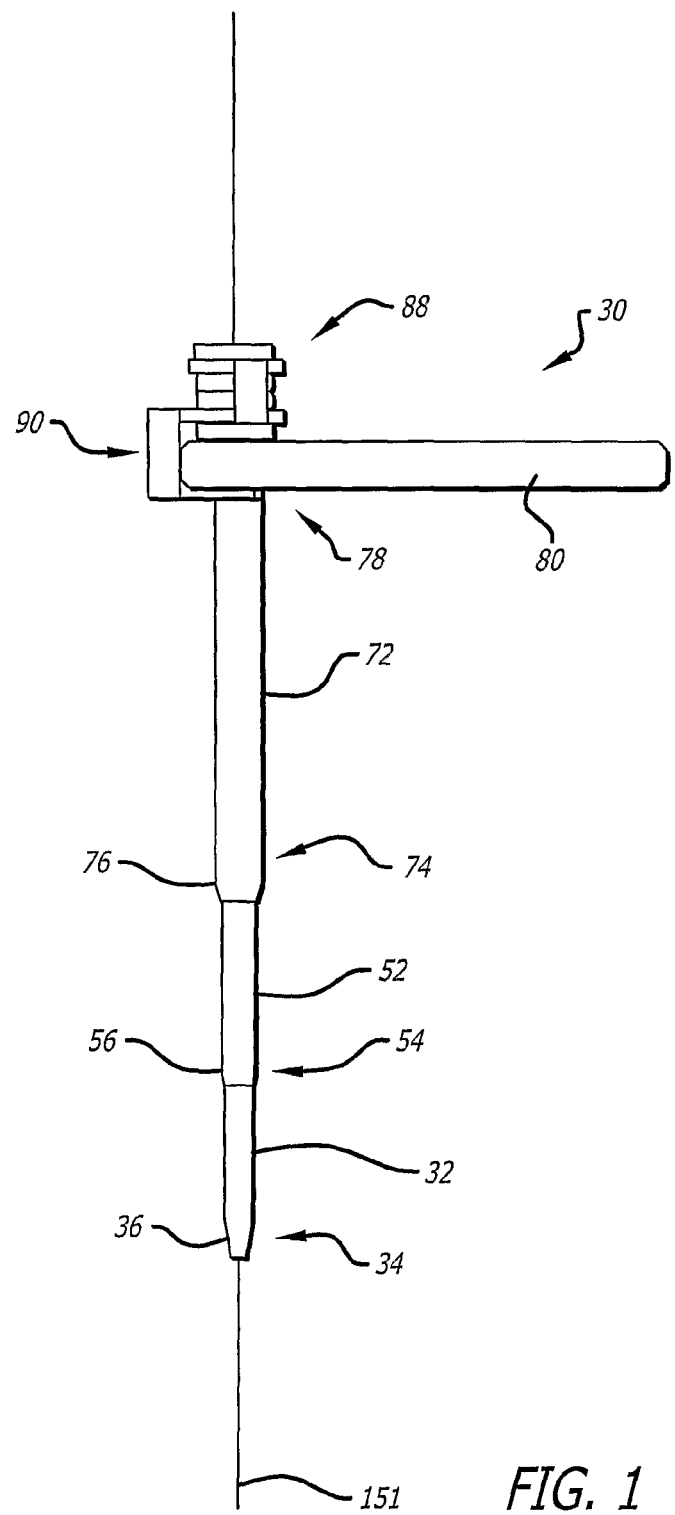
FIG. 1 is a plan view of a first embodiment of a dilation introducer in a locked configuration, according to the present invention.

Tissue dilation systems and related methods have been invented. The present tissue dilation systems include a plurality of (e.g., two or more) tissue dilation tubes that can be inserted into an individual, such as a human or animal patient, to provide a working area for a physician to perform a medical procedure. The present systems are easy to use and provide improvements in surgical procedures and patient recovery, such as reduced surgical time, reduced patient trauma, and improved patient recovery.

The tissue dilation systems disclosed herein are typically preassembled prior to use. In other words, the components of the present tissue dilation systems can be assembled into a single apparatus that can be used to dilate soft tissue of a patient. This is in contrast to existing dilation systems currently being used which employ individual separate dilation tubes that are individually and sequentially inserted into a patient during a tissue dilation procedure.

Prior to use, components of the tissue dilation system are retained in a substantially fixed position, such as in a locked configuration. During use, individual components can be separately released from the fixed position or locked configuration and used to dilate tissue of a patient to provide access to a target structure within a patient's body. When a desired dilation of a patient's tissue has been achieved, the components of the tissue dilation system except for the outermost dilation tube can be removed to provide an access path or working area for a physician to perform a medical procedure in the patient. Thus, the present systems can be understood to be telescopic tissue dilation systems when the components of the systems are in a preassembled state or configuration. When the individual dilation tubes are released from the substantially fixed position or locked configuration, the dilation tubes can telescopically move relative to the other components of the system, such as the other dilation tubes.

The present systems can be inserted through a patient's skin and fascia, and advanced through muscle tissue and other soft tissue to provide access to a target structure located in the patient's body. Thus, the present systems can be understood to be percutaneous tissue dilation systems. For example, the present systems can be inserted through an incision formed in the patient's skin or skin and underlying fascia, and advanced through soft tissue to provide access to a bone surface of the patient. In certain embodiments, the present systems are structured to provide access to a vertebral surface or regions of the patient. In other embodiments, the present systems are structured to provide access to a portion or portions of a hip of the patient. Thus, the present systems can be used in combination with orthopedic surgical procedures, such as procedures that may employ the use of a bone anchor or similar device. In further embodiments, the tissue dilation systems can provide access to other non-bony target structures, such as kidneys, livers, gastrointestinal tract, heart, lungs, stomach, and the like.

The present systems provide access to a target structure from or through the patient's skin. In other words, a working area is created in proximity to a target structure by providing a direct access path from the patient's skin to the target structure. The present systems are structured to dilate soft tissue located between the skin and the target structure. The soft tissue deforms around a portion of the tissue dilation system, which is typically rigid in construction, to achieve the desired dilation effects. Importantly, sufficient dilation of the tissue can be achieved with the present systems with reduced trauma relative to cutting procedures which cut soft tissue. In certain embodiments, the dilation tubes are inserted through an incision in the skin and the fascia, or just the skin. In other embodiments, no incision may be necessary.

Generally, the present tissue dilation systems comprise a plurality of tissue dilation tubes that are telescopically arranged. For example, a tissue dilation system typically comprises a first dilation tube and a second dilation tube. The second dilation tube has a lumen sized or dimensioned to accommodate at least a portion of the first dilation tube. The tissue dilation systems can comprise more than two dilation tubes. For example, the present systems can comprise three, four, five, six, or more dilation tubes, as desired. The dilation tubes are telescopically arranged so that at least a portion of the first dilation tube is located in a lumen of the second dilation tube, and at least a portion of the second dilation tube is located in a lumen of the third dilation tube, etc.

The present systems include a dilation tube retention assembly or a locking assembly. The dilation tube retention assembly is effective in retaining one or more dilation tubes in a substantially fixed position relative to one or more of the other dilation tubes. As used herein, a substantially fixed position refers to a position in which one dilation tube cannot freely move along the entire length of another dilation tube. For example, as discussed herein, a dilation tube may be retained in a substantially fixed position and still rotate about the tube's central longitudinal axis relative to another dilation tube. In addition, a dilation tube may be able to be moved slightly along its longitudinal axis relative to another dilation tube, such as by distances of less than seven inches, less than five, less than four, less than three, less than two inches, or less than one inch, or less than one centimeter, and still be retained in a substantially fixed position. Such numerical values will likely be associated with the length of dilation tubes, and are provided by way of example and not by way of limitation. Thus, tissue dilation tubes may be held in a substantially fixed position so that the combination of dilation tubes in a substantially fixed position or in a locked configuration results in a single tissue dilation system or device.

As used herein, the tissue dilation systems may also be referred to as dilation introducers, tissue dilation introducers, tissue dilation devices, and tissue dilation apparatuses. These terms are used interchangeably and are used in reference to systems which comprise a plurality of (two or more) tissue dilation tubes or dilator tubes, as discussed herein.

In one embodiment, a tissue dilation system comprises a first dilation tube, a second dilation tube, and a dilation tube retention assembly. The first dilation tube has a proximal end and a distal end. The second dilation tube has a proximal end and a distal end, and also has a lumen or bore extending from the proximal end to the distal end. The lumen of the second dilation tube is dimensioned, such as sized and shaped, to accommodate at least a portion of the first dilation tube. In certain embodiments, the lumen of the second dilation tube is dimensioned to accommodate a major portion, such as 50% or more, of the first dilation tube. However, other embodiments may be dimensioned to accommodate a minor portion or less than 50% of the first dilation tube. In further embodiments, the second dilation tube lumen can accommodate substantially all of the first dilation tube. Thus, in a two-dilation tube tissue dilation system, the second dilation tube can be understood to be the outermost dilation tube. The second dilation tube can also be understood to be the dilation tube having the largest outer cross-sectional distance, such as the largest outer diameter. In a three-dilation tube tissue dilation system, the third dilation tube can be understood to be the outermost dilation tube. In a four-dilation tube tissue dilation system, the fourth dilation tube can be understood to be the outermost dilation tube. The same relationship can be applied to tissue dilation systems that comprise more than four tissue dilation tubes. The first dilation tube can have a lumen extending from the proximal end to the distal end of the first dilation tube. For example, the first dilation tube can be referred to as a cannulated first dilation tube. Alternatively, the first dilation tube can have a solid body with no longitudinal lumen.

The illustrated tissue dilation tubes are shown as having a substantially straight longitudinal axis or straight body.

Addition dilation tubes in accordance with the disclosure herein may be non-linear or curved. For example, the present tissue dilation systems may comprise one or more non-linear or curved tissue dilation tubes.

Although the tissue dilation tubes disclosed herein are illustrated as having circular cross-sections, and therefore may be understood to be substantially cylindrical tubes, other tissue dilation tubes of the present systems may have non-circular shaped cross-sections. For example, one or more dilation tubes may have one or more straight edges when viewed in cross-section. Thus, the present dilation systems may comprise dilation tubes that have triangular, rectangular, square, pentagonal, hexagonal, octagonal, and other geometric shapes. In certain embodiments, such as the illustrated embodiments, the dilation tubes have substantially identical or entirely identical cross-sectional shapes, and only have different sizes. For example, the illustrated dilation tubes have circular cross-sectional shapes and have different outer diameters and/or different inner diameters.

The dilation tube retention assembly of the tissue dilation system is effective in retaining the second dilation tube, in the embodiment described above, in a substantially fixed position relative to the first dilation tube prior to the use of the tissue dilation system to dilate tissue of the individual. Thus, the dilation tube retention assembly may also be understood to be a dilation tube fixation assembly, or a locking assembly in certain embodiments. The retention assembly may also be understood to be means for connecting the first dilation tube and the second dilation tube in a locked or substantially locked configuration. The dilation tube retention assembly is also effective in releasing the second dilation tube from the substantially fixed position to facilitate movement of the second dilation tube towards the distal end of the first dilation tube to dilate tissue of the individual. When the retention assembly is released, the second dilation tube can move along the length of the first dilation tube so that the distal end of the second dilation tube is adjacent or in proximity to the distal end of the first dilation tube. By releasing the retention assembly, it is possible to distally advance or distally move the outer dilation tubes relative to the first dilation tube to effectively dilate tissue of the patient. The serial dilation of the tissue using the present tissue dilation systems provides reduced trauma relative to other surgical methods of creating work spaces, such as cutting tissue and the like, and is relatively easy to achieve in a reduced amount of time compared to systems which use separate dilation tubes that are not preassembled into a single system or device.

As disclosed herein, various embodiments of the present systems include tissue dilation tube retention assemblies of different structures and configurations. The dilation tube retention assemblies are able to maintain the dilation tubes in a substantially fixed position relative to each other, and may achieve this arrangement using one or more mechanical fasteners and/or pressure provided by a person's hand. In certain embodiments, a retention assembly is engageable with the first dilation tube, the second dilation tube, or a combination of the first dilation tube and the second dilation tube to maintain the second dilation tube in a locked configuration relative to the first dilation tube, and to release the second dilation tube into an unlocked configuration to facilitate distal advancement of the second dilation tube along the first dilation tube.

As discussed herein, the first dilation tube and the second dilation tube can be preassembled in a locked configuration prior to dilation of the tissue of the patient. When the tissue dilation system comprises a third dilation tube, the dilation tube retention assembly can retain the third dilation tube in a substantially fixed position relative to either the first dilation tube, the second dilation tube, or both. In certain embodiments, the third dilation tube can be held in a locked configuration relative to the second dilation tube, but can be in an unlocked configuration relative to the first dilation tube, such as when the second dilation tube is urged into an unlocked configuration relative to the first dilation tube.

In certain embodiments, such as FIGS. 1-7B as discussed herein, the dilation tube retention assembly comprises at least one locking clip. The locking clip can be removably connected to the first dilation tube, the second dilation tube, or both the first and second dilation tube. The locking clip may engage with spaced apart rings to provide the desired locking engagement.

In other embodiments, such as FIGS. 8-12, 30-65, and 68-71, as discussed herein, the dilation tube retention assembly comprises one or more locking pins or one or more buttons engageable with either the first dilation tube, the second dilation tube, or both. The locking pins or buttons may cooperatively work with a latching member or may employ other mechanisms for obtaining the desired retention or fixation, as discussed herein.

In further embodiments, such as FIGS. 13-18, the dilation tube retention assembly comprises a plurality of bayonet pins or slots extending from an outer surface of the dilation tube. The bayonet pins interact with bayonet pin receptacles to retain the dilation tubes in a substantially fixed position. The combination of bayonet pins and bayonet pin receptacles may be understood to be a bayonet fitting.

In yet another embodiment, such as the embodiment of FIGS. 19-23, the dilation tube retention assembly comprises a handle that is effective in urging the dilation system from a substantially fixed or locked configuration to an unlocked or unfixed configuration. The handle may have a length that is not parallel to the length of the dilation tubes. For example, the handle may extend in opposite directions at a perpendicular angle to the longitudinal axis of the dilation tubes. The handle may be provided as an integral portion of the second dilation tube, and may include a receptacle to receive a pin extending from the proximal end portion of the first dilation tube. The proximal end of the first dilation tube may include a grip which can abut a person's palm. In this embodiment, the retention of the second dilation tube and the first dilation tube in a substantially fixed position can be achieved solely by a person applying a gripping force to the handle and the grip, or by a mechanical interaction of the pin and receptacle, or a combination thereof. Further details will become apparent from the disclosure herein.

The present systems may also comprise a guide wire. In certain embodiments, the guide wire extends from the distal end of the first dilation tube. It may be desirable in such embodiments to construct the first dilation tube to have a lumen or bore extending from the proximal end to the distal end to accommodate the guide wire. Other embodiments may not require such a lumen and can cooperate with the guide wire to provide the desired positioning of the dilation tubes in the patient. The guide wire can be helpful in positioning the dilation tubes in proximity to a target structure, such as a bone surface including vertebral and hip surfaces. However, guide wires may also be useful in positioning the dilation tubes in proximity to target structures that are less rigid than bone. Guide wires may be a component of the present systems, and may be inserted prior to insertion of the dilation tubes of the present systems into the patient. Thus, as understood by persons of ordinary skill in the art, a guide wire may be inserted through the skin or through an incision formed in the skin of a patient, and advanced in proximity to a target structure. The dilation tubes of the present systems may then be placed over a portion of the guide wire, such as a proximal portion of the guide wire, and then distally advanced toward the target structure by dilating the tissue.

In certain embodiments, as shown in FIGS. 27-29, the distal end of the guide wire may have an enlarged distal end region relative to a more proximal region of the guide wire. For example, the distal end region of the guide wire may have a maximal cross-sectional distance greater than a maximal cross-sectional distance of a proximal region of the guide wire. Or, the distal end region of the guide wire may have a maximal cross-sectional area that is greater than a maximal cross-sectional area of a more proximal region of the guide wire. The guide wire with an enlarged distal end may be particularly useful in reducing or preventing damage to soft target structures by the dilation tubes and/or other components of the tissue dilation systems. Thus, the enlarged distal end can be understood to be a stop device that prevents further distal movement of a dilation tube over the guide wire.

Figures 32, 33:
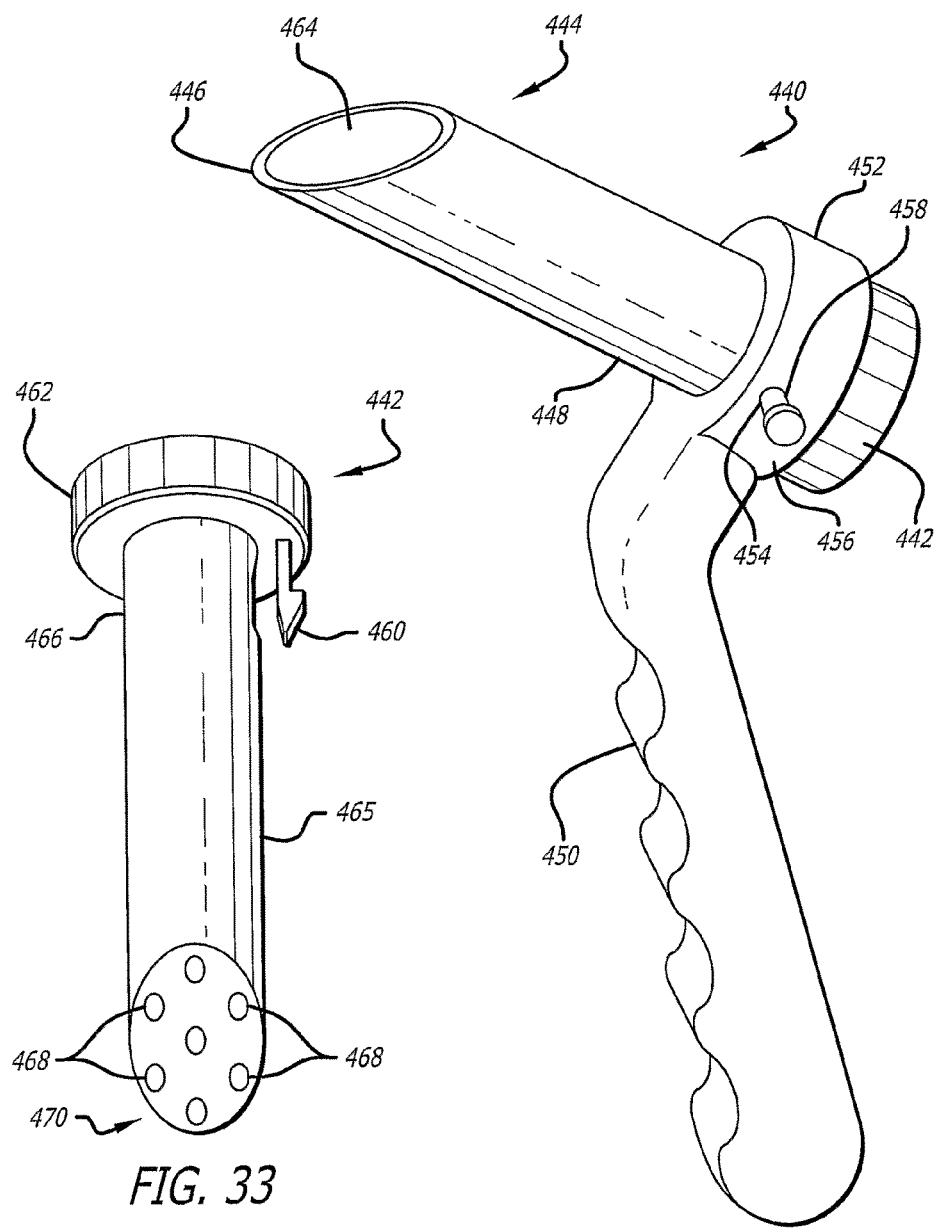
FIG. 32 is a perspective view of a variation of the outer dilator tube of the embodiment of FIGS. 8-12, with an angled tip and with a parallel guide.
FIG. 33 is a perspective view of the parallel guide with an angled tip from FIG. 32.

Embodiments of the present tissue dilation systems which include one or more guide wires may also comprise a guide wire insert, such as shown in FIGS. 30-33, and as discussed herein. The guide wire inserts are dimensioned to be inserted into the dilation tube having the largest lumen. For example, the guide wire inserts are dimensioned to be inserted into the outermost dilation tube of the present systems. The guide wire inserts disclosed herein can comprise a plurality of longitudinal bores effective in directing a plurality of guide wires parallel to each other from the tissue dilation system. These guide wire inserts may be referred to as parallel guide wire inserts. Other guide wire inserts can comprise a plurality of longitudinal bores that can accommodate guide wires that are oriented non-parallel to each other. For example, such bores may diverge toward the distal end or converge toward the distal end. The guide wire insert may have a distal end configured to matingly engage with a bone surface of the patient. For example, the distal end of the guide wire insert may be configured to contact a bone surface at a desired angle, which may be related to the orientation in which the tissue dilation system approaches the bone surface. In certain embodiments, the distal end will have a specific configuration for a specific bone surface. For example, as shown in FIG. 33, the distal end can be beveled to facilitate the positioning of the guide wires relative to a surface of a hip of a human patient. In addition, the distal end of the guide wire insert may also have a distal end surface that is non-planar. For example, the distal end surface may have a convex surface or a concave surface depending on the physical structure of the target structure. The guide wire inserts of the present systems may comprise a locking device effective in retaining the guide wire insert in a locked configuration relative to the dilation tube in which the insert is placed.

Additional embodiments, as disclosed herein, may include an illumination source, such as one or more light emitting diodes (LEDs) or one or more optic fibers, or combinations thereof, that are effective in illuminating a region in proximity to the distal end of the tissue dilation system.

Further embodiments of the present systems may comprise an imaging system effective in imaging an area in proximity to the distal end of the tissue dilation system. The imaging system may also be configured to transmit an acquired image to a remote location for viewing.

In certain embodiments of the present systems, the systems comprise a handle having a hand grip portion and a dilation tube receiving portion at one of the handle. Thus, the handle can be attached to a dilation tube of the present dilation systems. In other embodiments, the handle can be integrally formed with one of the dilation tubes. The handle can have a hand grip portion located away from the longitudinal axis of the dilation tube. A handle of the present systems may also be lockingly engaged with the dilation tube having the largest cross-sectional diameter.

In certain embodiments of the present systems, one or more of the dilation tubes can have a beveled distal end surface. Beveled surfaces may be helpful in facilitating advancement of the dilation tubes through soft tissue without substantially damaging the soft tissue. Furthermore, beveled surfaces may help reduce trauma that may be associated with advancing the tissue dilation tubes through the tissue.

In further embodiments, the distal end of the dilation tubes may have a smaller maximum cross-sectional distance compared to a more proximal portion of the dilation tube. For example, the dilation tubes may be tapered along their length. As shown in the illustrated embodiments, the taper of the dilation tubes may be limited to a distal end region of the dilation tube. In other embodiments, the taper may be more gradual, and may extend from the distal end to a midpoint region of the dilation tube, or may be substantially tapered from the distal end to the proximal end.

The present systems may also include a bone drill effective in drilling bone in proximity to the dilated tissue of the patient. The bone drill may include a bit that extends from the distal end of the dilation tube, and a body that extends through the dilation tube. Bone drills may be particularly useful in procedures such as implanting bone anchors and the like into a bone structure, including vertebrae and hips. As shown in FIG. 5A the bone drill may extend from or through the outermost dilation tube, such as the third dilation tube illustrated in FIG. 5A. In embodiments with two dilation tubes, the bone drill can extend through the second dilation tube. In embodiments with four dilation tubes, the bone drill can extend through the fourth dilation tube.

The present systems may also comprise a visualization agent, as discussed herein, which may be effective in permitting visualization of the distal end of the dilation tube in the patient. For example, the systems may comprise one or more radiopaque markers that can be visualized using conventional imaging techniques. Radiopaque markers or other visualization agents may be provided at one or more regions of the tissue dilation tubes. For example, radiopaque markers can be provided at the distal ends of the tissue dilation tubes, at two or more discrete regions along the length of the tissue dilation tubes, or may even be provided along the entire length of the tissue dilation tube. The visualization agents can be integrally provided in the body of the tissue dilation tube, or may be provided as a coating on a tissue dilation tube or tubes. The coating can be permanently affixed to a surface of a tissue dilation tube, or can be removably attached to a surface of the tissue dilation tube.

Figure 36A:
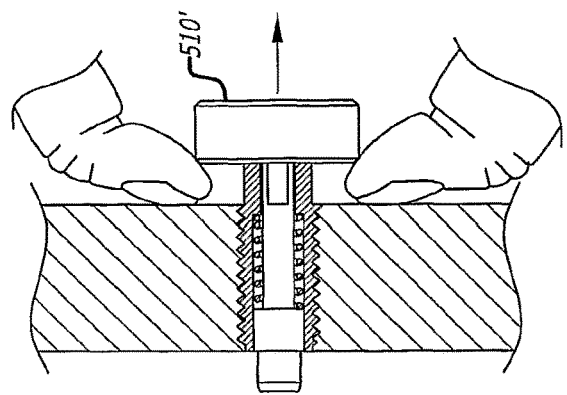
FIG. 36A is a partial sectional view of a latching button of the present systems.

In embodiments of the present systems which include a button or pin, the dilation tubes may include one or more recesses, grooves or apertures which can be engageable with a portion of the button or pin to facilitate retaining the dilation tubes in a substantially fixed position. The recesses extend from an outer surface of a dilation tube toward the interior of the dilation tube, such as toward the lumen of the dilation tube. In certain embodiments, the dilation tubes may comprise one or more circumferential grooves that do not contact the lumen of the dilation tube. Other embodiments may include one or more holes to the lumen. When more than one button or pin is provided, typically, the present systems will comprise an equal number of recesses or apertures to engage with the buttons or pins. The buttons or pins may be biased in a desired configuration. For example, the buttons or pins may be provided in combination with a biasing member effective in urging the button away from the body of the tissue dilation system in the locked configuration. The button can be depressed to unlock a dilation tube. In other embodiments, the button can be biased toward the body of the tissue dilation system and the button can be pulled out to unlock the dilation tube, such as shown in FIG. 36A. Thus, the present systems can include buttons or pins that are biased to a locked configuration and require force to urge them into an unlocked configuration.

Certain embodiments, such as those illustrated in FIGS. 76-78, may comprise an expander sleeve that is effective in dilating or expanding tissue located in proximity to the distal end of the dilation tube. For example, an expander sleeve may be provided on the distal end region of the outermost dilation tube. The expander sleeve increases the working area in proximity to a target structure relative to the area provided by the outermost dilation tubes. The expander sleeve may also be effective in preventing or reducing dilated tissue from moving or "falling" back into the working area when the outermost dilation tube is present.

In at least one specific embodiment, a tissue dilation system comprises at least three dilation tubes telescopically arranged relative to each other, and a handle coupled to the dilation tube having the largest cross-sectional diameter. For example, the tissue dilation tube comprises a first dilation tube, a second dilation tube, and a third dilation tube, and a dilation tube retention assembly, as discussed herein. In addition, the handle can be integrally formed with the third dilation tube. For example, the handle can be integrally formed with a proximal end of the third dilation tube. In this embodiment, the second dilation tube and the third dilation tube can have equal or substantially equal lengths. This is in contrast to other dilation tube systems which require the use of multiple dilation tubes all of different lengths. In other embodiments, the third dilation tube is shorter than the second dilation tube, and the second dilation tube is shorter than the first dilation tube. In this embodiment, the dilation tube retention assembly can comprise a plurality of spring loaded locking pins which engage the dilation tubes.

Additional embodiments of the present systems can comprise a plurality of tissue dilation tubes all having equal or substantially equal lengths. Alternatively, a tissue dilation system can comprise three or more dilation tubes, wherein the second tube and/or third tube are longer than first dilation tube.

In further embodiments, the second dilation tube may have a proximal end that extends beyond the handle. In other words, the handle that is attached to the third dilation tube may be distally located relative to the proximal end of the second dilation tube. If latching buttons are provided, they can be provided at a proximal region relative to the handle. In addition, for handles that are not integrally formed with the dilation tube, an anti-rotation member effective in reducing or preventing rotation of the handle relative to the dilation tube, such as the second dilation tube, may be provided.

As described herein, the components of the present systems can be assembled together to form a single device or apparatus effective in dilating tissue of a patient. Thus, the system can be understood to be a preassembled device comprising a plurality of dilation tubes. The present systems can be provided as a sterile preassembled system prior to being placed in an operating room. Alternatively, the components of the present system can be provided in a sterile condition, such as in a sterile package or packages and assembled in the operating room before use in a patient.

In addition, the present systems or components thereof may be reusable or disposable. For example, a reusable system may comprise one or more components that can be sterilized and packaged for additional medical procedures. Disposable systems or components can be discarded after a single use.

Accordingly, a method of producing a telescopic tissue dilation system is encompassed by the present invention. In one embodiment, such a method comprises inserting a first dilation tube into a lumen of a second dilation tube, and retaining the first dilation tube and the second dilation tube in a substantially fixed position. In this substantially fixed position, the system can be used to dilate a patient's tissue. The method may comprise an additional step of placing the combination of the first dilation tube and the second dilation tube into a lumen of a third dilation tube. For example, the third dilation tube can be placed over the combination of the first and second dilation tube, or the combination of the first dilation tube and the second dilation tube can be inserted into the lumen of the third dilation tube.

The components of the present systems are formed from materials that are medically acceptable. For example, the materials may be surgical grade materials, such as plastics, metals, such as stainless steel, and the like, and combinations thereof. The components are substantially rigid. In other words, the dilation tubes are generally not flexible or not malleable. It can be understood that the guide wire or similar guiding device used to guide the dilation tubes may be more flexible or malleable relative to the dilation tubes. Alternatively, a guide wire can be as rigid or more rigid than the tissue dilation tubes, and provide sufficient structural support to guide the tubes towards a target structure.

The materials of the present systems can be readily sterilized and packaged ready for use, after which the dilation introducer may be disposed of or resterilized for subsequent use, as desired. The dilator tubes may be radioluscent, with radiopaque markers located on or at the tips of one or more of the dilator tubes. Radiopaque material, including Barium Sulfide or Bismuth Subcarbonate may be added to polymers to make any of the components of the dilation introducer system to have a desired degree of radiopacity. The tip of the first dilator and/or other dilators may also be scored, grooved, or otherwise be provided with a rough surface, to prevent migration. The dilation introducer may also have curved or otherwise non-linear dilator tubes, and the dilation introducer may also have a non-cylindrical shape, such as an oval shape, for example, to allow the dilation introducer to be inserted around objects or a patient's organs.

The method of producing the present systems may also comprise steps of engaging one or more locking devices to retain the dilation tubes in a locked configuration, as discussed herein.

The present systems can be used to dilate a variety of tissues of a patient. For example, the systems can be used to dilate one or more soft tissue structures that are located between the skin and a target structure. Thus, a method of dilating tissue of a patient can comprise placing a portion of a first dilation tube of a telescopic tissue dilation system adjacent or against a tissue region of a patient to provide dilation of tissue around the first dilation tube, and advancing a second dilation tube of the system into the patient towards a target structure to provide dilation of tissue around the second dilation tube. The second dilation tube can be urged into an unlocked or unfixed configuration before advancing the second dilation tube into the patient towards the target structure. Because the second dilation tube has a greater outer diameter compared to the first dilation tube, the second dilation tube can provide greater dilation of the tissue compared to the dilation of the tissue around the first dilation tube. The method can also comprise a step of advancing a third dilation tube to further dilate the tissue.

As discussed herein, the dilation tubes can be used in combination with a guide wire. Thus, a method can comprise inserting a guide wire insert or guide wire guide into one of the dilation tubes. In certain embodiments, such as when the systems are used to provide access to a region or regions of a hip, the guide wire guide has a beveled distal end surface, and the method can comprise a step of placing the beveled distal end surface against a bone surface, such as a region of the hip, so that the beveled distal end surface is flush with the bone surface. As discussed herein, the beveled distal end surface can be concave.

Other embodiments of the method can comprise one or more additional steps, such as a step of drilling bone contacted by or in proximity to the tissue dilation system, or a step of imaging an area in proximity to the distal end of the tissue dilation system or a distal end of a dilation tube of the system.

Reference will now be made in detail to the presently illustrated embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, front, backward, forward, distal and proximal are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims.

As shown in FIG. 1, a telescoping dilation introducer or tissue dilation system for surgery is illustrated. In this embodiment, the dilation introducer has a locked assembled configuration for initial placement of the dilation introducer against a patient's tissue to be dilated, and an unlocked or unfixed, collapsed configuration dilating the patient's soft tissue down to the bone tissue or other target tissue to be treated to a desired degree of dilation to permit minimally invasive surgical procedures on the patient's bone tissue or target tissue.

As described herein, the present systems can be used in practicing a variety of medical procedures which require or may benefit from tissue dilation. For example, the present systems may be used alone or in combination with other medical devices for orthopedic surgery. In certain embodiments, the systems are structured and used in spinal fusion procedures, such as in combination with procedures utilizing bone anchors, bone plates, cages, and the like. In other embodiments, the systems are structured and used in hip surgeries. In yet other embodiments, the systems are used in arm, shoulder, knee, leg, or other thoracic surgeries, lumbar procedures, cervical procedures, and the like. Thus, the present systems may be used in minimally invasive procedures, where progressive dilatation of soft tissue is desirable for exposure of target structures in a patient's body. The dilation introducer can be brought up against other firm or solid structures in the body or introduced into the body to thereby gain the advantages of the invention for other minimally invasive procedures.

Figure 2:
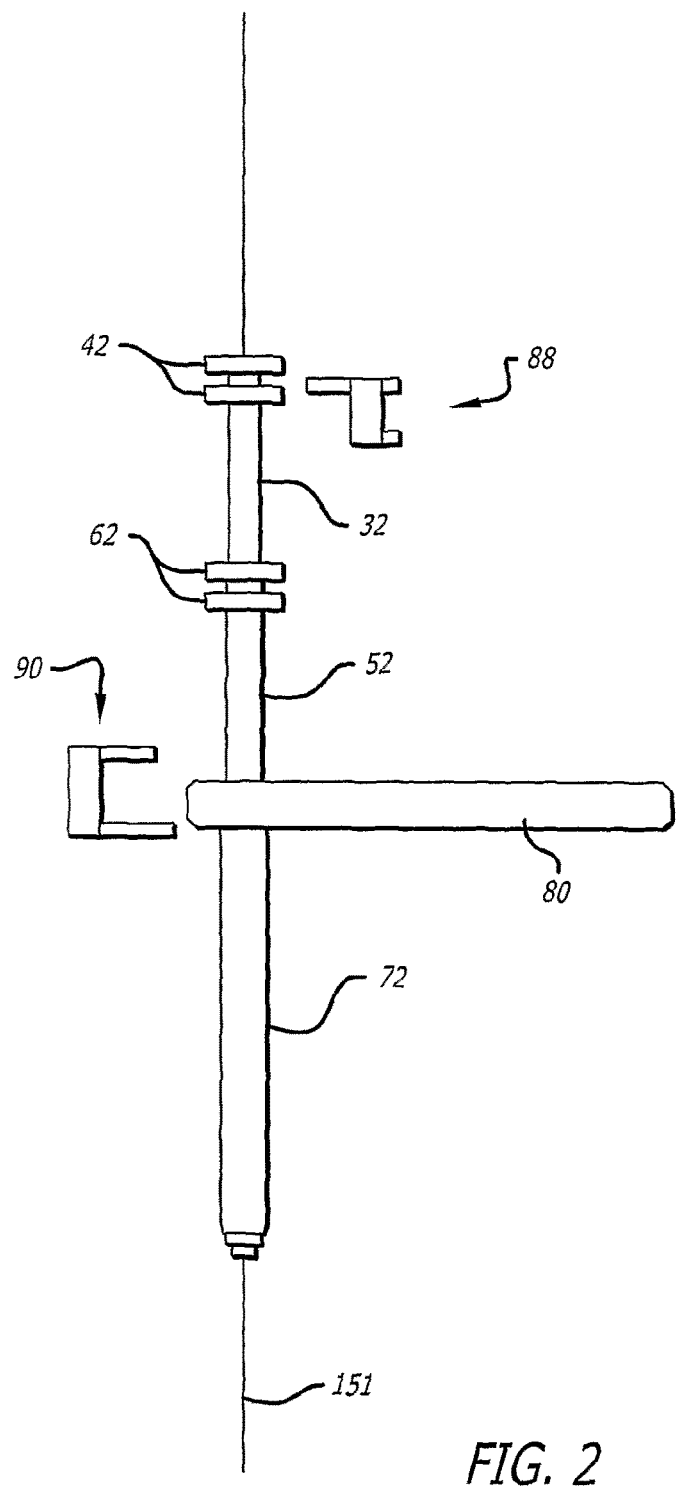
FIG. 2 is a plan view of the dilation introducer of FIG. 1 shown in an unlocked, collapsed configuration.

A dilation introducer 30 according to a first embodiment is shown in a locked assembled configuration or in a substantially fixed position in FIG. 1, and shown in an unlocked, collapsed configuration in FIG. 2. In FIG. 1, the dilation introducer comprises a first or inner dilator tube 32, a second dilator tube 52, and a third dilator tube 72. In this embodiment, the second dilator tube 52 is shorter than the first dilator tube 32 and has a lumen to accommodate the first dilator tube 32. Furthermore, the third dilator tube 72 is shorter than the second dilator tube 52 and has a lumen to accommodate the second dilator tube 52. As discussed herein, the second and third dilator tubes may have the same length, if desired. The introducer also comprises a handle 80 which is in contact with the outer or third dilator tube 72. The introducer also comprises a dilation tube retention assembly which is illustrated as comprising first and second locking clips 88 and 90, respectively, as discussed herein. A guide pin, guide wire or K wire 151 is illustrated as extending from the distal end 34 of the first dilator tube 32.

In more detail, and referring to FIG. 3, the dilation introducer includes a first or inner dilator tube 32 having a distal end 34 with a tapered tip 36, and a proximal end 38 with a head 40 including a pair of spaced part rings 42. The first dilator tube has an inner lumen 44 with a distal opening 46 and a proximal opening 48.

Referring to FIG. 4, the dilation introducer also includes a shorter second or intermediate dilator tube 52 having a distal end 54 with a tapered tip 56, and a proximal end 58 with a head 60 including a pair of spaced apart rings 62. The second dilator tube has an inner lumen 64 with a distal opening 66 and a proximal opening 68.

Referring to FIG. 5, the dilation introducer also includes an additional dilator tube, such as a still shorter third or outer dilator tube 72 having a distal end 74 with a tapered tip 76, and a proximal end 78 with a handle 80. The third dilator tube has an inner lumen 82 with a distal opening 84 and a proximal opening 86.

Embodiments with an outer dilator tube 72 having a tapered tip 76 can be beneficial where careful splitting of soft tissues is desirable, for example to avoid bleeding or damage to muscle fibers, and the distal end 74 of the dilator tube 72 will rest against a relatively flat hard tissue structure. Because the distal opening 84 of the distal dilator tube 72 is at a substantially perpendicular axis to the central longitudinal axis of the outer dilator tube 72, the tapered tip 76 will be able to fit flat against a hard tissue and substantially exclude soft tissues from the distal opening 84. Soft tissue will not slide under the distal end 74 of the dilator tube 72 and obscure the surgeons line of sight or access to the underlying target structure. Therefore, embodiments including this configuration of tapered tip 76 would be particularly beneficial when the surgical approach is generally at a perpendicular angle to a substantially flat bone surface. Examples of this would be a posterior approach to a lower lumbar spinal lamina for microdiscectomy, or a posterior approach to the cervical lamina and facet for a foraminotomy. As discussed herein, non-perpendicular angled distal end surfaces may be useful when the surgical approach is at a non-perpendicular angle to the target structure or a surface thereof. For example, when the system is used to provide an access path to a portion or region of a hip of a patient.

Figure 6A:
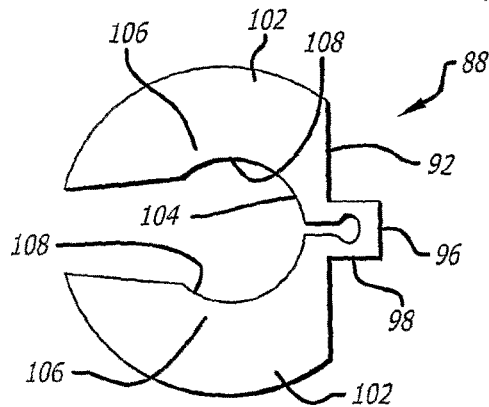
FIG. 6A is a top plan view of the first locking clip of the dilation introducer of FIG. 1.
Figure 6B:
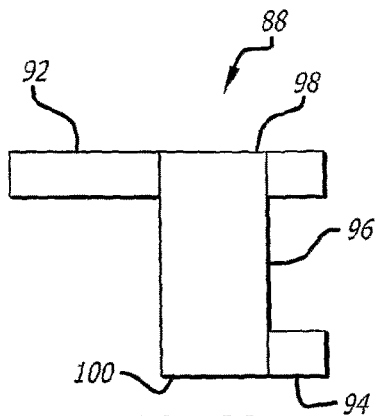
FIG. 6B is an elevational view of the first locking clip of the dilation introducer of FIG. 1.
Figure 6C:
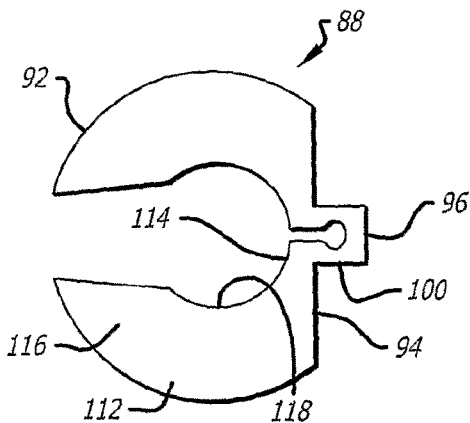
FIG. 6C is a bottom plan view of the first locking clip of the dilation introducer of FIG. 1.
Figure 7A:
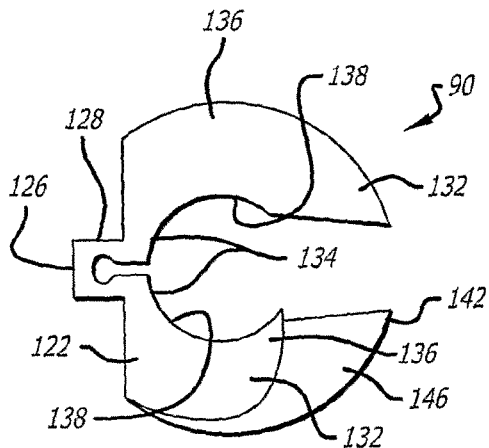
FIG. 7A is a top plan view of the second locking clip of the dilation introducer of FIG. 1.
Figure 7B:
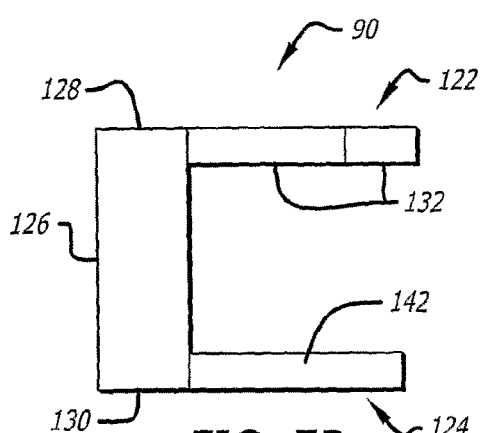
FIG. 7B is an elevational view of the second locking clip of the dilation introducer of FIG. 1.

Referring to FIGS. 6A, 6B and 6C, means for removably connecting the first and second dilator tubes together in a locked configuration includes a first locking clip 88. As is shown in FIGS. 7A and 7B, means for removably connecting the second and third dilator tubes together in a locked configuration may also be provided, and may include a second locking clip 90. The first locking clip includes a first portion 92 and a second portion 94, and a cross-piece or handle 96 having a first end 98 and a second end 100 connected at right angles between the first and second portions. The first portion includes pair of resilient arms 102 each having a proximal narrow neck portion 104 connected to the cross-piece, and a distal gripping portion 106 extending from the narrow neck portion. The resilient arms have an inner rounded surface 108 adapted to snap over the first dilator tube between the spaced apart rings of the first dilator tube. The second portion currently preferably includes a single arm 112 having a proximal narrow neck portion 114, and a distal gripping portion 116 extending from the narrow neck portion. The gripping portion has an inner rounded surface 118 adapted to fit over the outer surface of the second dilator tube between the spaced apart rings of the second dilator tube, to connect the first and second dilator tubes. Removing the first locking clip allows the second or intermediate dilator tube to slidably telescope over the first inner dilator tube to dilate tissue at the distal end of the dilation introducer.

The second locking clip includes a first portion 122 and a second portion 124, and a cross-piece or handle 126 having a first end 128 and a second end 130 connected between the first portion and the second portion at right angles. The first portion includes a pair of resilient arms 132 each having a proximal narrow neck portion 134 connected to the cross-piece, and a distal gripping portion 136 extending from the narrow neck portion. The pair of resilient arms have an inner rounded surface 138 adapted to snap over the outer surface of the second dilator tube between the spaced apart rings of the second dilator tube. The second portion of the second locking clip includes a pair of resilient arms 142 each having a proximal narrow neck portion (not shown) connected to the cross-piece and a distal gripping portion 146 extending from the narrow neck portion, the pair of resilient arms having an inner rounded surface (not shown) adapted to fit over the outer surface of the third dilator tube to connect the second and third dilator tubes. Removing the second locking clip allows the third or outer dilator tube to slidably telescope over the second inner dilator tube to further dilate tissue at the distal end of the dilation introducer.

As is shown in FIG. 5A, a tubular bone drill or tap 150 can be inserted through a dilator tube to contact the surface of the vertebra, hip, or other bone, or other target structure to be treated, as further described herein. In FIG. 5A, the bone drill 150 is extending from the distal end of the third dilator tube. A portion of the bone drill 150 is also extending from the proximal end of the third dilator tube. Similarly, the bone drill can be inserted through an intermediate dilator tube, such as the second dilator tube shown in FIG. 1. Once the outer dilator tube has been moved to the distal end of the dilation introducer into position against a surface of the target structure, such as a portion of the vertebra or bone to be treated to fully dilate the soft tissue, the inner dilator tube, the tubular bone drill, and the intermediate dilator tube can be withdrawn and removed to leave the outer dilator tube in place to provide an access path or working area to permit further surgical procedures near or of the target structure.

Figure 8:
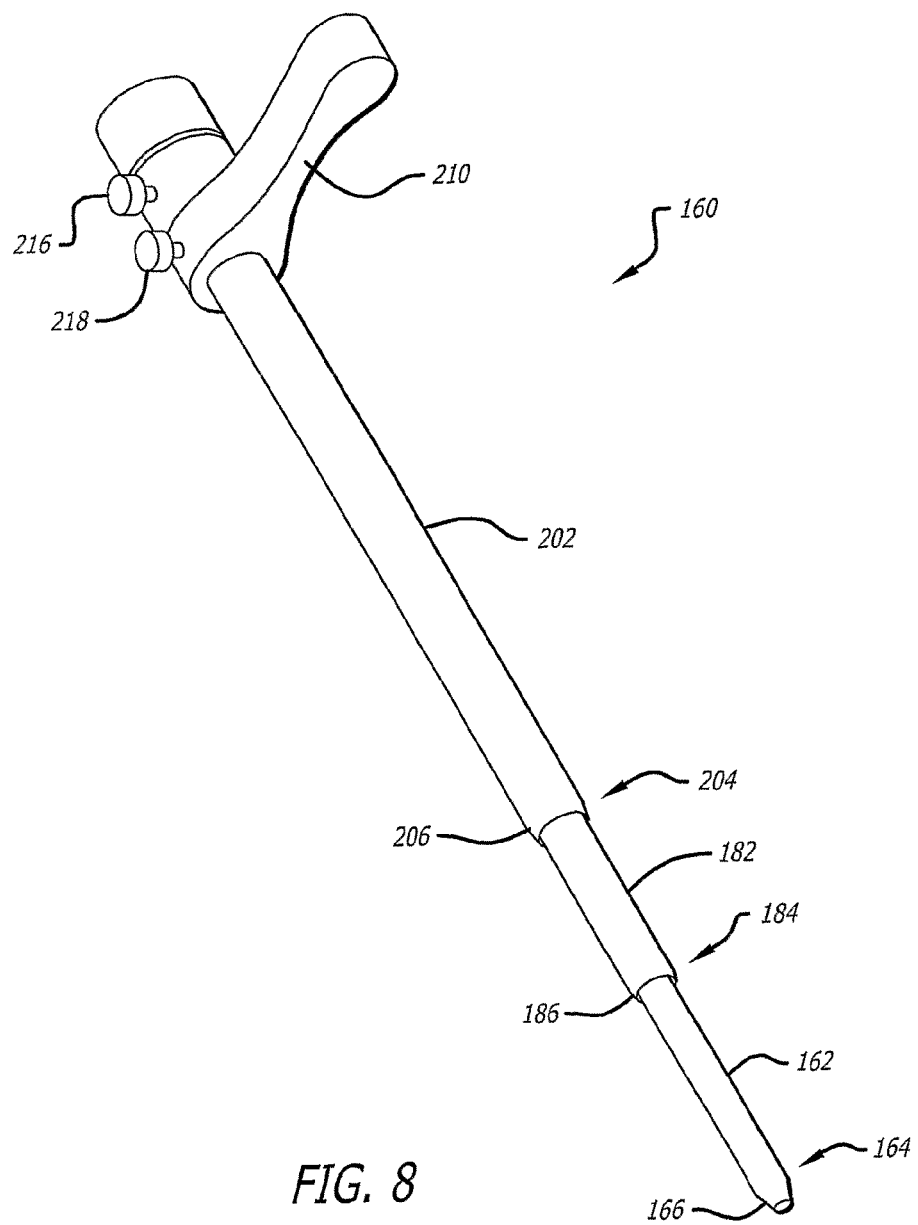
FIG. 8 is a perspective view of a second embodiment of a dilation introducer in a locked configuration, according to the present invention.
Figure 9:
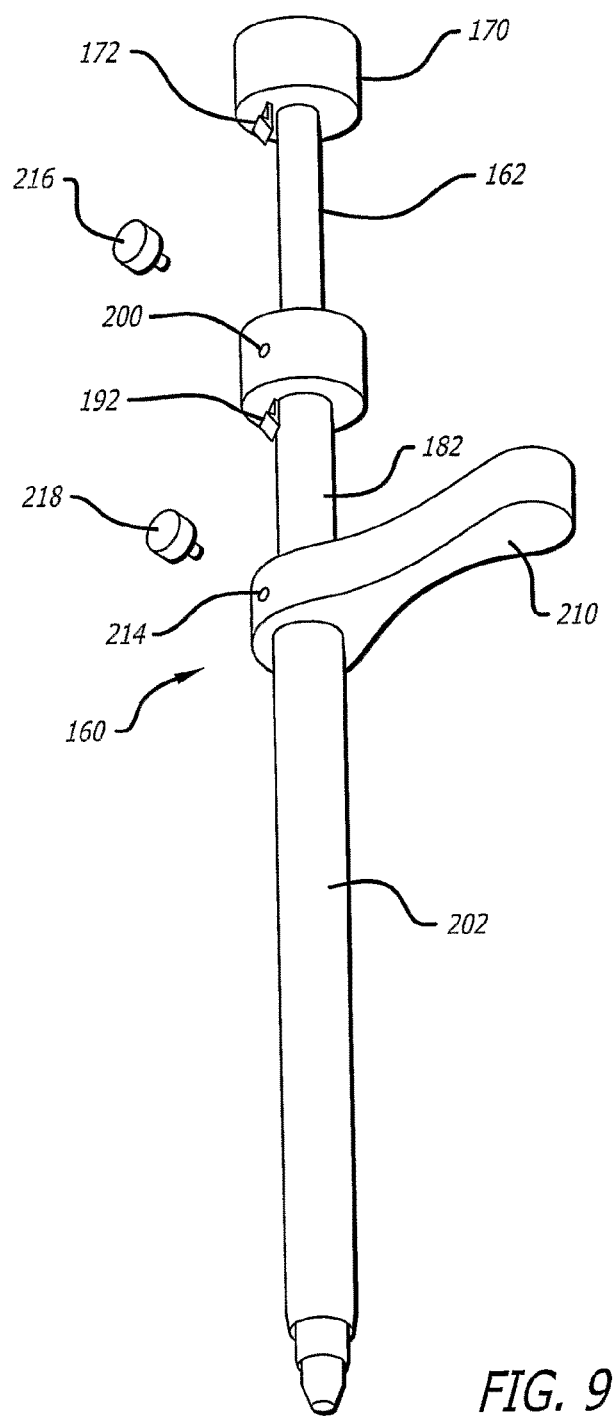
FIG. 9 is a perspective view of the dilation introducer of FIG. 8 shown in an unlocked, collapsed configuration.

Referring to FIGS. 8-12, a dilation introducer 160 is shown in a locked assembled configuration in FIG. 8, and shown in an unlocked, collapsed configuration in FIG. 9. Referring to FIG. 10, the dilation introducer includes a first or inner dilator tube 162 having a distal end 164 with a tapered tip 166, and a proximal end 168 with a cylindrical head 170. The means for removably connecting the first and second dilator tubes together in a locked configuration includes a latching member 172, such as a hook, projecting from the cylindrical head toward the distal end, receiving a locking pin 216, although other latching members, such as a projection with an aperture for receiving a locking pin may also be suitable, as will be apparent from the explanation below. The first dilator tube has an inner lumen 174 with a distal opening 176 and a proximal opening 178.

Referring to FIG. 11, the dilation introducer includes a shorter second or intermediate dilator tube 182 having a distal end 184 with a tapered tip 186, and a proximal end 188 having a cylindrical head 190. Means for removably connecting the second and third dilator tubes together in a locked configuration includes a latching member 192, such as a hook, projecting from the cylindrical head toward the distal end, receiving a locking pin 218, although other latching members, such as a projection with aperture for receiving a locking pin may also be suitable, as noted above. The second dilator tube has an inner lumen 194 with a distal opening 196, and a proximal opening 198. The cylindrical head includes a first radial aperture 200 for receiving the locking pin 216, and a second longitudinal aperture 201 for receiving the distally projecting latching member of the cylindrical head of the first or inner dilator tube.

The locking pins in the embodiment illustrated in FIGS. 8-12 can be used to unlock the latching members by pushing on the latching member. For example, the locking pin can be pushed by a person's finger to depress the latching member and disengage the hook portion from a mating surface of the dilation tube. Alternatively, if the locking pin is configured to act as the mating surface which the hook portion of the latching member contacts, the locking pin can be pulled out or away from the latching member to disengage the latching member and unlock the dilation tube.

Figure 12:
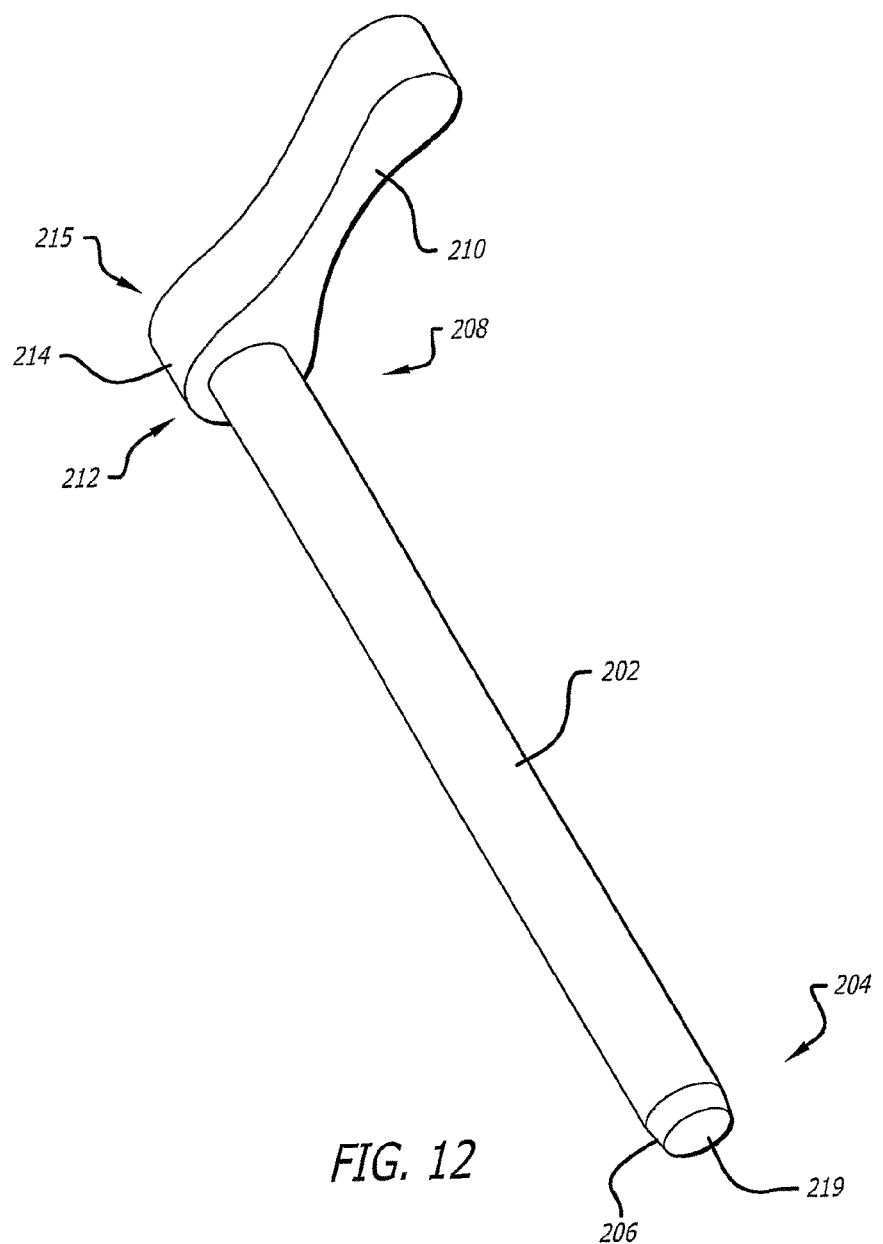
FIG. 12 is a plan view of the third or outer dilator tube of the dilation introducer of FIG. 8.

Referring to FIG. 12, the dilation introducer includes at least one additional dilator tube, such as a still shorter third or outer dilator tube 202 having a distal end 204 with a tapered tip 206, and a proximal end 208 to which a handle 210 is connected at its head end 212. The head end of the handle includes a radial aperture 214 for receiving the locking pin 218, and a longitudinal aperture 215 for receiving the distally projecting latching member of the cylindrical head of the second or intermediate dilator tube. The first locking pin 216 is substantially the same as the second locking pin 218. The third dilator tube has an inner lumen 219 with proximal and distal openings. A tubular bone drill or tap can be inserted through the third or outer dilator tube, and the tubular bone drill or tap can be threaded over a guide wire or K wire to contact the surface of the vertebra or bone to be treated, as described herein. As discussed herein, the bone drill could alternatively be passed through an intermediate dilator tube.

Figure 13:
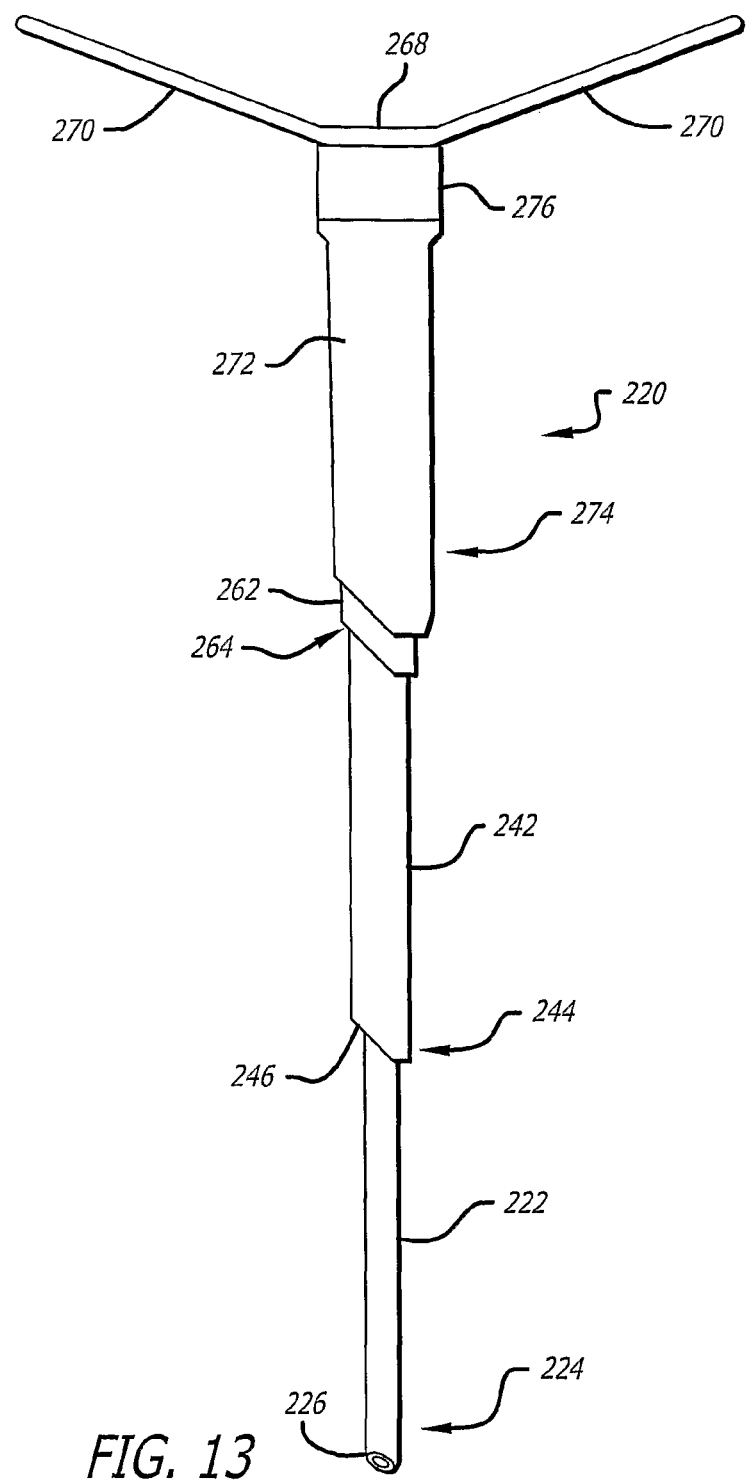
FIG. 13 is a plan view of a third embodiment of a dilation introducer in a locked configuration, according to the present invention.

With reference to FIGS. 13-18, a dilation introducer 220 is shown in a locked assembled configuration in FIG. 13, and is shown in an unlocked, collapsed configuration in FIG. 14. As is illustrated in FIG. 15, the dilation introducer includes a first or inner dilator tube 222 having a distal end 224 with a tapered, beveled tip 226, and a proximal end 228 with a cylindrical head 230. Means for removably connecting the first and second dilator tubes together in a locked configuration includes a pair of opposing bayonet pins 232 extending from the proximal end of the first dilator tube. The first dilator tube has an inner lumen 234 with a distal opening 236 and a proximal opening 238.

As is shown in FIG. 16, the dilation introducer includes a shorter second or intermediate dilator tube 242 having a distal end 244 with a tapered, beveled tip 246, and a proximal end 248 with a cylindrical head 250. A means for removably connecting the second and third dilator tubes together in a locked configuration includes a pair of opposing bayonet pins 252. The second dilator tube has an inner lumen 254 with a distal opening 256 and a proximal opening 258, and as part of the means for removably connecting the second and third dilator tubes together, interior opposing bayonet slots 260 for receiving the pair of opposing bayonet pins of the first or inner dilator tube.

Referring to FIG. 17, the dilation introducer includes at least one additional dilator tube, such as a still shorter third or outer dilator tube 262 having a distal end 264 with a tapered, beveled tip 266, and a proximal end 268 having a pair of opposing handles 270. The third dilator tube has an inner lumen 271, with a proximal opening and a distal opening. In certain embodiments, a plastic sleeve, such as plastic sleeve 272, is slidably disposed over the shaft of the third or outer dilator tube, and the plastic sleeve can have a distal tapered, beveled end 274. A proximal sleeve ring 276 may also be slidably disposed over the shaft of the third or outer dilator tube between the plastic sleeve 272 and the opposing handles.

As is illustrated in FIGS. 13 and 14, in this embodiment the tapered tips of the dilator tubes and plastic sleeve are beveled or angled at a common angle with respect to the longitudinal axis of the dilation introducer. Because of this common angle of the beveled tips of the dilator tubes and plastic sleeve, the beveled tips of two or more dilator tubes, or the dilator tube and the plastic sleeve, can be aligned generally parallel to each other and kept in a desired relationship. Keeping the beveled tip edges aligned facilitates dilation of the soft tissues as the dilator tubes are passed deeper into the tissue or wound. The beveled end of this embodiment can be beneficial when passing the dilator tube at an acute angle to the skin surface or if the bone tissue to be treated is itself not at a perpendicular angle to the longitudinal axis of dissection of the dilator tubes. An optimal angle of passage through the soft tissue with this embodiment will be such that the beveled edges of the dilator tube and plastic sleeve are aligned parallel to the bone surface to be worked on. The beveled end of the dilator tube will lay substantially flat against the bone tissue and thereby exclude the surrounding soft tissues from the line of sight of the surgeon down the central axis of the dilator tube and plastic sleeve.

For example, the beveled tip of this embodiment is advantages when the hard tissue to be exposed is not in a plane that is substantially parallel with the skin surrounding the entry wound edge. For example, the lumbar facet joints are generally vertical in alignment when a patient is prone on the operating room table. Therefore, a beveled end dilator can be passed generally perpendicular to the skin on entry, and the beveled edge of the dilator will align substantially parallel with the facet joint, thereby more efficiently retracting the soft tissues surrounding the facet joint. In yet another example, the beveled tip of this embodiment can be beneficial when passing the dilator tubes lateral to the lumbar facet joints, thereby exposing the lateral aspect of the lumbar facet where it intersects with the transverse process. The beveled tip can more efficiently keep the soft tissue out of the line of sight of the surgeon while allowing good exposure of generally vertical lateral aspect of the facet joint.

As part of the means for removably connecting the second and third dilator tubes together in this embodiment, the third dilator tube includes interior opposing bayonet slots 278 for receiving the pair of opposing bayonet pins of the second or intermediate dilator tube. A tubular bone drill or tap can be inserted through the first or inner dilator tube, and the tubular bone drill or tap can be threaded over a guide wire or K wire to contact the surface of the vertebra or bone to be treated, as described above.

Figure 19:
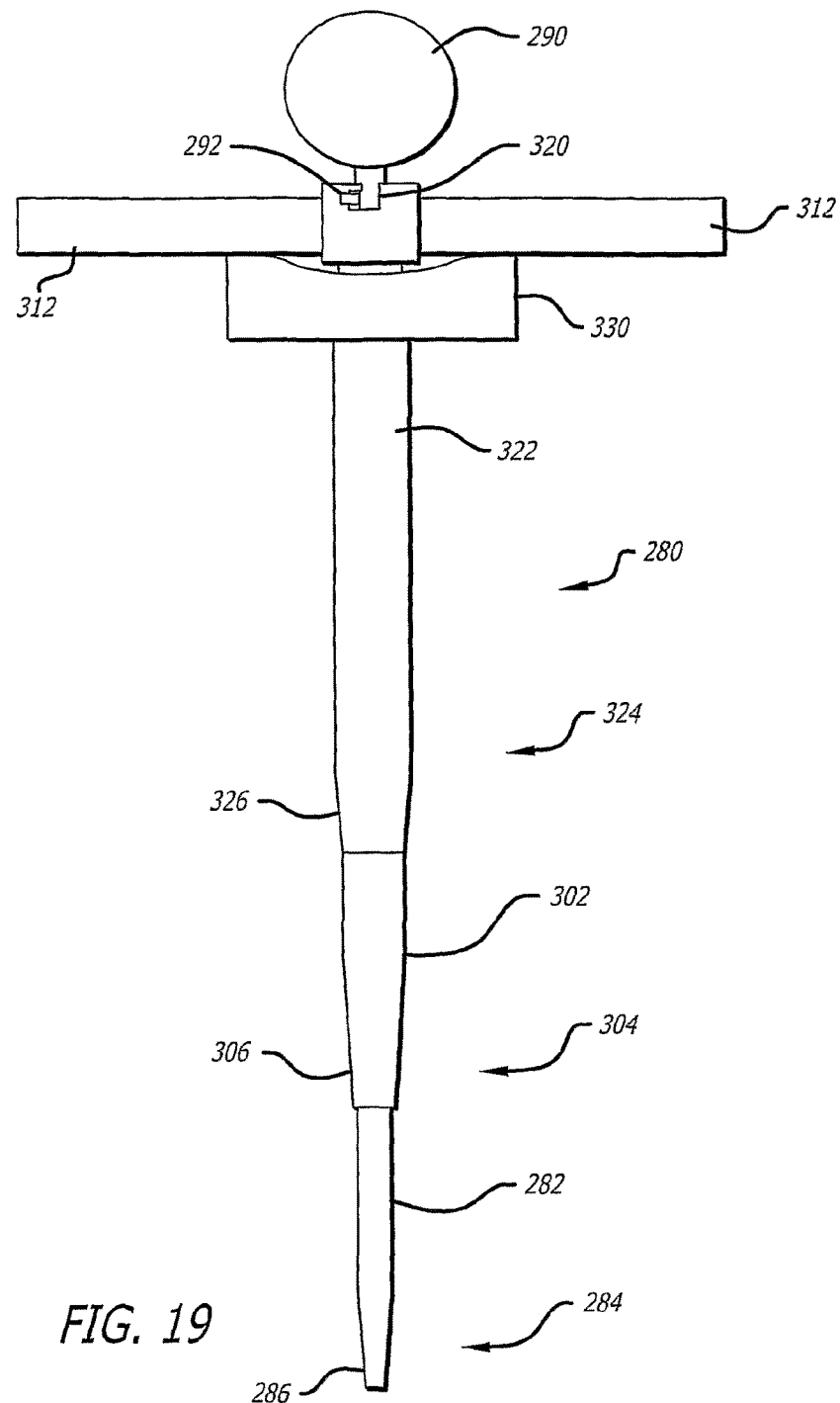
FIG. 19 is a plan view of a fourth embodiment of a dilation introducer in a locked configuration, according to the present invention.
Figure 20:
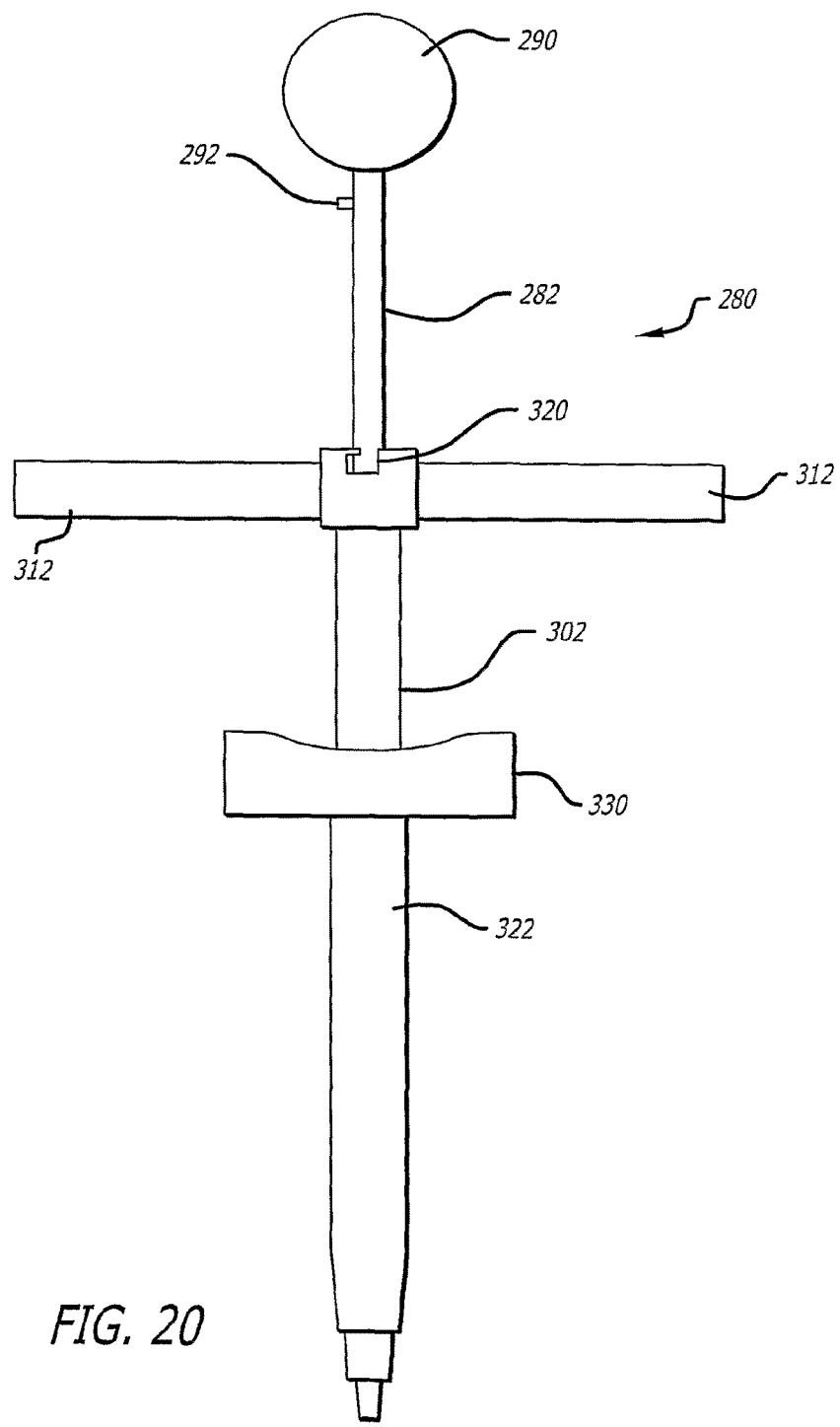
FIG. 20 is a plan view of the dilation introducer of FIG. 19 shown in an unlocked, collapsed configuration.

With reference to FIGS. 19-23, another dilation introducer 280 is shown in a locked assembled configuration in FIG. 19, and is shown in an unlocked, collapsed configuration in FIG. 20. Referring to FIG. 21, the dilation introducer includes a first or inner dilator tube 282 having a distal end 284 with a tapered tip 286, and a proximal end 288 having a generally spherical handle or head 290. As part of a means for removably connecting first and second dilator tubes together in a locked configuration or in a substantially fixed position, the proximal end of the first dilator tube near the handle includes a bayonet pin 292. The first dilator tube has an inner lumen 294 with a distal opening 296, and a proximal opening 298. In other embodiments, the bayonet pin can be omitted, and the substantially fixed position can be obtained simply by holding the handle 290 and the handles 312 together with a hand or other suitable device.

Referring to FIG. 22, the dilation introducer includes a shorter second or intermediate dilator tube 302 having a distal end 304 with a tapered tip 306, and a proximal end 308 having a generally cylindrical head 310 and a pair of opposing handles 312. The second dilator tube has an inner lumen 314 with a distal opening 316 and a proximal opening 318. As part of the means for removably connecting first and second dilator tubes together in a locked configuration, the proximal end of the second dilator tube includes a bayonet slot 320 formed in the cylindrical head for receiving the bayonet pin of the first or inner dilator tube. As discussed herein, the bayonet slot 320 can be omitted if the first dilation tube does not include a bayonet pin.

Referring to FIG. 23, the dilation introducer includes at least one additional dilator tube, such as a still shorter third or outer dilator tube 322, currently preferably formed of a polymeric material, having a distal end 324 with a tapered tip 326, and a proximal end 328 with a generally cylindrical head end or handle 330. The third dilator tube has an inner lumen 332, with proximal and distal openings. A tubular bone drill or tap can be inserted through any of the tubes, and the tubular bone drill or tap can be threaded over a guide wire or K wire to contact the surface of the vertebra or bone to be treated, as described above. Furthermore, in the additional embodiment, a bushing or a stepped shaft for the drill may be used to match the drill bit shaft outer diameter to the inner diameter of the dilator tubes, thereby facilitating drilling a hole aligned down the center of the dilator tube.

Referring to FIGS. 27-29, a guide wire or K wire assembly 340 for use with the telescoping dilation introducer of the invention includes an elongated, generally cylindrical first section 342 and an elongated, tubular second section 344 that is adapted to receive the first section. The first section includes a proximal enlarged head or stop portion 346, and a relatively narrow elongated body portion 348. The elongated body portion is preferably formed with a proximal section 350 having a relatively larger diameter than the body portion 348 to provide relatively greater strength, rigidity and torquability for manipulation of the guide wire, and a relatively narrower diameter main section 352 connected to the proximal section, and a pointed distal tip 354 at the distal end 358 of the main section. Proximal section 350 includes a cavity to receive a proximal portion of second section 344. The elongated tubular second section 344 has a relatively larger diameter than the main section 352 and an internal bore slightly larger in diameter than the main section 352 for receiving the main section, as is illustrated in FIG. 28. The tubular second section 344 advantageously also includes a frustoconical distal tip 362 with a narrowed portion 364 at the distal end 366 of the tubular distal section, and presenting an enlarged flat shoulder 368 at the proximal end of the frustoconical distal tip, so that when the guide wire assembly is assembled as shown in FIG. 29, and the elongated main section is received in the internal bore of the elongated tubular section, and the proximal section of the elongated body portion of the elongated generally cylindrical section is seated against said proximal end of said elongated tubular section, the pointed distal tip extends out of said frustoconical distal tip of said elongated tubular section so that the assembly presents a pointed distal end, with a proximal shoulder against which a telescoping dilation introducer can be pushed for operation of the telescoping dilation introducer. The elongated generally cylindrical first section thus adds a sharp point to the relatively blunt distal end of the elongated tubular second section, allowing the guide wire assembly to be inserted through soft tissue for placement in or adjacent to a soft tissue target of interest, such as an organ. Since soft tissues do not provide hard or rigid surfaces against which the telescoping dilation introducer can be pushed, after the sharp point of the guide wire is placed in the desired location in the soft tissue, the first section 342 can be removed from the second section 344, leaving the blunt distal end in place at the desired location in the soft tissue, and the telescoping dilation introducer can be placed over the second section 344 and pressed against the shoulder of the blunt distal end for operation of the telescoping dilation introducer. In other embodiments, non-frustroconical shaped distal ends can be provided. Such embodiments still comprise a distal end region that has a maximum cross-sectional area, distance, or diameter, relative to a more proximal regions of the guide wire.

Figures 30, 31:
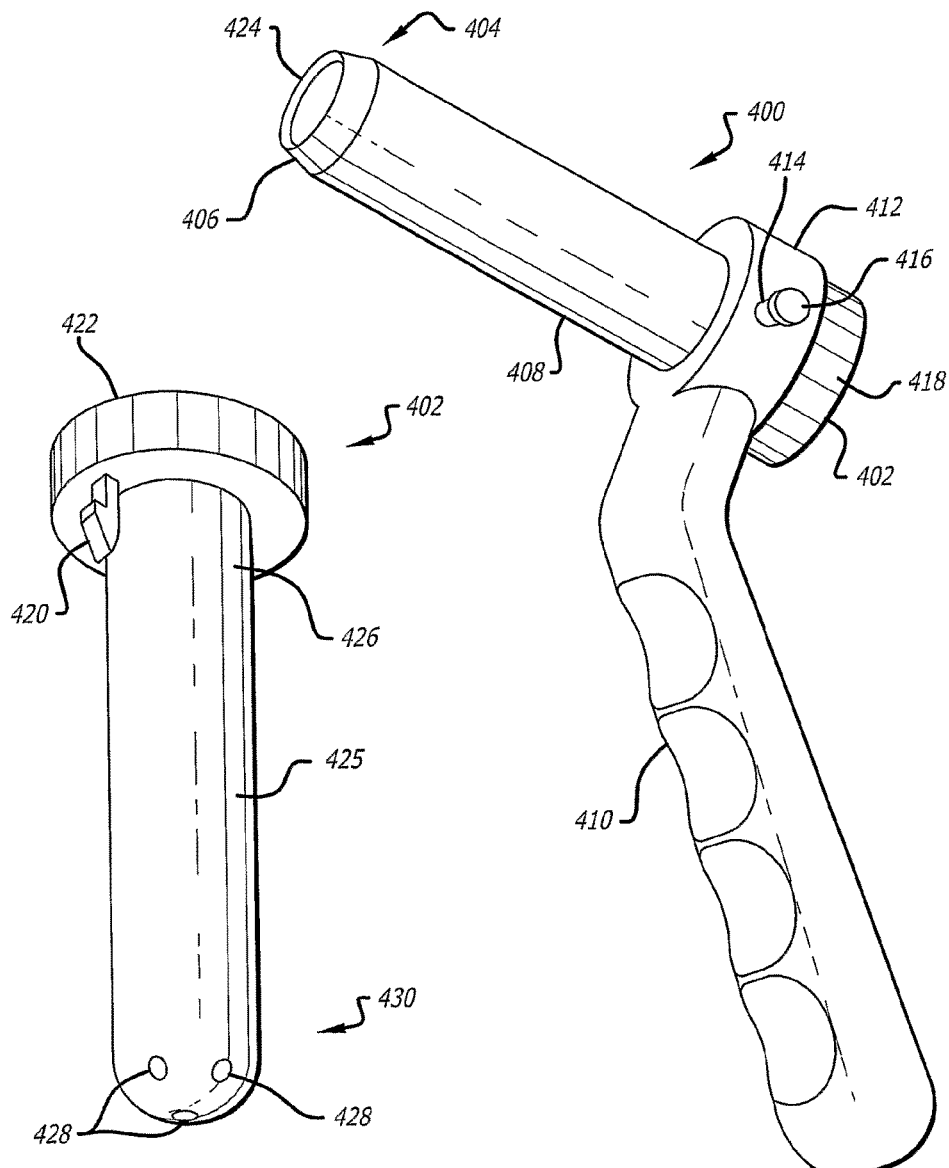
FIG. 30 is a perspective view of a variation of the outer dilator tube of the embodiment of FIGS. 8-12, with a parallel guide.
FIG. 31 is a perspective view of the parallel guide from FIG. 30.

As is shown in FIG. 30, in one variation of the additional or outer dilator tube, such as in the embodiment of FIGS. 8-12 for example, the outer dilator tube 400 includes a guide insert, or a guide wire insert, 402, shown in FIG. 31. The outer dilator tube has a distal end 404 with a tapered tip 406, and a proximal portion 408 to which a handle 410 is connected at the extreme proximal or head end 412 of the outer dilator tube. The head end of the outer dilator tube includes a radial aperture 414 for receiving the locking pin 416, and a longitudinal aperture 418 for receiving a distally projecting latching member 420 of the cylindrical head 422 of the guide insert. The outer dilator tube has an inner bore 424 with proximal and distal openings.

The guide insert includes a main cylindrical shaft 425 connected at or extending from a proximal end 426 to the cylindrical head of the guide insert. The guide insert includes a plurality of longitudinal bores 428 extending along the length of the guide insert from the distal end 430, with distal openings visible in FIG. 31, to proximal openings (not shown) in the cylindrical head of the parallel guide insert. The longitudinal bores 428 are illustrated as extending through the guide insert and being parallel to each other or to a longitudinal axis of the guide insert. Thus, the embodiment illustrated in FIG. 31 can be understood to be a parallel guide wire insert or parallel guide insert. Other embodiments can include one or more bores that are not parallel to each other. For example, a guide wire insert can include a plurality of diverging bores (e.g., the bores diverge from the proximal end toward the distal end of the guide insert) or a plurality of converging bores (e.g., the bores converge from the proximal end toward the distal end of the guide insert). Guide inserts comprising parallel bores, such as shown in FIG. 33, may be particularly beneficial in hip surgeries. Guide inserts comprising diverging bores may be beneficial in spinal surgeries, such as spinal plate procedures. The insertion of the distally projecting latching member of the cylindrical head of the guide insert in the longitudinal aperture of the head end of the handle of the outer dilator tube insures that the guide insert remains in a fixed position in the outer dilator tube when the guide insert is secured with the locking pin. A single guide wire or K wire or other device may be passed through one or more of the bores of the guide insert, or multiple guide wires or K wires or other devices may be passed through a plurality of the bores simultaneously, as desired. The guide insert may also be provided without a latching member, in order to allow the guide member to be rotated freely to allow alignment of the desired locations of the guide wires through the holes in the guide insert.

Referring to FIG. 32, in another variation of the additional or outer dilator tube, such as in the embodiment of FIGS. 13-18 for example, the outer dilator tube 440 includes a parallel guide insert 442, shown in FIG. 33. The outer dilator tube has a distal end 444 with an angled tip 446, and a proximal end 448 to which a handle 450 is connected at the extreme proximal or head end 452 of the outer dilator tube. The head end of the outer dilator tube includes a radial aperture 454 for receiving the locking pin 456, and a longitudinal aperture 458 for receiving a distally projecting latching member 460 of the cylindrical head 462 of the parallel guide insert. The outer dilator tube has an inner bore 464 with proximal and distal openings. The angled tip 446 of the outer dilator tube is advantageous when the bone surface is not perpendicular to the longitudinal axis of entry of the dilator tube 440 through the soft tissues. The angled tip is particularly beneficial when the dilator tube angle of entry is at an acute angle to the skin surface. As discussed herein, this embodiment and other similarly structured embodiments, may be beneficial in hip surgical procedures.

The parallel guide insert includes a main cylindrical shaft 465 connected at a proximal end 466 to the cylindrical head of the parallel guide insert. The parallel guide insert 442 includes a plurality of longitudinal bores 468 extending the length of the parallel guide insert from the angled distal end 470, with distal openings visible in FIG. 33, to proximal openings (not shown) in the cylindrical head of the parallel guide insert. The insertion of the distally projecting latching member of the cylindrical head of the parallel guide insert in the longitudinal aperture of the head end of the handle of the outer dilator tube insures that the parallel guide insert remains in a fixed position in the outer dilator tube when the parallel guide insert is secured with the locking pin. The angled tips of the outer dilator tube and the parallel guide insert are beveled or angled at a common angle with respect to the longitudinal axis of the dilation introducer, so that the angled tips of the outer dilator tube and the parallel guide insert can be aligned together generally parallel to each other, with the bore and dilation passage of the dilation introducer aligned at a predetermined desired angle with respect to the soft tissue to be dilated and the bone tissue to be treated. A single guide wire or K wire or other device may be passed through one or more of the bores of the parallel guide insert, or multiple guide wires or K wires or other devices may be passed through a plurality of the bores simultaneously, as desired. This embodiment may be particularly useful in surgical procedures of the hip. Thus, this embodiment of the tissue dilation system may be structured for a hip surgical procedure. As discussed herein, the structure of the system can be specific for a desired target structure, such as a portion of a hip, so that a desired contact or engagement of the distal end of the dilation tube can be obtained relative to a surface of the target structure.

Figure 36:
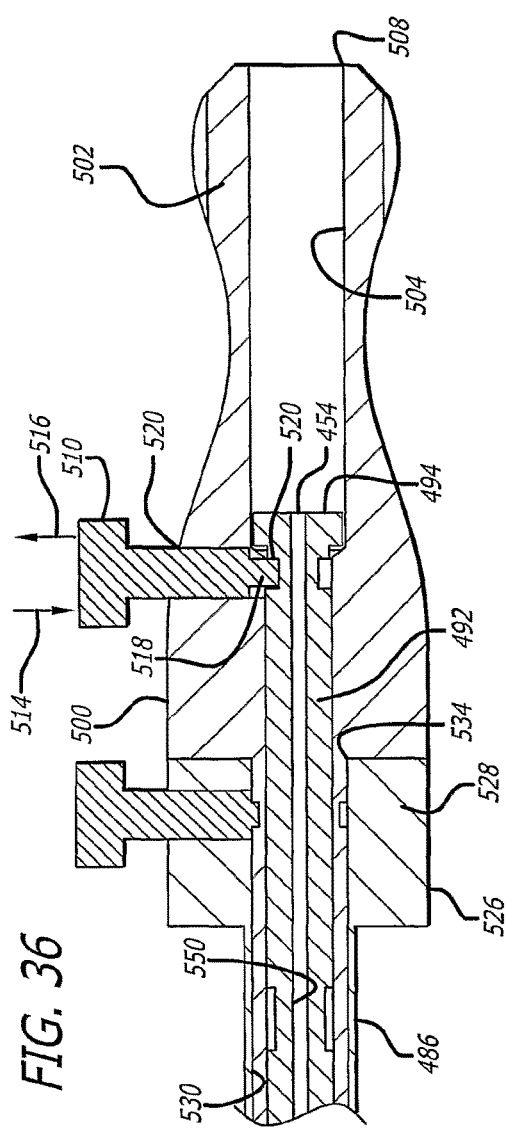
FIG. 36 is an expanded view of a portion of FIG. 35.
Figure 37:
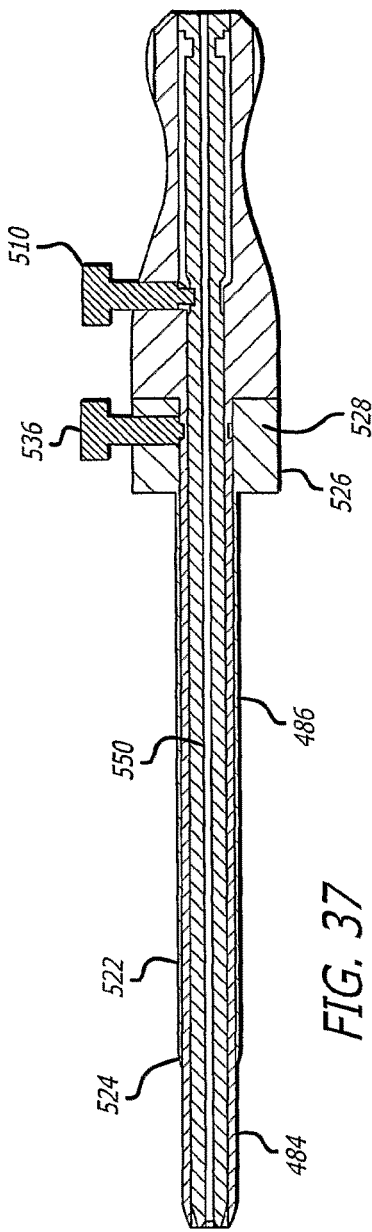
FIG. 37 is a cross-sectional view of the dilation introducer of FIG. 34 with the first inner dilator moved to an unlocked, collapsed position.
Figure 38:
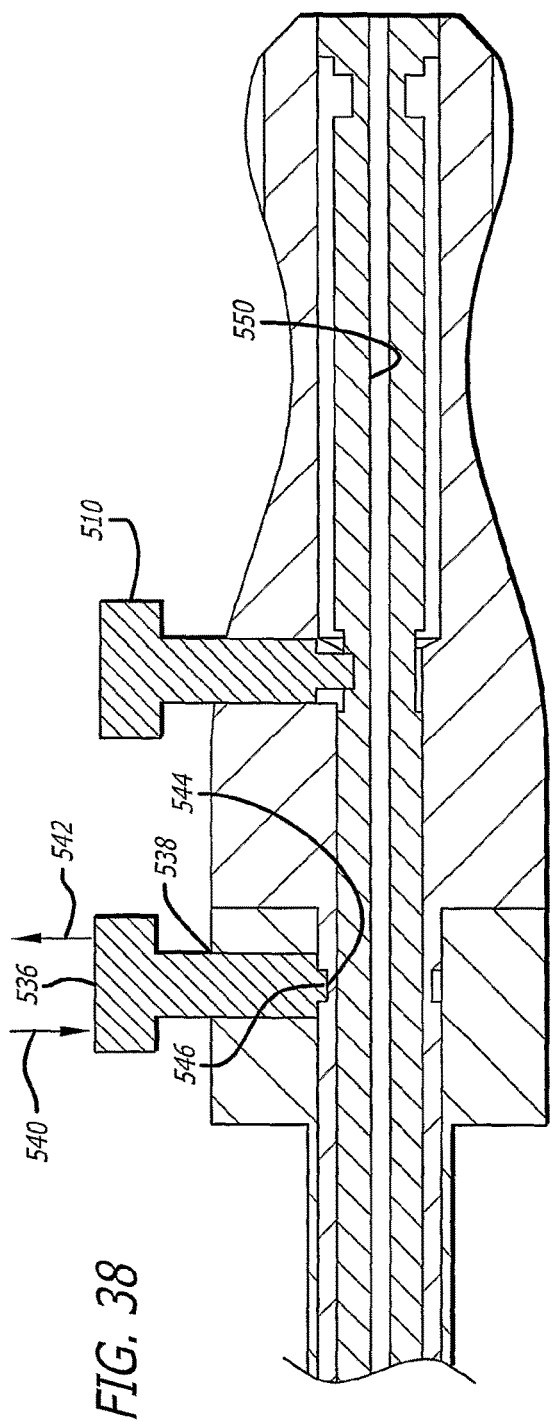
FIG. 38 is an expanded view of a portion of FIG. 37.
Figure 39:
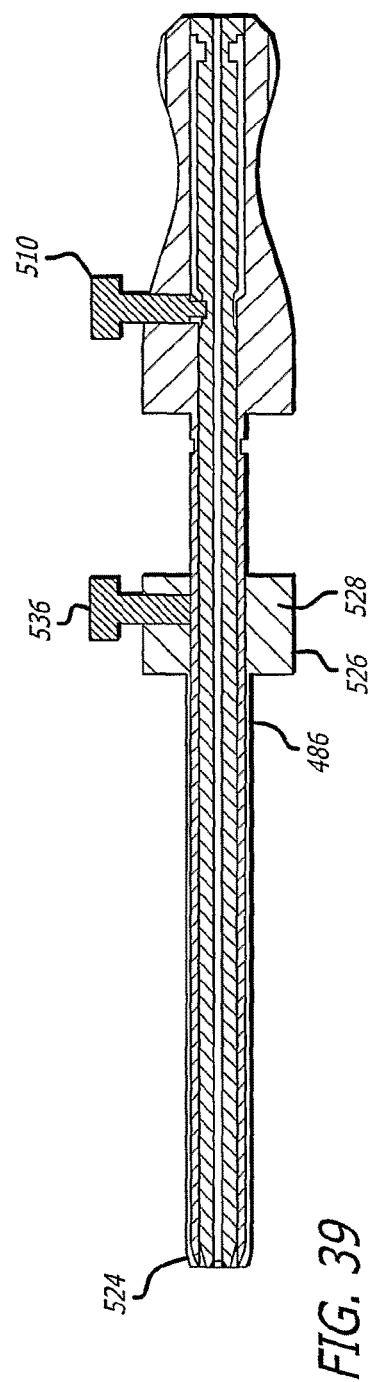
FIG. 39 is a cross-sectional view of the dilation introducer of FIG. 34 with the third outer dilator moved to an unlocked, collapsed position.
Figure 40:
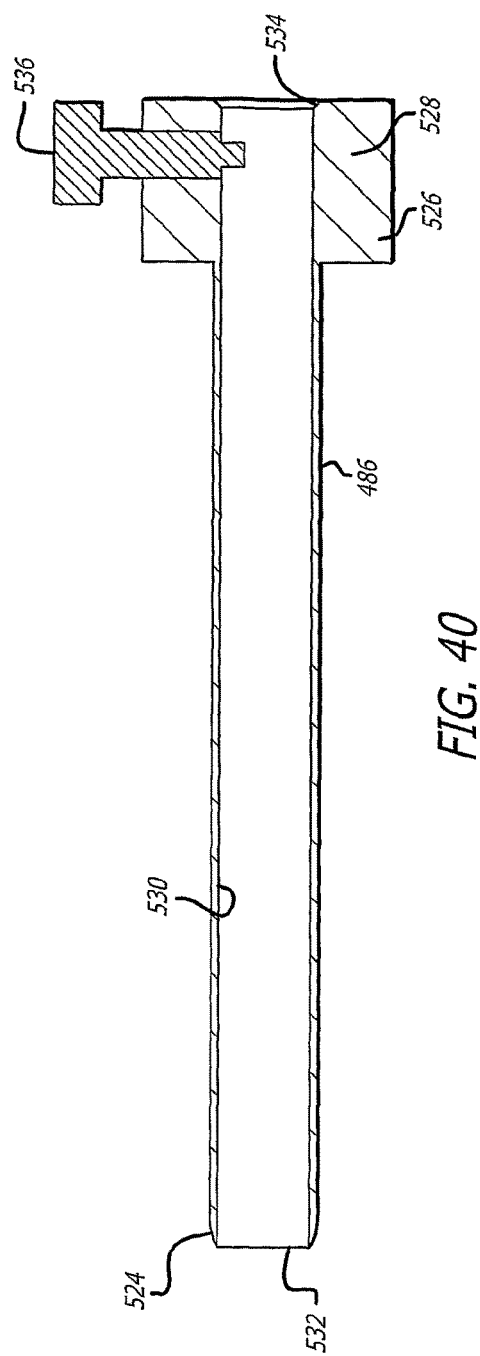
FIG. 40 is a cross-sectional view of the third outer dilator of the dilation introducer of FIG. 34 with the first inner dilator and second intermediate dilator removed.
Figure 52:
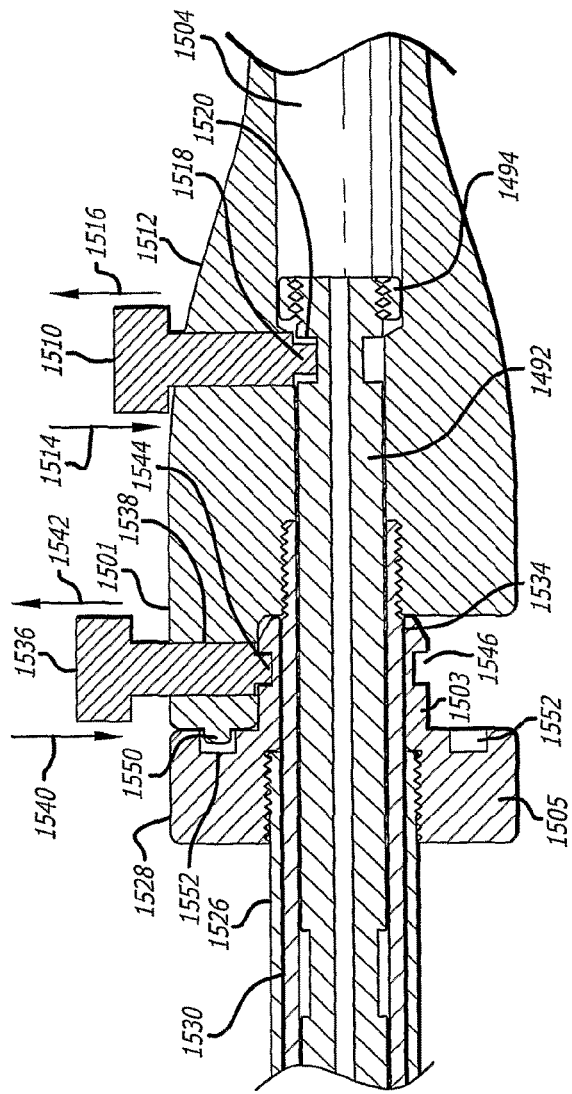
FIG. 52 is a magnified longitudinal cross sectional view through the latching and anti-rotation features of the dilation introducer in FIG. 50.
Figure 53:
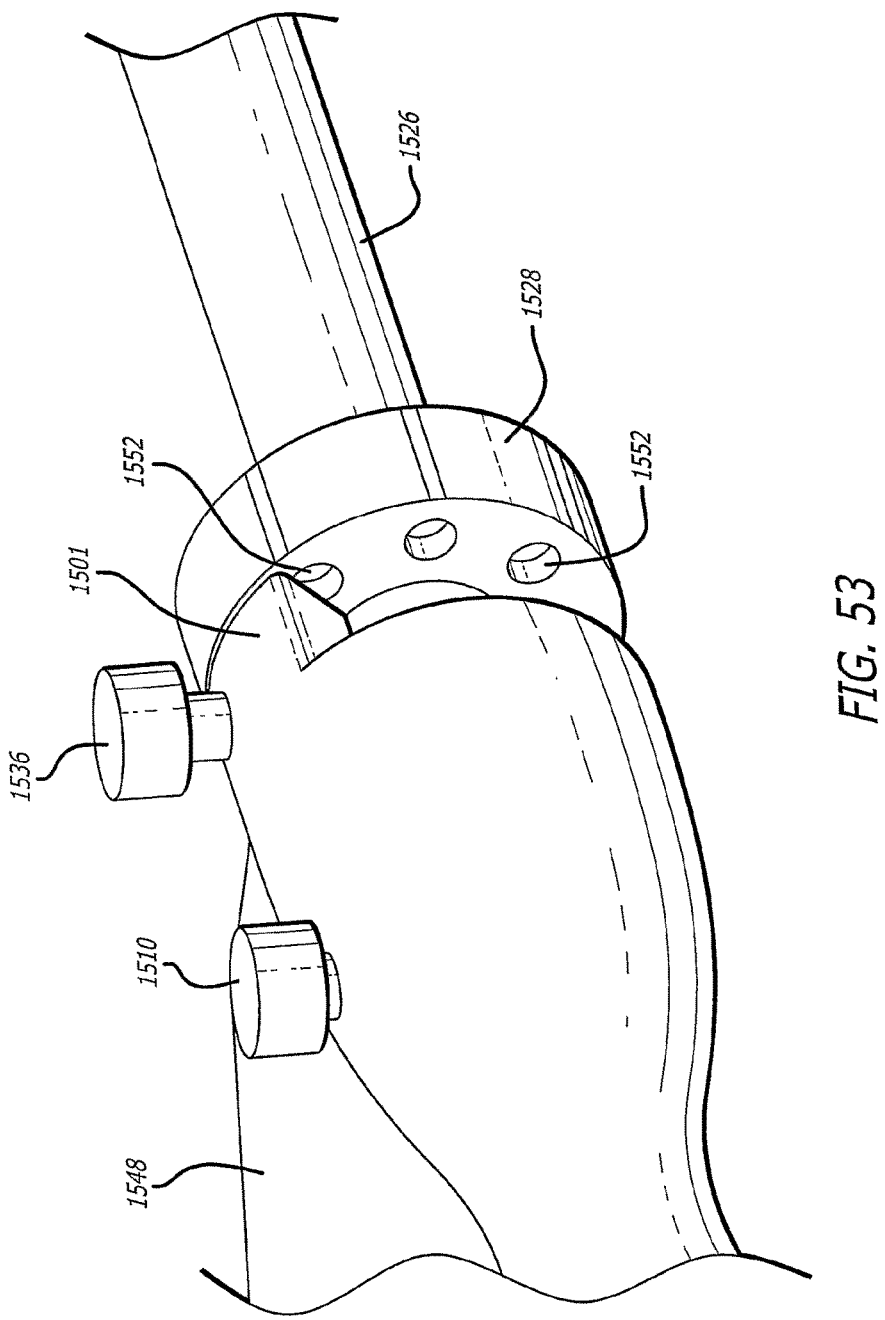
FIG. 53 is a perspective view of the dilation introducer in FIG. 50 showing the dilators in a locked position and showing the anti-rotation features in greater detail.
Figure 54:
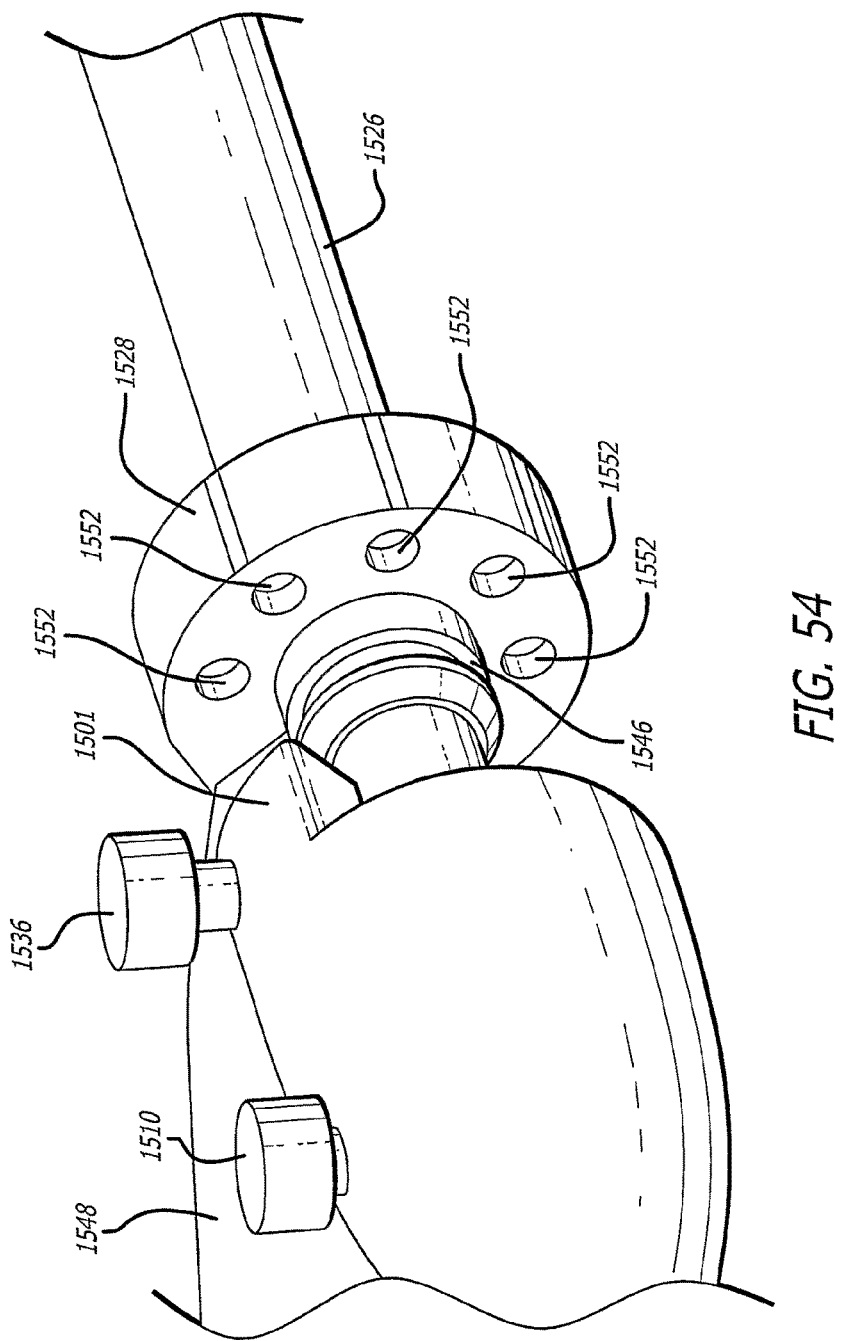
FIG. 54 is a perspective view of the dilation introducer in FIG. 50 showing the dilators in an un-locked position and showing the anti-rotation features in greater detail.
Figure 55:
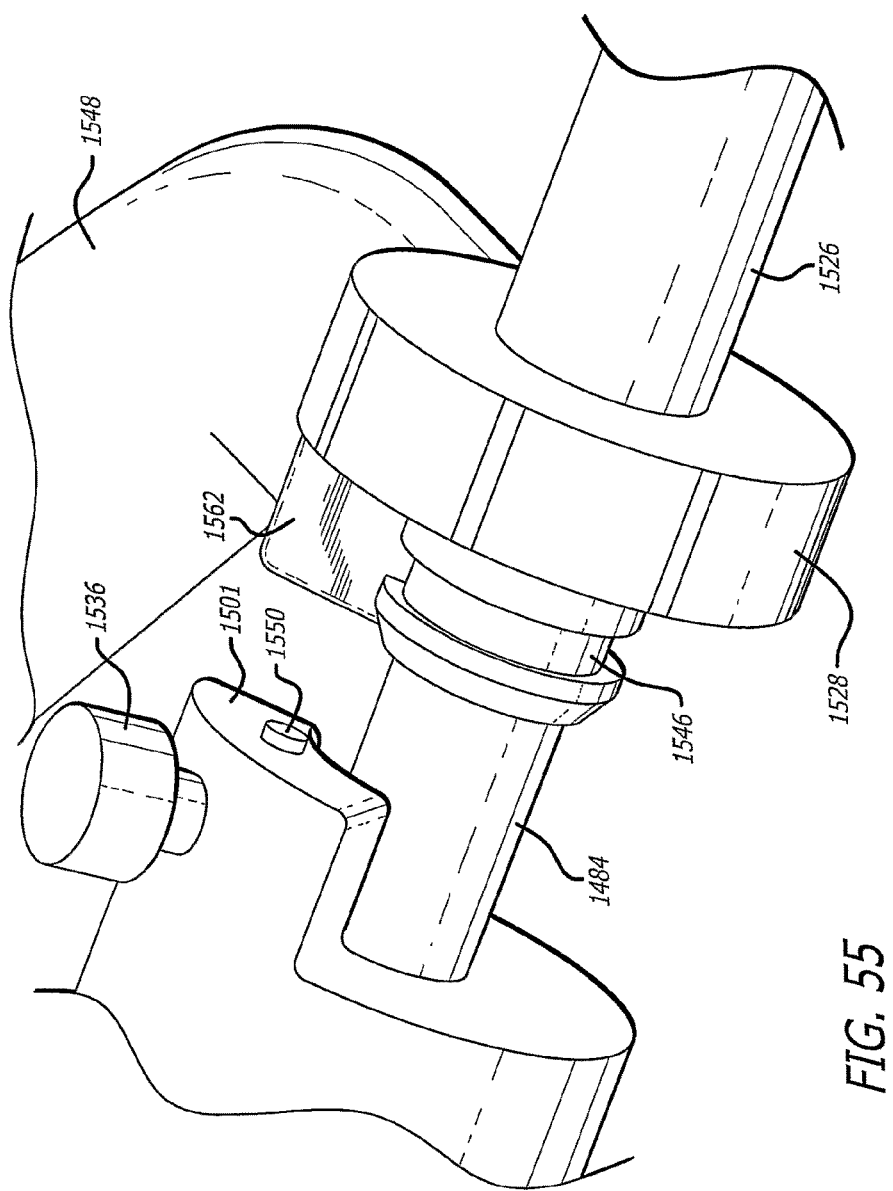
FIG. 55 is a perspective view of the dilation introducer in FIG. 50 showing the dilators in a locked position and showing the anti-rotation features in greater detail.

With reference to FIGS. 34-43, an additional embodiment of a dilation introducer 480 is shown in a locked assembled configuration in FIG. 34, and is shown in an unlocked, collapsed configuration in FIG. 39. Referring to FIGS. 34-39, the dilation introducer includes a first or inner cylindrical dilator 482, a second tubular dilator 484, and an additional tubular dilator such as a third tubular dilator 486. The first or inner cylindrical dilator and the second tubular dilator may be provided in various lengths, wherein either dilator is equal or longer or shorter in length than the others. The first or inner cylindrical dilator has a distal portion 488 with a tapered tip 490 which may be serrated, and a proximal portion 492 having a head portion 494. The head portion of the first dilator tube may have a greater maximum cross-sectional area or diameter than a more proximal portion of the dilation tube. An enlarged head portion relative to the body of the dilation tube may be effective in preventing the dilation tube with the enlarged head portion from falling out of a handle. The enlarged head portion 494 can be integrally formed with the body of the dilation tube, as shown in FIG. 36. Or, the enlarged head portion can be formed by providing a cap over the proximal end of the dilation tube, as shown in FIG. 52, and as discussed herein. In various embodiments, the first or inner cylindrical dilator may be cannulated, for example to allow passage of a guide wire down the central longitudinal axis of the first dilator, or the first or inner cylindrical dilator may be without a lumen and uncannulated.

The second dilator tube has a distal end 496 with a tapered tip 498, a proximal end 500 with a generally tubular head 502, and an inner lumen 504 with a distal opening 506 and a proximal opening 508. The first cylindrical dilator is removably received in the second tubular dilator for slidable telescoping movement within the second dilator tube. The first and second dilators are connected together in a locked configuration with a first latching button 510 disposed in the tubular head of the second tubular dilator and extending through a first aperture 512 in the tubular head of the second tubular dilator, so that the first latching button is moveable between a radially inward locking position (arrow 514) and a radially outward unlocking position (arrow 516). The distal end 518 of the first latching button is removably received in a recess or groove 520 of the first cylindrical dilator in the locking position, so as to engage and lock the first and second dilators together. The first latching button can thus be pulled radially outwardly to release the first dilator, to allow the first dilator to slide to the unlocked collapsed configuration, shown in FIG. 37. In the illustrated embodiments, the recess or groove circumscribes the dilator tube. The recess or groove 520 does not provide access to the lumen of the dilation tube. In other embodiments, an aperture may be present that provides access to the dilation tube lumen.

As shown in FIG. 36A, a latching button 510' may be used with the present systems. The latching button 510' includes a biasing member, such as a spring, located within a body cavity. The biasing member is effective in biasing the latching button into a locked position. The head of the latching button can be pulled against the force provided by the biasing member to unlock one or more of the dilation tubes. Thus, embodiments of latching buttons similar to 510' can be understood to be hand retractable spring plungers. Examples of these latching buttons are publicly available, such as from McMaster-Carr® (Los Angeles, Calif.).

Referring to FIGS. 34-40, an additional dilator tube has a distal end 522 with a tapered tip 524, a proximal end 526 with a tubular head 528, and an inner lumen 530 with a distal opening 532 and a proximal opening 534. The second tubular dilator is removably received in the additional tubular dilator for slidable telescoping movement within the additional tubular dilator, and as shown in FIG. 39, the second tubular dilator and the additional tubular dilator also have an unlocked configuration in which the additional tubular dilator is permitted to slidably telescope over the second tubular dilator to dilate the patient's soft tissue at the distal end of the dilation introducer. As illustrated, the third dilation tube or additional tubular dilator is slidably moveable relative to the locked relationship between the first dilation tube and the second dilation tube.

The second dilator tube and the additional tubular dilator are connected together in a locked configuration with a second latching button 536 disposed in the tubular head of the additional tubular dilator. The second latching button extends through an aperture 538 in the tubular head of the additional tubular dilator and is moveable between a radially inward locking position (arrow 540) and a radially outward unlocking position (arrow 542). The distal end 544 of the second latching button is received and engaged in an recess or groove 546 of the second tubular dilator in the locking position to lock the second and the additional tubular dilators tubes in the locked assembled configuration. The second latching button can also be pulled to move radially outward to release the additional tubular dilator to slide to the unlocked, collapsed configuration, after which the first and second dilators may be removed. In one aspect, the additional tubular dilator comprises a handle 548 connected to the proximal end of said additional tubular dilator. In the embodiment, the tips of the dilators are beveled as an alternative to a taper.

Figure 41:
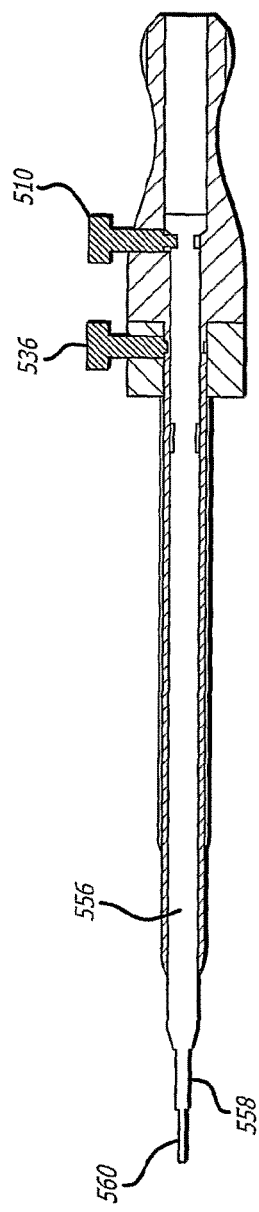
FIG. 41 is a cross-sectional view of the dilation introducer of FIG. 34 illustrating a first variation of the first inner dilator.

As is illustrated in FIGS. 35-39, in one present form, the cylindrical first dilator is tubular, having an inner lumen 550 with a distal opening 552 and a proximal opening 554. In the other embodiment, the first cylindrical dilator is tubular, but has no lumen and is not cannulated. In an alternative variation shown in FIG. 41, the first dilator has a solid cylindrical main body portion 556 having a first diameter D1, and the narrowed distal portion 558 having generally parallel sides and a second diameter D2 narrower than the first diameter D1. As is illustrated in FIG. 41, the first dilator may have the additional narrowed distal portion 560 having generally parallel sides and a third diameter D3 narrower than the second diameter D2. For example, in one illustrative and non-limiting embodiment, the length of the first and second narrowed distal portions combined may be approximately about 0.5 inches, the diameter D2 is about 0.128 inches, and the diameter D3 is about 0.062 inches. Other dimensions may be used for various applications.

In another alternative variation illustrated in FIG. 42, the first dilator has a solid cylindrical main body portion 562, and a progressively uniformly tapering distal portion 564. In yet another alternative variation shown in FIG. 43, the first dilator has a solid cylindrical main body portion 566, and a progressively stepwise tapering distal portion 568. The distal portion 568 includes a first tapered portion 570 with progressive generally tapering sides, an intermediate stepped portion 572 focally narrowing the diameter of the distal portion further, and then the additional tapered portion 574 with still a narrower diameter than the intermediate stepped portion 572.

Figure 50:
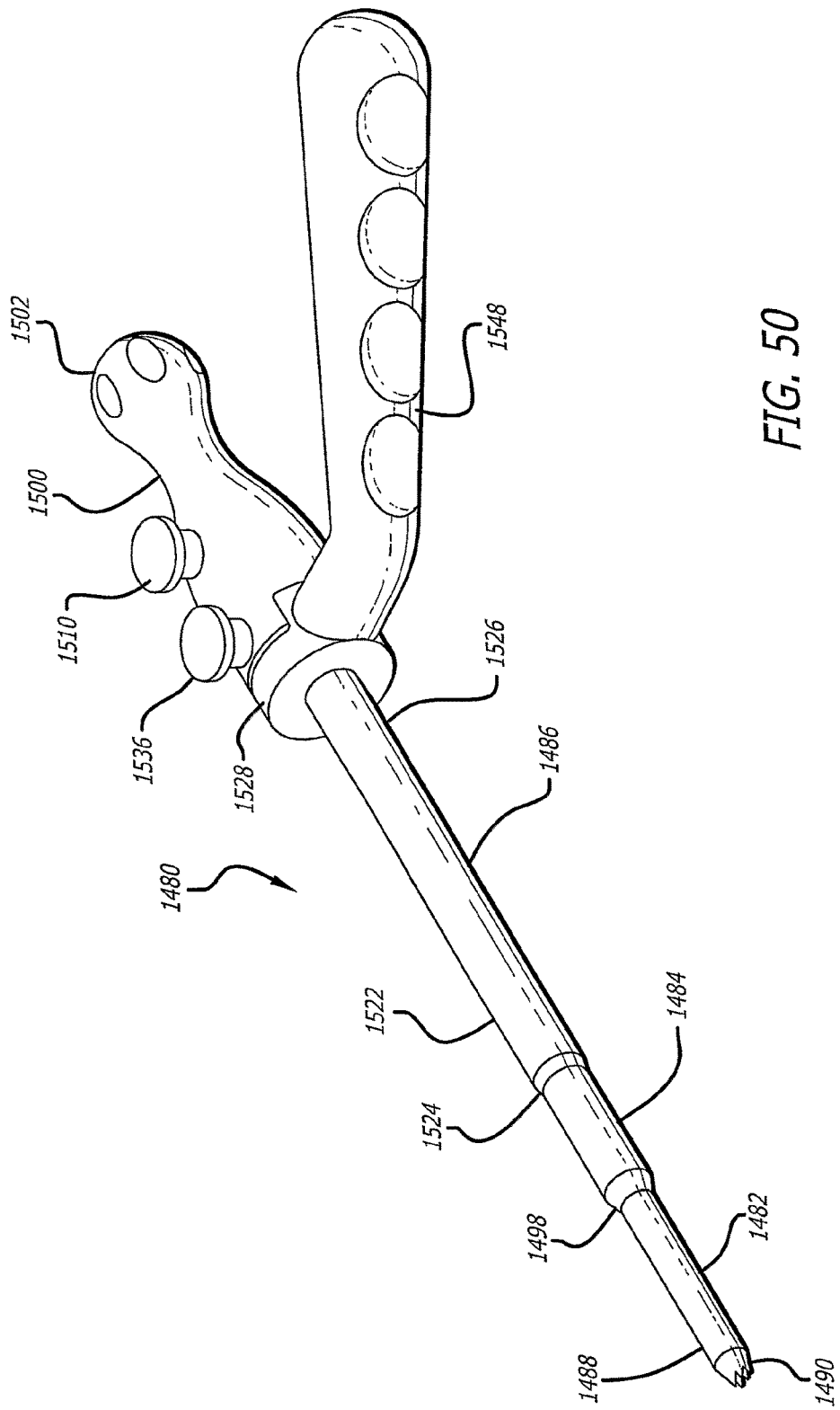
FIG. 50 is a perspective view of another embodiment of the dilation introducer having two latching buttons, a handle, and an anti-rotation feature.
Figure 51:
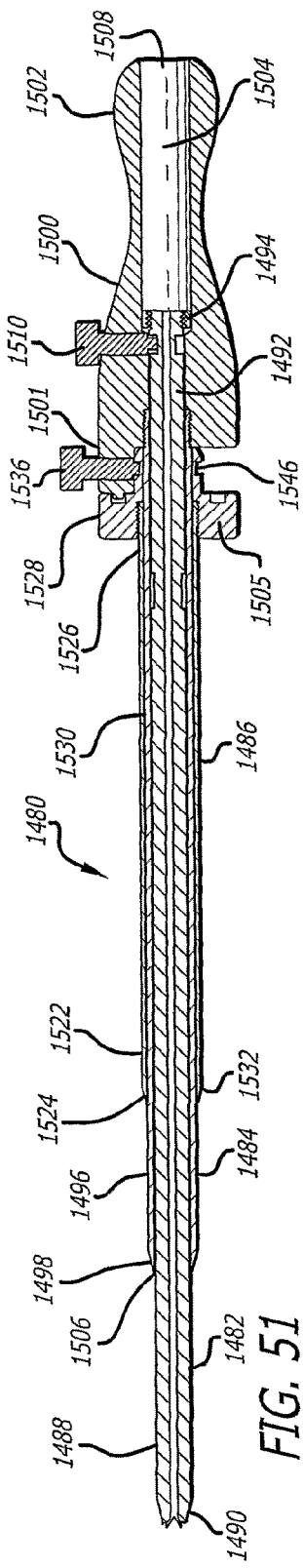
FIG. 51 is a longitudinal cross sectional view of the dilation introducer in FIG. 50.

Referring to FIGS. 50-58, a dilation introducer 1480 is shown in a locked assembled configuration in FIG. 50. Referring to FIGS. 50-52, the dilation introducer includes an inner first cylindrical tubular dilator 1482, a second tubular dilator 1484, and an additional tubular dilator such as a third tubular dilator 1486. The first or inner cylindrical dilator 1482 and the second tubular dilator 1484 may be provided in various lengths, wherein either dilator is equal or longer or shorter in length than the others. The first or inner cylindrical dilator has a distal portion 1488 with a tapered tip 1490, which may be serrated, and a proximal portion 1492 having a head portion 1494. In various embodiments, the first or inner cylindrical dilator 1482 may be cannulated, for example to allow passage of a guide wire down the central longitudinal axis of the first dilator, or the first or inner cylindrical dilator may be without a lumen and uncannulated.

The second dilator tube 1484 has a distal end 1496 with a tapered tip 1498, a proximal end 1500 with a generally tubular head 1502, and an inner lumen 1504 with a distal opening 1506 and a proximal opening 1508. The first cylindrical dilator 1482 is removably received in the second tubular dilator 1484 for slidable telescoping movement within the second dilator tube 1484. The first and second dilators are connected together in a locked configuration with a first latching button 1510 disposed in the tubular head 1502 of the second tubular dilator and extending through a first aperture 1512 in the tubular head of the second tubular dilator, so that the first latching button 1510 is moveable between a radially inward locking position (arrow 1514) and a radially outward unlocking position (arrow 1516). The distal end 1518 of the first latching button is removably received in an aperture or a circumferentially oriented groove 1520 of the first tubular dilator so as to engage and lock the first and second dilators together in the locking position. The circumferentially oriented groove 1520 does not need to extend completely around the first tubular dilator. The first latching button 1510 is pulled radially outwardly to release the first tubular dilator 1482, to allow the first tubular dilator to slide within the second tubular dilator 1484 to the unlocked collapsed configuration.

At least one additional dilator tube 1486 has a distal end 1522 with a tapered tip 1524 and a proximal end 1526 with a tubular head 1528 and a handle 1548. The additional dilator tube 1486 has an inner lumen 1530 with a distal opening 1532 and a proximal opening 1534. The second tubular dilator 1484 is removably received in the additional tubular dilator 1486 for slidable telescoping movement within the additional tubular dilator 1486. As shown in FIG. 50-52, the second tubular dilator 1484 and the additional tubular dilator 1486 also have a locked configuration in which the additional tubular dilator 1486 is not permitted to slidably telescope over the second tubular dilator 1484.

The tubular head 1528 of the additional dilator tube 1486 includes a larger diameter proximal portion 1505 and a smaller diameter substantially tubular distal portion 1503. As shown also in FIG. 52, the smaller diameter substantially tubular proximal portion 1503 is sized to fit under an overhanging lip 1501 of the second tubular dilator, when the central longitudinal axis of both the second dilator 1484 and the additional dilator 1486 are aligned. There is a circumferentially oriented channel 1546 in the exterior of the smaller radius proximal portion 1503 for receiving a distal end 1544 of a second latching button 1536. The circumferentially oriented channel 1546 does not need to extend completely around the exterior of the smaller radius proximal portion 1503.

The second dilator tube 1484 and the additional tubular dilator 1486 are connected together in a locked configuration with the second latching button 1536 disposed in the overhanging lip 1501 of the second tubular dilator 1486. The second latching button extends through an aperture 1538 in the overhanging lip 1501 of the second tubular dilator 1486 and is moveable between a radially inward locking position (arrow 1540) and a radially outward unlocking position (arrow 1542). The distal end 1544 of the second latching button is removably received in the channel 1546 located in the tubular head 1528 of the additional tubular dilator 1486, in the locking position, to lock the second tubular dilator 1484 and the additional tubular dilator 1486 in the locked assembled configuration. The second latching button 1536 is pulled radially outward to release the additional tubular dilator 1486 to slide to the unlocked configuration. Furthermore, the first dilator 1482 and second dilators 1484 may be removed together as a unit from the additional tubular dilator 1486. In other words, the first dilator 1482 and second dilator 1484 can be kept locked together and can be removed from the additional dilator 1486 by unlocking the second latching button 1536 alone. An advantage of this embodiment is that the latching buttons are both removable from the surgical field with the release of the second dilator from the additional tubular dilator. The additional tubular dilator being free of protuberances, such as the latching buttons, is less likely to catch surgical sponges and sutures, for example, on the dilation introducer.

In one embodiment, the additional tubular dilator 1486 further includes a handle 1548 connected to the proximal end of the additional tubular dilator 1486, for example to the tubular head 1528. In at least one variation of this embodiment, the tips of the dilators are beveled as an alternative to a taper. The first dilator may be cannulated or not cannulated. As an alternative to a continuous taper, the first dilator may have a step wise narrowing from proximal to distal as explained elsewhere in the specification. These variations in dilator tips are similar to those described above.

In at least one embodiment, the present systems comprise an anti-rotation feature. As shown in FIG. 51-58, the overhang lip 1501 of the second tubular dilator 1484 has at least one distally protruding peg 1550 and a proximal surface of the tubular head 1528 of the at least one additional tubular dilator 1486 has at least one peg engagement recess 1552. In yet another embodiment, the proximal surface of the tubular head 1528 of the at least one additional tubular dilator 1486 has a plurality of peg engagement recesses 1552. Multiple pegs or peg engagement recesses are advantageous in providing flexibility where to set and fix the rotation position of the second tubular dilator in relationship to the additional tubular dilator. When the second tubular dilator 1484 is locked to the additional tubular dilator 1486 at least one peg 1550 may be inserted into at least one peg engagement recess 1552 and thereby limit the rotation of the second tubular dilator within the additional tubular dilator.

Figure 56:
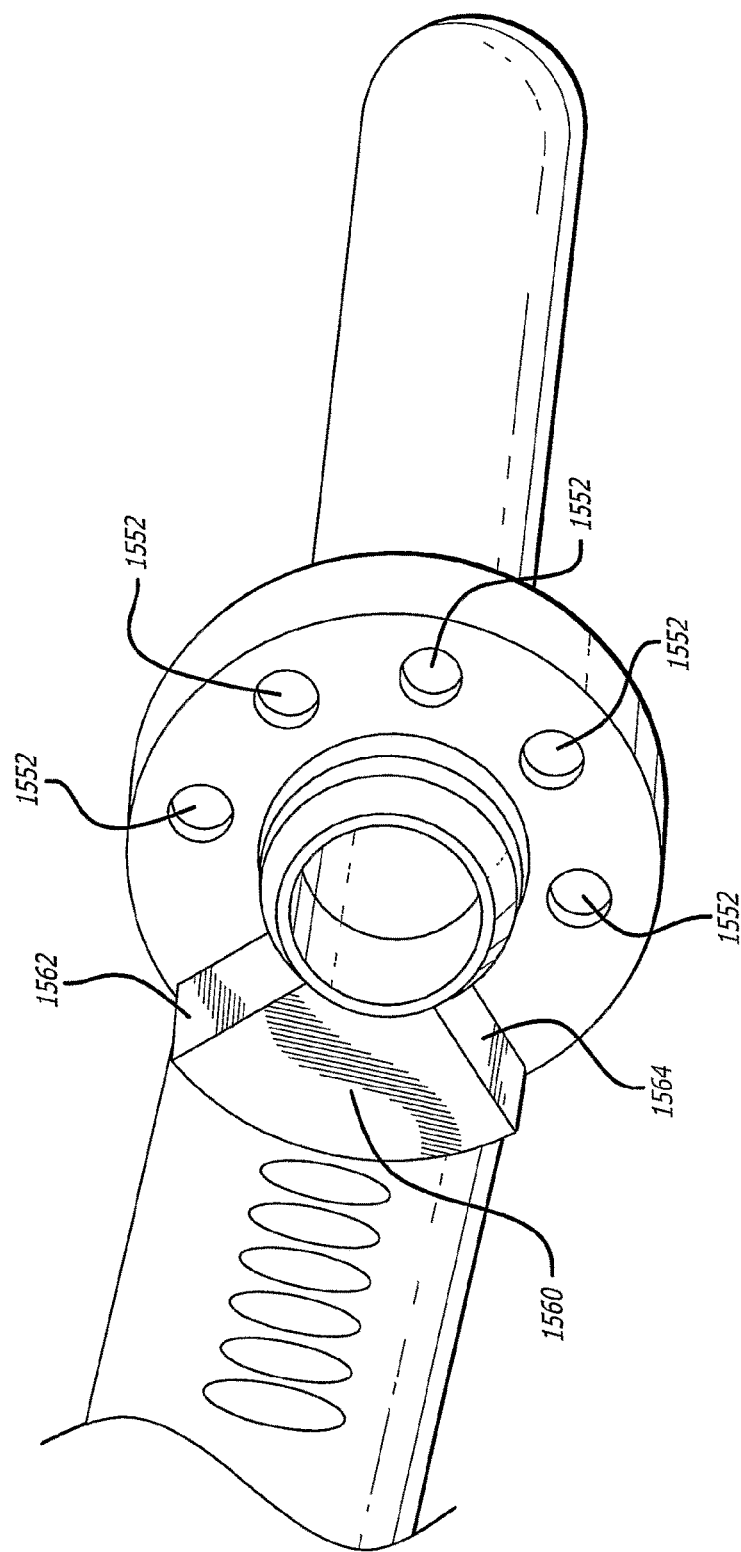
FIG. 56 is a perspective view of the proximal end of the third or additional dilation introducer in FIG. 50 showing the anti-rotation features in greater detail.
Figure 57:
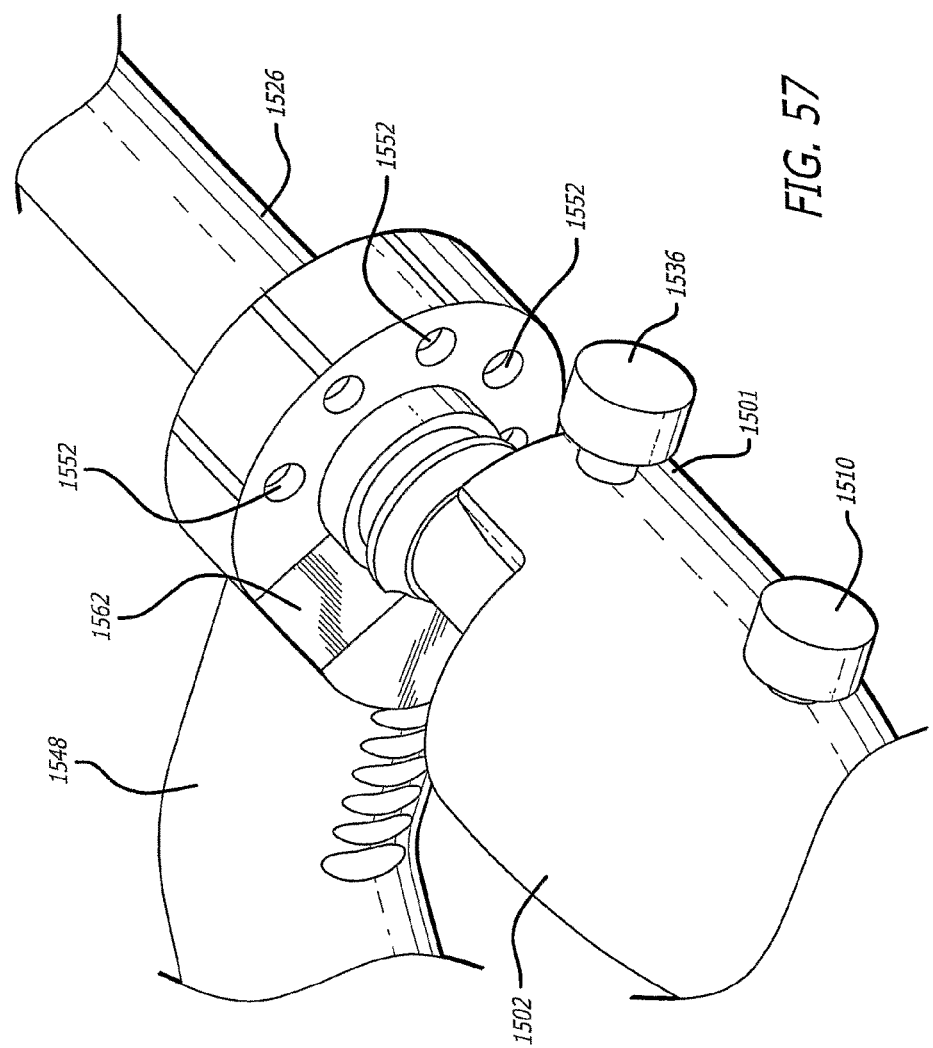
FIG. 57 is a perspective view of the dilation introducer in FIG. 50 showing the dilators in an un-locked position and showing the anti-rotation features in greater detail.
Figure 58:
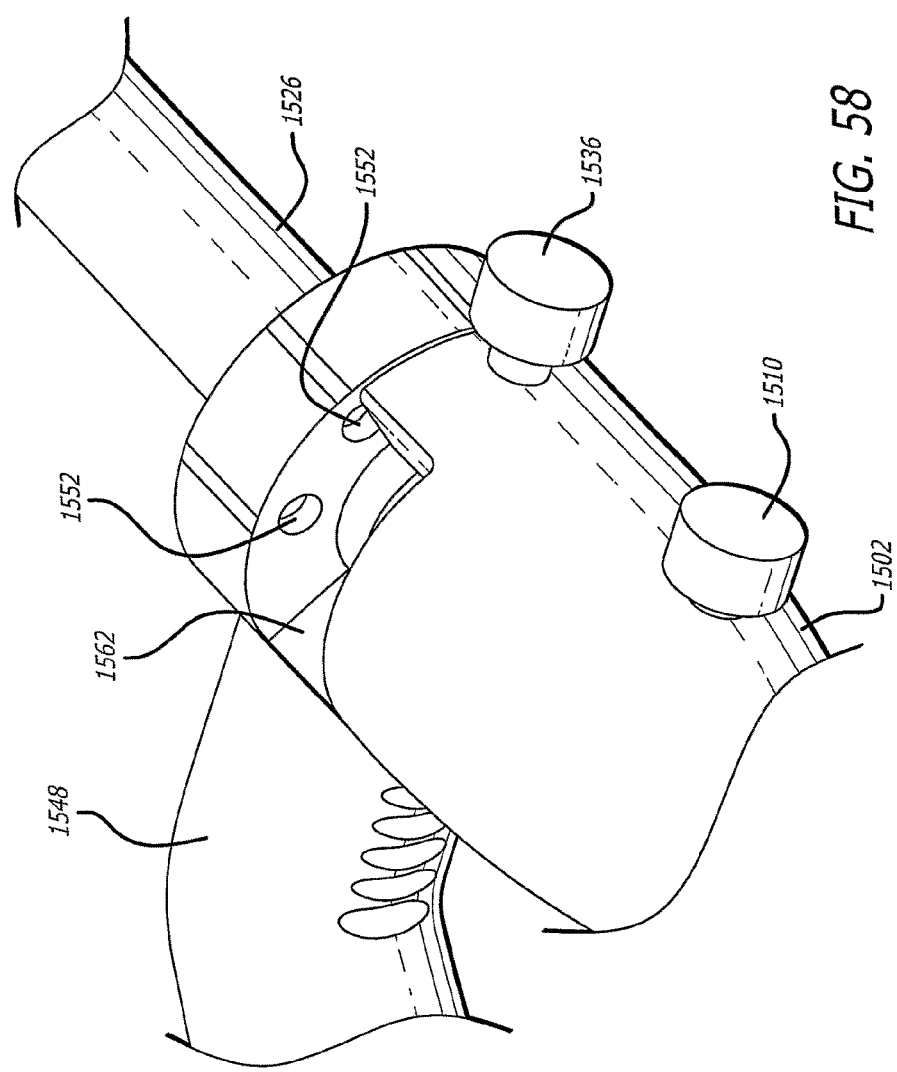
FIG. 58 is a perspective view of the dilation introducer in FIG. 50 showing the dilators in a locked position and showing the anti-rotation features in greater detail.

As shown in FIG. 56, in at least one embodiment, the additional tubular dilator 1486 further includes a rotation stop 1560. The rotation stop 1560 extends from the proximal side of the tubular head 1528 of the additional tubular dilator 1486. The rotation stop 1560 has a first rotation stop surface 1562 and a second rotation stop surface 1564. One of the side surfaces of the overhanging lip 1501 of the second tubular dilator 1484 will abut one of the rotation stop surfaces during extremes of rotation clockwise or counter-clockwise of the second tubular dilator 1484 within the additional tubular dilator 1486. The rotation stop 1560 thereby limits rotation of the second tubular dilator 1484 within the additional tubular dilator 1486. Furthermore, the degrees of allowable rotation of the second tubular dilator 1484 within the additional tubular dilator 1486 can be controlled by adjusting the relationship between the first rotation stop surface 1562 and the second rotation stop surface 1564 to a predetermined angle. For example, the angle between the first rotation stop surface 1562 and the second rotation stop surface 1564 may be set at approximately 90 degrees.

Figure 59:
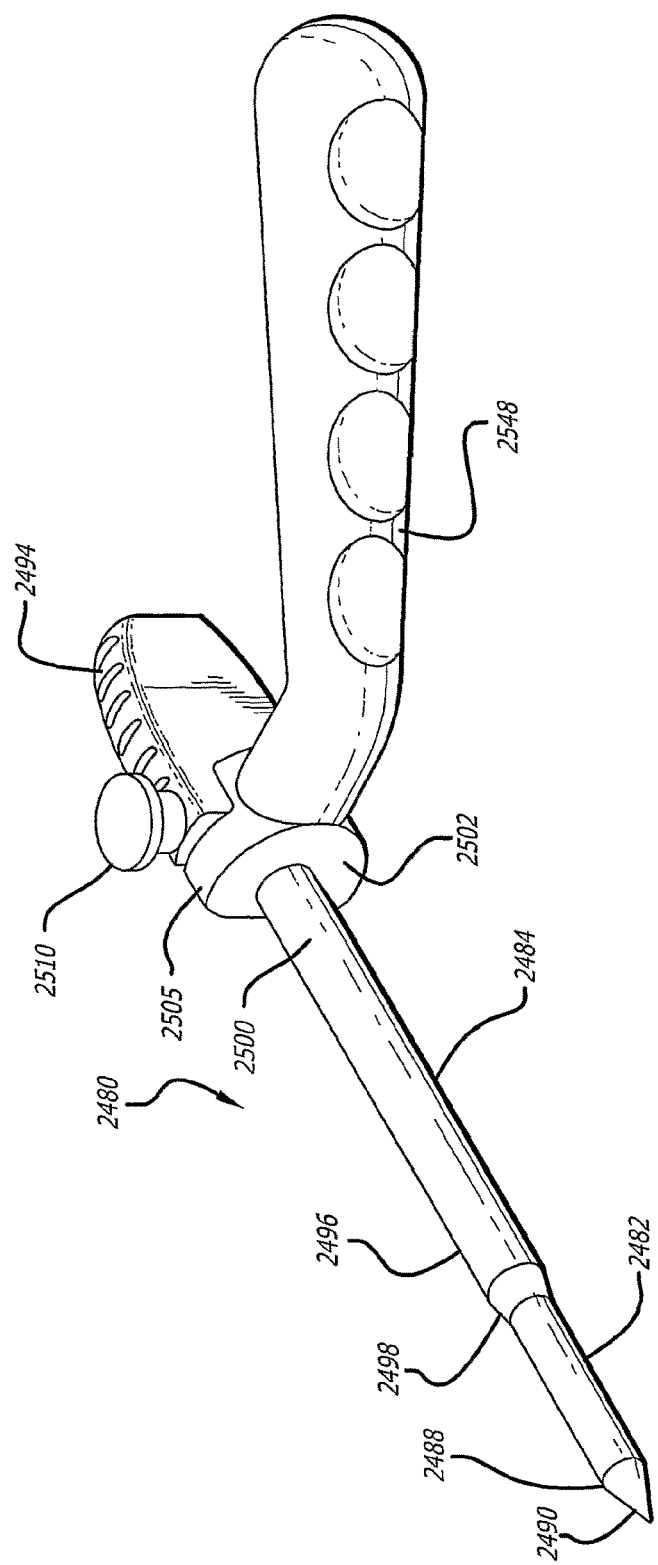
FIG. 59 is a perspective view of yet another embodiment of the dilation introducer having one latching button, a handle, and an anti-rotation feature showing the dilators in a locked position.

Yet another embodiment of the present systems is shown in FIGS. 59-65. One embodiment of the dilation introducer, generally designated as 2480, is shown in a locked assembled configuration in FIG. 59-61 and in an unlocked position in FIGS. 62-64. Referring to FIGS. 59-61, the dilation introducer includes a first or inner cylindrical dilator 2482, and at least one additional or second outer tubular dilator 2484. The first or inner cylindrical dilator 2482 and the second tubular dilator 2484 may be provided in various lengths, wherein either dilator is equal or longer or shorter in length than the others. The first or inner cylindrical dilator has a distal portion 2488 with a tapered tip 2490 which may also or alternatively be serrated, and a proximal portion 2492 including a slotted head member 2494. The slotted head member 2494 may be manufactured as one piece with the rest of the first inner dilator, or separately manufactured and thereafter assembled with the proximal portion 2492 of the inner dilator. In various embodiments, the first or inner cylindrical dilator 2482 may be cannulated, for example to allow passage of a guide wire down the central longitudinal axis of the first dilator, or alternatively, the first or inner cylindrical dilator may be without a lumen and uncannulated. If the first or inner cylindrical dilator 2482 is cannulated, then the slotted head member 2494 is also preferably cannulated. The central longitudinal axis of the cannula in the slotted head member 2494 is preferably aligned with the central longitudinal axis of the first dilator 2482 wherein a guide wire may be inserted through the slotted head member 2494 and out the tip 2490 of the first or inner cylindrical dilator 2482.

The second dilator tube 2484 has a distal end 2496 with a tapered tip 2498, that may also be serrated, a proximal end 2500 with a head member 2502, and an inner lumen 2504 with a distal opening 2506 and a proximal opening 2508. The head member 2502 of the second dilator tube 2484 includes a larger diameter distal portion 2505 and a smaller diameter substantially tubular proximal portion 2503. As shown also in FIG. 61-62, the smaller diameter substantially tubular proximal portion 2503 is sized to fit within the slot 2495 of the slotted head member 2494. There is a circumferentially oriented groove 2520 in the exterior of the smaller radius proximal portion 2503 for receiving a distal end 2518 of a first latching button 2510. As shown in FIG. 59, the latching button 2510 includes a cap located on the head of the pin. However, as discussed herein, the latching button can be produced as a unitary body having a head portion integrally formed therewith. The circumferentially oriented groove 2520 does not need to run completely around the smaller radius proximal portion 2503. The circumferentially oriented groove 2520 is preferably oriented in a generally perpendicular plane to the longitudinal axis of the second dilator tube 2484.

The first cylindrical dilator 2482 is removably received in the second tubular dilator 2484 for slidable telescoping movement within the second dilator tube. In one embodiment, the second dilator tube has a handle 2548 connected with the head member 2502 of the second dilator tube 2484. The handle 2548 may be a removal handle as described elsewhere herein.

Referring to FIGS. 59-64, the first and second dilators are connected together in a locked configuration with a latching button 2510 disposed in the head member 2494 of the first tubular dilator, and extending through an aperture 2512 in the head member 2494 of the first tubular dilator, whereby the latching button 2510 is moveable between a radially inward locking position (arrow 2514) and a radially outward unlocking position (arrow 2516). The distal end 2518 of the latching button 2510 is removably received in the groove 2520 of the smaller radius proximal portion 2503 of the head member 2502 of the second dilator, so as to engage and lock the first and second dilators together in the locking position. The latching button 2510 can be pulled radially outwardly to release the first dilator 2482, thereby allowing the first dilator 2482 to slide within the second tubular dilator 2484 to the unlocked collapsed configuration. Pulling the latching button 2510 radially outward also allows the first inner dilator 2482 to be removed from the second outer dilator 2484. The edges of the smaller radius proximal portion 2503 of the head member 2502 of the second dilator may be rounded to facilitate engagement with the slotted head member 2494 of the first dilator.

Figure 62:
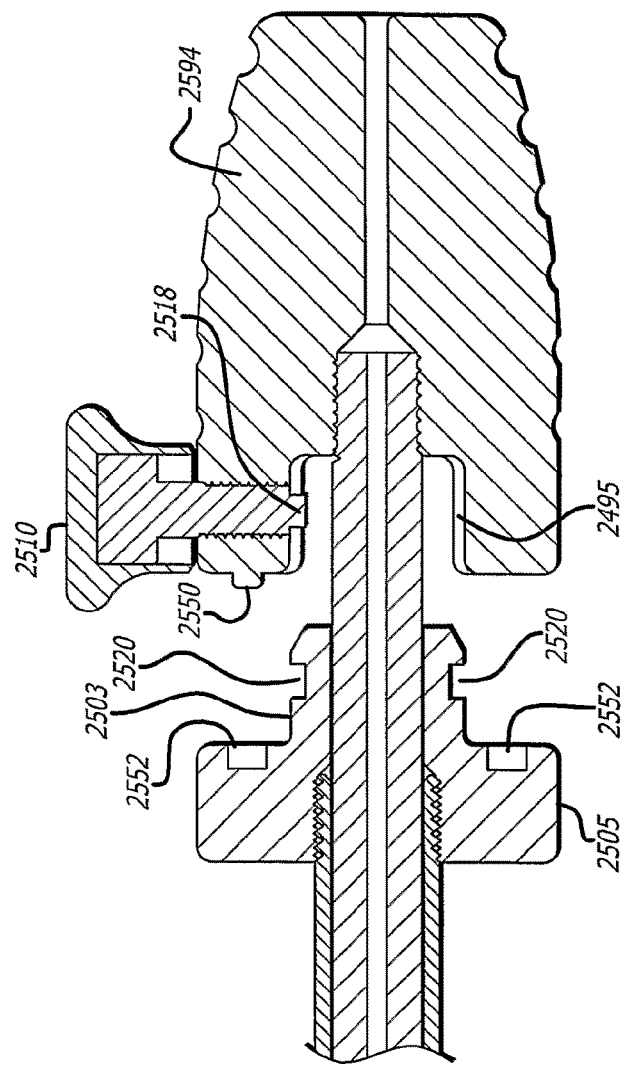
FIG. 62 is a magnified longitudinal cross sectional view through the latching and anti-rotation features of the dilation introducer in FIG. 59 shown in an un-locked configuration.
Figure 63:
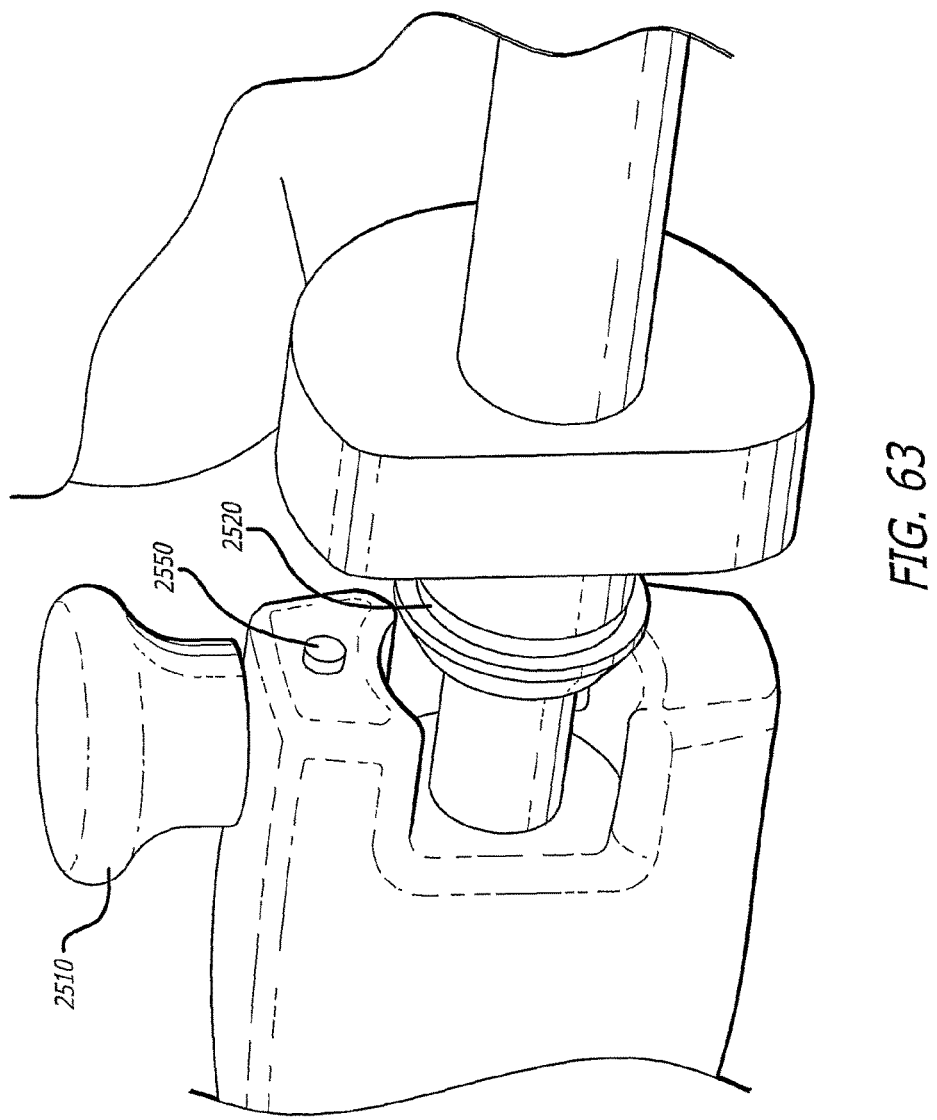
FIG. 63 is a distal perspective view through the latching and anti-rotation features of the dilation introducer in FIG. 59 shown in an un-locked configuration.
Figure 64:
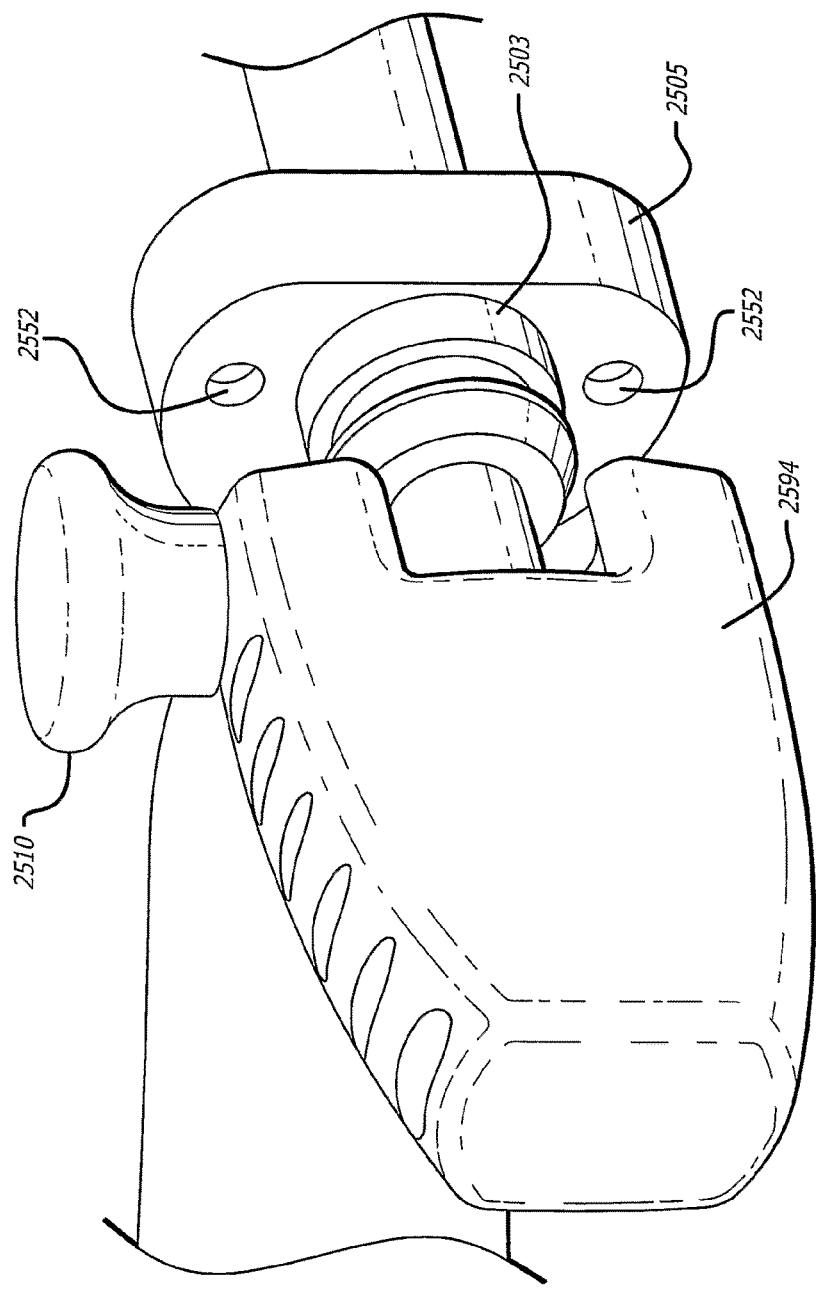
FIG. 64 is a proximal perspective view through the latching and anti-rotation features of the dilation introducer in FIG. 59 shown in an un-locked configuration.
Figure 65:
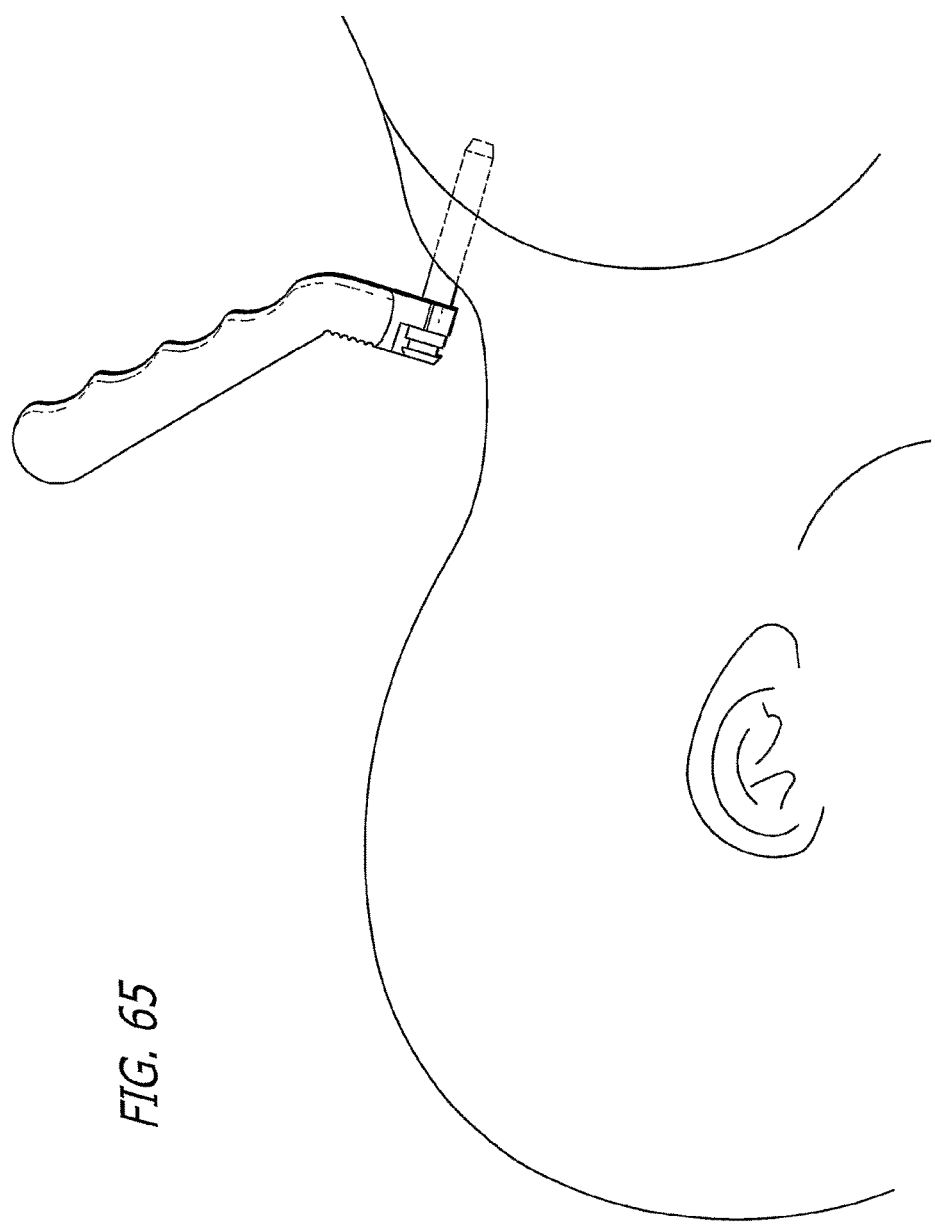
FIG. 65 illustrates the dilation introducer with removable handle of FIG. 59 showing positioning in a patient during surgery.

This embodiment may further include an anti-rotation feature. As shown in FIG. 62-64, the slotted head member 2494 of the first tubular dilator 2482 has at least one distally protruding peg 2550 and the proximal surface of the larger diameter portion 2505 of the head member 2502 of the second tubular dilator 2484 has at least one peg engagement recess 2552. When the second tubular dilator 2484 is locked to the first tubular dilator 2482. in at least one rotatory position, the peg 2550 will insert into a peg engagement recess 2552 and thereby limit the rotation of the outer or second tubular dilator around the inner first tubular dilator.

Figure 45:
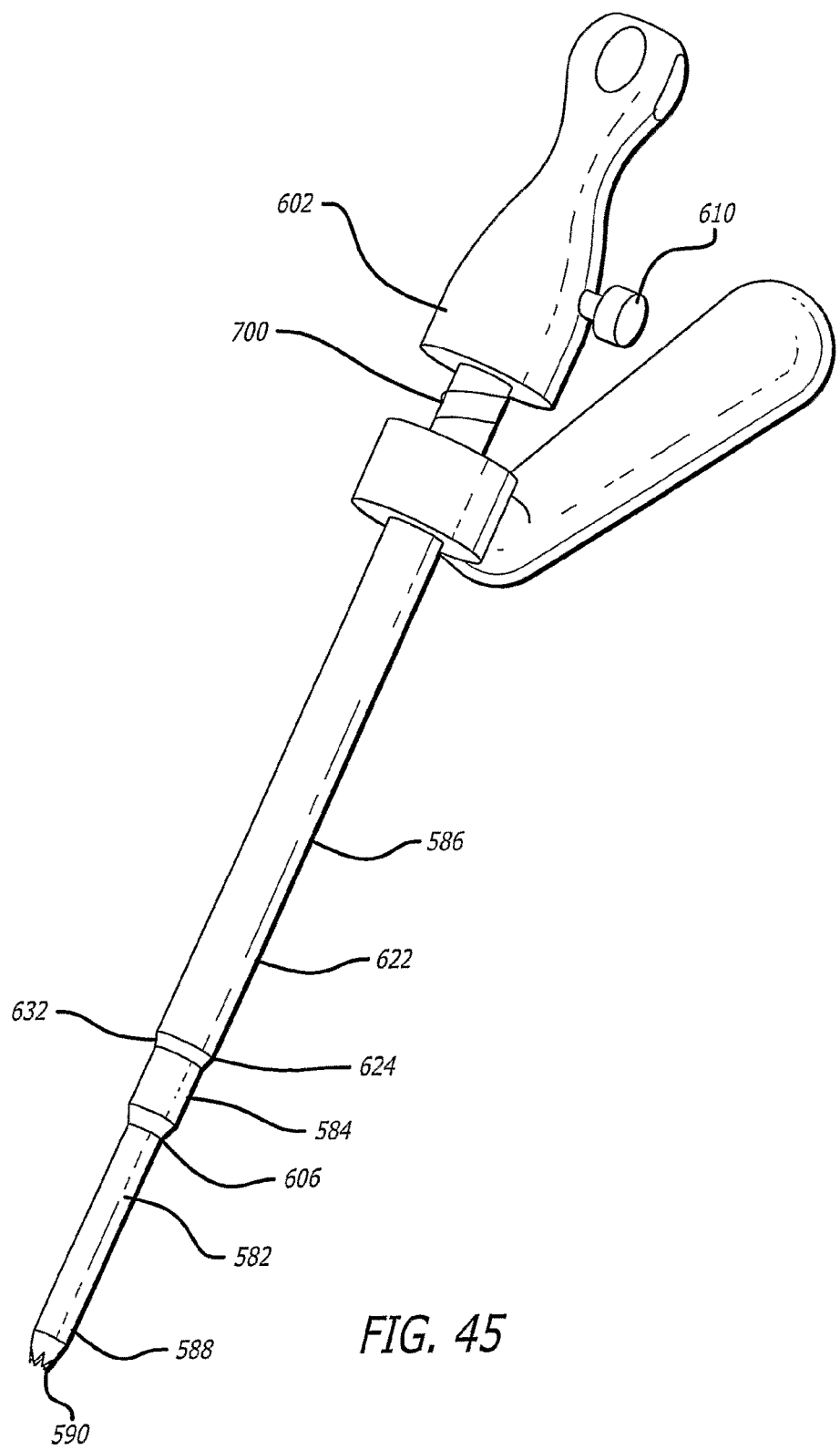
FIG. 45 is a perspective view of the embodiment of the dilation introducer of FIG. 44 in an unlocked configuration.
Figure 46:
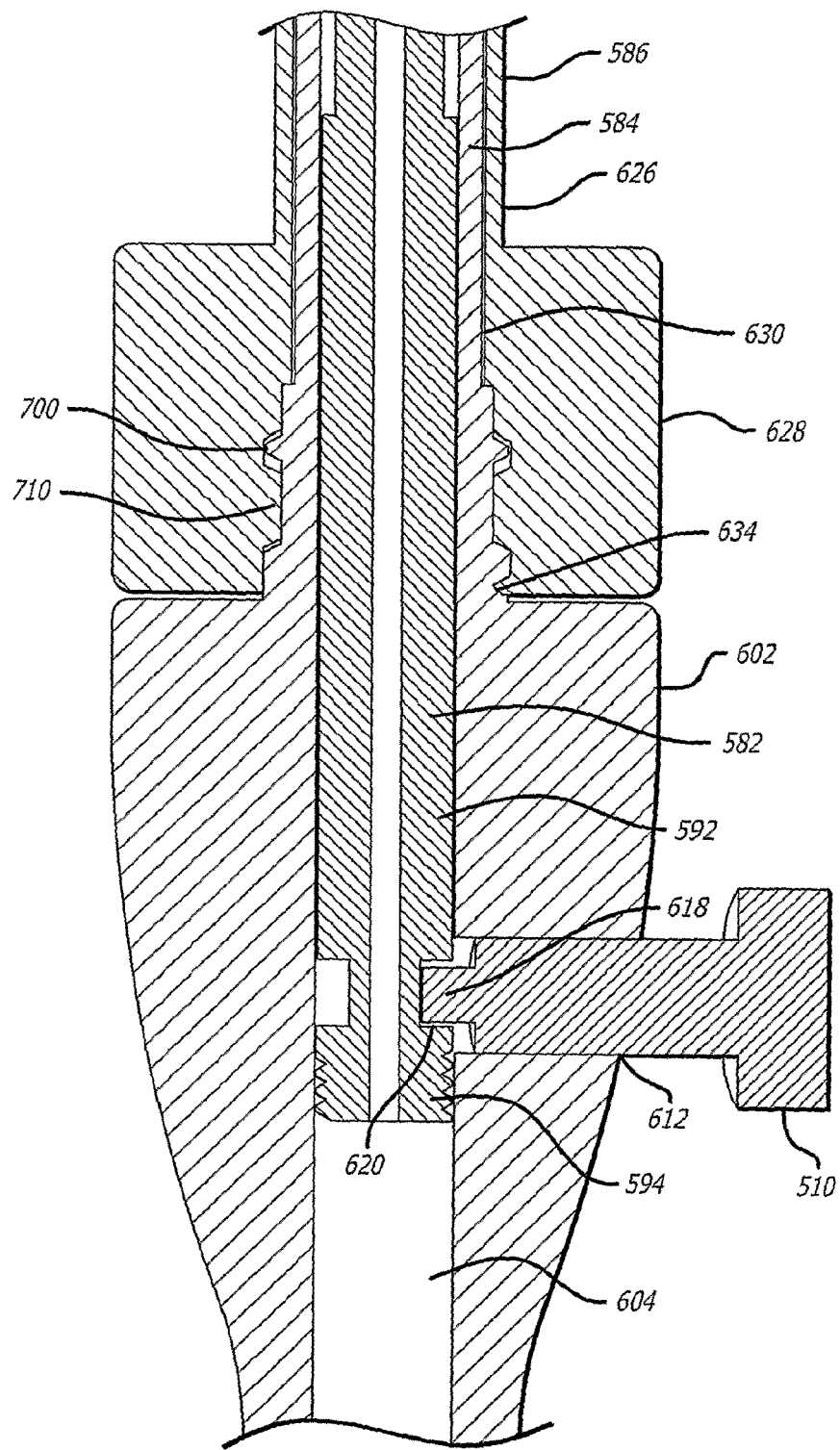
FIG. 46 is a cross sectional view of the embodiment of the dilation introducer of FIG. 44 showing the locking mechanism in detail.

With reference now to FIGS. 44-46, an additional embodiment of a dilation introducer 580 is shown in a locked assembled configuration in FIG. 44, and is shown in an unlocked, configuration in FIG. 45. Referring to FIGS. 44-45, the dilation introducer includes a first or inner cylindrical dilator 582, a second tubular dilator 584, and the additional tubular dilator 586. The first or inner cylindrical dilator, the second tubular dilator, and the additional tubular dilator may be provided in various lengths, wherein either dilator is equal or longer or shorter in length than the other. The first or inner cylindrical dilator has a distal portion 588 with a tip 590 which may be serrated and tapered or beveled, and a proximal portion 592 having a head portion 594. Alternatively, the head portion 594 can have an enlarged maximum cross-sectional area or diameter, such as by providing a threaded cap on the head portion, to prevent the dilation tube from falling out of the handle. The first or inner cylindrical dilator may be cannulated or uncannulated. In addition, as shown in FIG. 45, the first and second dilation tubes are locked together, and the combination of the first and second dilation tubes are unlocked from the third dilation tube.

The second tubular dilator 584 has a distal end 596 with a tip 598 that may be tapered or beveled, a proximal end 600 with a generally tubular head 602, and an inner lumen 604 with a distal opening 606 and a proximal opening 608. The first tubular dilator 582 is removably received in the second tubular dilator 584 for slidable telescoping movement within the second dilator tube. The first dilator 582 and second dilators 584 are connected together in a locked configuration with a latching button 610 disposed in the tubular head of the second tubular dilator 584 and extending through an aperture 612 in the tubular head of the second tubular dilator 584, so that the latching button is moveable between a radially inward locking position (arrow 614) and a radially outward unlocking position (arrow 616). The distal end 618 of the latching button is removably received in an aperture 620 of the first tubular dilator 582 in the locking position, so as to engage and lock the first and second dilators together. The latching button can thus be pulled radially outwardly to release the first and second dilators, to allow the first dilator to slide up into the second dilator in the unlocked collapsed configuration. The second dilator 584 further includes an externally threaded portion 700 on the proximal end 600 just distal to the generally tubular head 602.

Referring to FIGS. 44-46, the additional dilator tube 586 has a distal end 622 with a tapered or beveled tip 624, a proximal end 626 with a tubular head 628, and an inner lumen 630 with a distal opening 632 and a proximal opening 634. The tubular head 628 of the additional dilator tube further 586 includes an internally threaded portion 710. The internally threaded portion 710 of the additional dilator 586 is capable of engaging and locking with the externally threaded portion 700 of the second tubular dilator 584. The second tubular dilator 584 is thereby removably received in the additional tubular dilator 586 for slidable telescoping movement within the additional tubular dilator 586, and as shown in FIG. 45, the second tubular dilator 584 and the additional tubular dilator 586 also have an unlocked configuration in which the additional tubular dilator 586 is permitted to slidably telescope over the second tubular dilator 584 to dilate the patient's soft tissue at the distal end of the dilation introducer.

The second tubular dilator 584 and the additional tubular dilator 586 are connected together in a locked configuration by screwing the second tubular dilator 584 into the additional tubular dilator 586. The second tubular dilator 584 and the additional tubular dilator 586 are conveniently disconnected in an unlocked configuration by unscrewing the second dilator tube 584 from the additional tubular dilator 586. An advantage of this embodiment is that there are no latching buttons, clips, or other appendages on the additional tubular dilator 586 once it has been positioned. The remainder of the surgical procedure can therefore be carried out without hooking surgical sponges, sutures, or gloves, for example, on the outside of the dilator. While a particular combination of latching features and latching order has been described, other latching features and latching orders may be used for various specific applications.

In yet other embodiments, the tips of the tubular dilators are beveled instead of tapered. The beveled tips of the tubular dilators align to each other at a pre-determined angle for passage through the soft tissues. Beveled tips, as discussed above with the description of other embodiments, are advantageous when it is desirable or necessary for the long axis of the dilators to be at other than a perpendicular angle to the plane of the target bone surface. A beveled tip is useful when the trajectory to the bone target to be treated is at an angle to the plane of the skin at the entry site.

Figure 47:
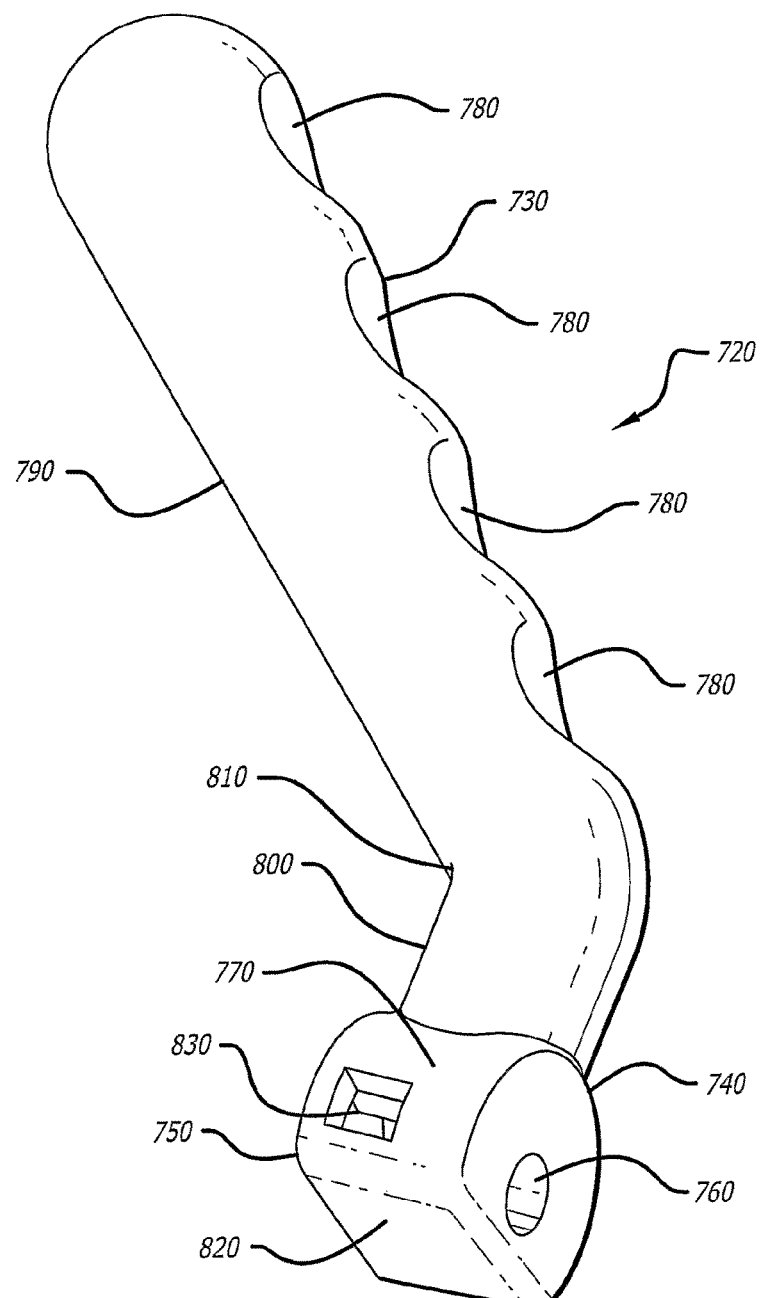
FIG. 47 is a perspective view of a handle for use with a dilation introducer.
Figure 48:
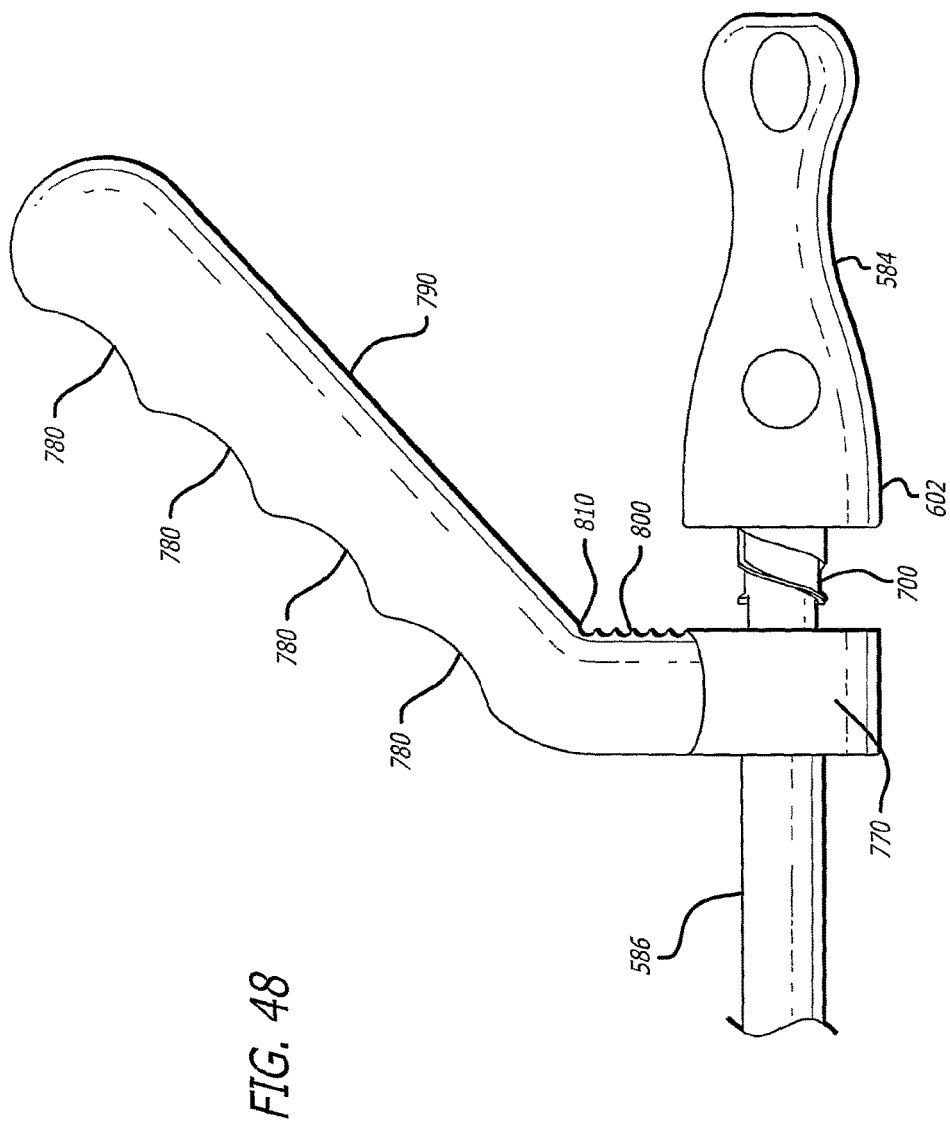
FIG. 48 is a perspective view of the handle of FIG. 47 being used with the dilation introducer embodiment of FIG. 44.
Figure 49:
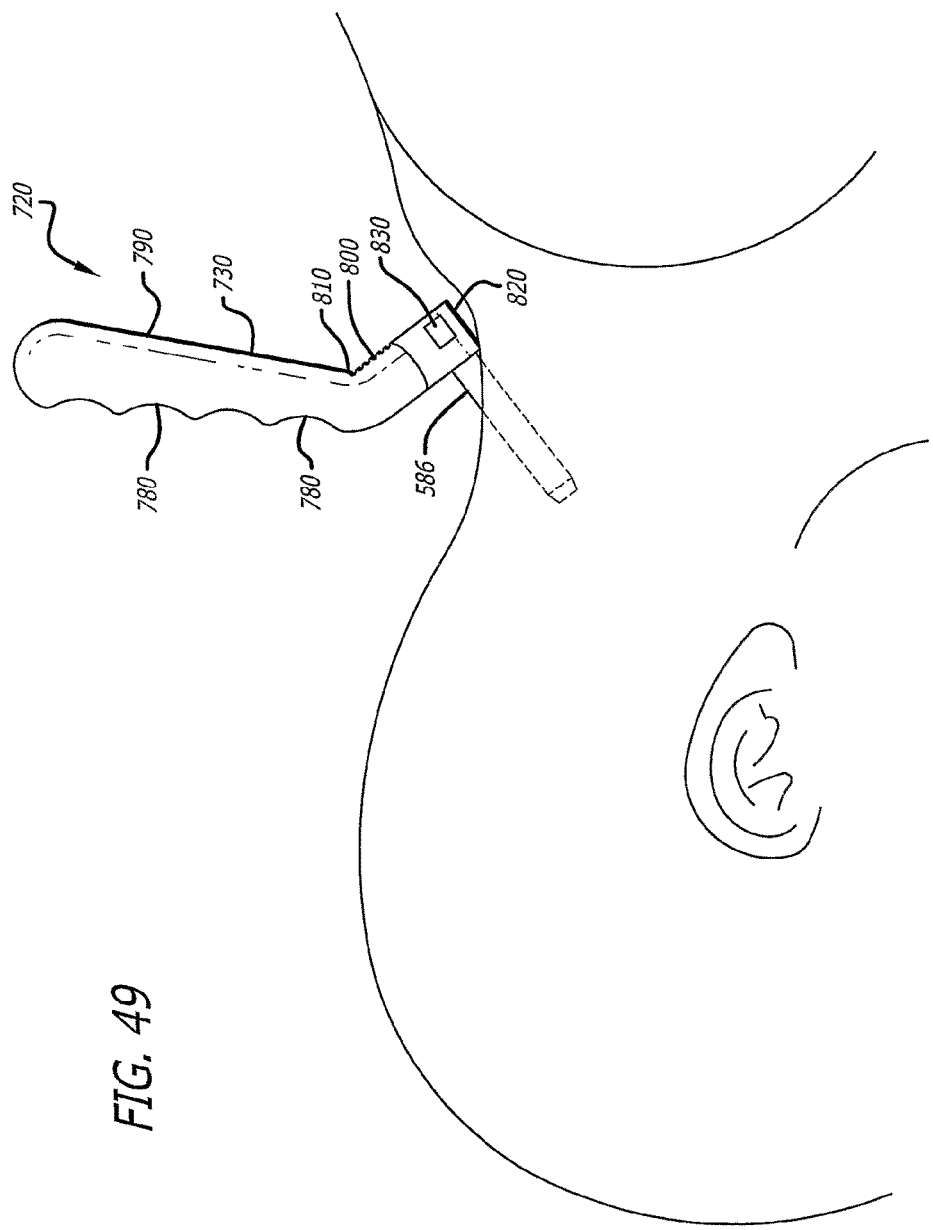
FIG. 49 shows the dilation introducer in FIG. 48 as it can be inserted into a patient on the operating room table.

In yet another embodiment of the invention shown in FIGS. 47-49, a handle 720 with at least one flat side 820 is provided. The flat side 820 makes the handle low profile and permits additional clearance with the patient's skin, thereby allowing sharper angulations when inserting the dilators into a surgical incision. The handle 720 in at least one embodiment is also removable.

A removable handle 720 includes a hand grip portion 730 and a tubular dilator engagement portion 740. The tubular dilator engagement portion 740 has a substantially cylindrical body 770 including a first opening 750 on one end and a second opening 760 on the opposite end. The first opening 750 is large enough to accept the tubular head 628 of the additional dilator tube 586. The substantially cylindrical body 770 snugly but releasably engages and holds the tubular head 628 of the additional dilator tube 586. The second opening 760 is smaller than the first opening 750, but large enough to permit externally threaded portion 700 of the second dilator to pass therethrough. The removable handle is secured to the dilation introducer by covering the tubular head 628 of the additional dilator tube 586 with the cylindrical body 770 of the handle 720, and screwing together the externally threaded portion 700 of the second dilator to the internally threaded portion 710 of the additional dilator tube, thereby locking the handle 720 between the generally tubular head 602 of the second dilator tube and the tubular head 628 of the additional dilator tube 586.

In this embodiment, the hand grip portion 730 of the removable handle 720 has finger indentations 780 on the side of the hand grip portion 730, to provide a more secure gripping surface for the surgeon. The hand grip portion 730 of the removable handle 720 has a proximal portion 790 and a distal portion 800. In various embodiments, the proximal portion 790 forms an angle 810 of between 90 degrees and 270 degrees with the distal portion 800.

The availability of handles that are removable and/or at different angles to the longitudinal axis of the additional dilator tube can be beneficial, for example, for use on obese patients and for giving the surgeon flexibility in inserting the dilation introducer and keeping the handle out of the way during the remainder of the surgical procedure. Furthermore, as shown in FIGS. 47 and 49, in at least one embodiment, the substantially cylindrical body 770 has the flat side 820 opposite the distal portion 800 of the hand grip portion 730. The flat side 820 gives additional clearance for the dilation introducer to enter the patient at a shallow angle to the skin. In the additional embodiment, the substantially cylindrical body 770 also has a window to accommodate passage of a latch pin, screw, or other locking device through the wall of the substantially cylindrical body 770. FIG. 48 shows details of a handle similar to that of FIG. 45. For example, this embodiment of FIG. 48 is illustrated without a flat surface, as shown in FIGS. 47 and 49.

Furthermore, various flexible retractor support arms that attach to the surgical table and to surgical retractors can be used to hold the dilator tubes in place during a surgical procedure. These flexible retractor arms known in the art typically are affixed to the operating table side rail. The other end of the flexible retractor arm may be attached by clamps or screws to a dilator tube directly, to a dilator tube handle, or to a bracket mounted on the outside of a dilating tube.

Referring to FIG. 66, in a variation of the outer dilator tube of the embodiment of FIGS. 32-33, the distal tip 3480 of an outer dilator tube 3482 may be angled or beveled, and may include a plurality of spikes 3484 to provide for increased traction of the tip of the outer dilator tube on bone tissue. The spikes may be formed of radiopaque material, such as gold, platinum, tantalum or the like, for use with fluoroscopy. As is illustrated in FIG. 67, a parallel guide 3486 disposed in the outer dilator tube has a distal tip 3488 that may optionally also be provided with a plurality of embedded spikes 3490 for increased traction on bone tissue. The spikes of the outer dilator tube and parallel guide may be formed with a rounded shape so as to deflect soft tissue during dilation, and to provide increased traction with bone upon completion of the insertion of the dilator.

Referring to FIGS. 68-71, an embodiment of a dilation introducer 3500, which is similar to the embodiment illustrated in FIGS. 8-12, and is shown in an unlocked configuration in FIG. 36. Referring to FIGS. 68-69, the dilation introducer includes a first or inner dilator tube 3502 having distal end (not shown) and a proximal end 3504 with a cylindrical head 3506. Means for removably connecting the first and second dilator tubes together in a locked configuration includes a first latching member 3508, having a shaft 3510 and a latching end 3512, such as a hook, projecting from the cylindrical head toward the distal end, and connected to a locking button 3514, which extends transversely out through a side aperture 3516 in the cylindrical head. The locking button includes a shaft 3518 and an enlarged head 3520 connected to the shaft, and the locking button is biased outwardly from the cylindrical head by a spring 3522. The latching member is received in an upper aperture 3524 of the adjacent cylindrical head of a second or intermediate dilator tube 3526, having a side opening latching chamber 3528 for retaining the latching end of the latching member when the locking button is biased outwardly by its spring, to lock the cylindrical heads of the first and second dilator tubes together. The cylindrical heads of the first and second dilator tubes can be unlocked and separated by manually depressing the locking button to move the latching member inwardly and the latching end of the latching member inwardly out of the side opening latching chamber. In all other aspects, the first dilator tube is essentially the same as the first dilator tube of the embodiment of FIGS. 8-12.

The second or intermediate dilator tube 3526 of the dilation introducer has a distal end (not shown) and a proximal end 3530 with a cylindrical head 3532. The means for removably connecting the second and third dilator tubes together in a locked configuration includes a second latching member 3534, having a shaft 3536 and a latching end 3538, such as a hook, projecting from the cylindrical head toward the distal end, and connected to a second locking button 3540, which extends transversely out through a side aperture 3542 in the cylindrical head. The locking button includes a shaft 3544 and an enlarged head 3546 connected to the shaft, and the locking button is biased outwardly from the cylindrical head by a spring 3548. The latching member is received in an upper aperture 3550 of the adjacent cylindrical head of a third or second intermediate dilator tube 3552, having a side opening latching chamber 3554 for retaining the latching end of the latching member when the locking button is biased outwardly by its spring, to lock the cylindrical heads of the second and third dilator tubes together. The cylindrical heads of the second and third dilator tubes can be unlocked and separated by manually depressing the second locking button to move the latching member inwardly and the latching end of the latching member inwardly out of the side opening latching chamber. In all other aspects, the second dilator tube is essentially the same as the second dilator tube of the embodiment of FIGS. 8-12.

The third, or second intermediate, dilator tube 3552 of the dilation introducer has a distal end (not shown) and a proximal end 3556 with a cylindrical head 3558. The means for removably connecting the third dilator tube and the outer dilator tube 3560 together in a locked configuration includes a third latching member 3562, having a shaft 3564 and a latching end 3566, such as a hook, projecting from the cylindrical head toward the distal end, and connected to a third locking button 3568, which extends transversely out through a side aperture 3570 in the cylindrical head. The third locking button includes a shaft 3572 and an enlarged head 3574 connected to the shaft, and the third locking button is biased outwardly from the cylindrical head by a spring 3576. The latching member is received in an upper aperture 3578 of the adjacent cylindrical head 3580 of the outer dilator tube, having a side opening latching chamber 3582 for retaining the latching end of the latching member when the locking button is biased outwardly by its spring, to lock the cylindrical heads of the third and outer dilator tubes together. The cylindrical heads of the third and outer dilator tubes can be unlocked and separated by manually depressing the third locking button to move the latching member inwardly and the latching end of the latching member inwardly out of the side opening latching chamber. In all other aspects, the third dilator tube is essentially the same as the second dilator tube of the embodiment of FIGS. 8-12.

Referring to FIG. 68, the outer dilator tube includes a distal end (not shown) and a proximal end 3584 to which a handle 3586 is connected at its cylindrical head end. The head end of the handle preferably includes a plurality of the upper apertures 3578 connected to corresponding side opening latching apertures 3582 for receiving the latching member of the adjacent dilator tube cylindrical head, as is illustrated in FIG. 72. Although three locking locations 3588 of the upper apertures and corresponding side opening latching apertures in the cylindrical head of the outer dilator tube are shown, more or fewer locking locations may be provided, and the locking locations may be provided at various positions, to aid in user flexibility as to which hand to use during the dilation procedure, as well as varying the position of the inner dilator tubes and optionally a parallel guide member during use or guide pin placement. In all other aspects, the outer dilator tube is essentially the same as the outer dilator tube of the embodiment of FIGS. 8-12.

Referring to FIGS. 70 and 71, in a variation of the embodiment shown, in FIGS. 68 and 69, the side opening latching chambers of the cylindrical heads of the dilator tubes may be closed so as to form covered latching chambers 3590a, b, c for the latching members. In all other aspects, the variation shown in FIGS. 70 and 71 is essentially the same as in FIGS. 68 and 69.

Referring to FIGS. 73-75, in another variation, an outer dilation tube 3600 may be provided with a light emitter 3602, such as one or more light emitting diodes (LEDs) or the end of a fiber optic, connected to or embedded in the tubular shaft 3604 of the outer dilation tube, and preferably near the distal end 3606 of the tubular shaft. As is illustrated in FIGS. 73 and 74, the light emitter may be an LED embedded in the wall 3608 of the tubular shaft, with the LED directed to illuminate the interior, exterior, or distal edge of the tubular shaft of the outer dilation tube. As is shown in FIG. 74, one or more elongated energy conducting members 3610, such as electrically conductive wires or fiber optics, for example, may be embedded in the tubular shaft, for conducting electricity or light to the light emitter. Referring to FIG. 73, the handle 3612 of the outer dilator tube preferably contains one or more batteries 3614 connected to a switch 3616 which is in turn connected to power the light emitter. The handle may be provided with a battery or batteries, which may be disposable, one or more switches, one or more resistors, and other associated electronics, so that the handle is disposable, or alternatively the handle may be provided with a connector for connection to an external power source. In one aspect, the switch is a thumb switch conveniently located on the handle adjacent to the cylindrical head 3618 of the outer dilation tube. The handle, cylindrical head, and tubular shaft of the outer dilation tube preferably includes one or more channels 3620 for the electrical wires connecting the one or more batteries to the switch and to the light emitter. When the light emitter includes one or more fiber optics, a light source 3622 such as one or more LEDs providing light to be conducted through the one or more fiber optics may be placed adjacent to the switch in the handle, with the one or more fiber optics extending through the wall of the tubular shaft of the outer dilator tube.

Referring to FIG. 75, in another variation of the dilation introducer of FIG. 73, the one or more elongated energy conducting members, such as one or more wires or one or more fiber optics, may be disposed on the outer surface of the tubular shaft of the outer dilation tube. In one aspect, the tubular shaft of the outer dilation tube may be formed with a groove 3620 running longitudinally on the exterior surface of the tubular shaft, parallel to the longitudinal axis of the outer dilation tube, to accommodate one or more wires or one or more fiber optics. Alternatively, the one or more elongated energy conducting members may be located on the inside of the dilator tube, or may extend through the wall of the dilator tube.

Referring to FIGS. 76-78, the present systems can include a telescoping expander sleeve 3630 that is adapted to be slidably disposed over the shaft of an outer dilator tube of any of the foregoing embodiments for expanding the patient's soft tissue down to the entry point on the bone tissue to be treated, while leaving the outer dilator tube in place, or allowing for replacement of the outer dilator tube with other equipment for treatment of the bone tissue. The tubular proximal portion may optionally be provided with a handle. The expander sleeve may be pre-assembled in combination with one or more of the dilation introducers, adapted to be ready for use. The telescoping expander sleeve has a first or inner generally tubular section 3632, having a tubular proximal portion 3634 with an enlarged proximal head 3636, and a distal portion 3638 with at least two substantially identical opposing active spreader arms 3640 (one of which is not visible in FIGS. 76-78) connected at one end to the tubular proximal portion and moveable radially at their distal tips 3642. The distal tips of the active spreader arms preferably have beveled edges 3644 to deflect soft tissue during insertion of the telescoping expander sleeve.

A second or outer generally tubular section 3646 is slidably disposed over the first or inner generally tubular section, and includes a tubular proximal portion 3648 and a distal portion 3650 with at least two substantial identical opposing passive spreader flaps 3652 interposed between the active spreader arms, hingedly connected to the tubular proximal portion at proximal ends 3654, and moveable radially at their distal tips 3656. The distal tips of the passive spreader flaps preferably also have beveled edges to deflect soft tissue during insertion of the telescoping expander sleeve. The distal tips of the passive spreader flaps when placed together in an unexpanded configuration have a generally circular configuration, so that the distal tips of two passive spreader flaps, for example, have a semi-circular configuration. The passive spreader flaps taper progressively toward their narrowed proximal ends connected to the tubular proximal portion of the outer tubular section. In one aspect, the passive spreader flaps are connected to the tubular proximal portion of the outer generally tubular section by rings 3656 passing through apertures 3658 and 3660 in the adjacent ends of the tubular proximal portion and the passive spreader flaps, respectively.

The active spreader arms are slidably interposed between and engage the passive spreader flaps, so that as the telescoping expander sleeve telescopes from an extended, unexpanded configuration to a collapsed, expanded configuration, as shown in FIG. 76, the active spreader arms slide from the narrow proximal ends of the passive spreader flaps to the wider distal ends of the passive spreader flaps to spread the distal ends of the passive spreader flaps apart, which also forces the distal ends of the active spreader arms apart, as shown in FIG. 78. In one aspect, the distal ends of the active spreader arms are slidably connected to slots 3662 extending along the inner edges 3664 of the passive spreader flaps by loops or rings 3666, such as loops of nylon filament or metal rings, for example, which pass through apertures 3668 in the distal ends of the active spreader arms. Telescoping of expander sleeve from a collapsed, expanded configuration to an extended, unexpanded configuration thus slides the distal ends of the active spreader arms of the inner tubular section from the wide distal ends of the passive spreader flaps along the inner edges of the passive spreader flaps to the narrowed proximal ends of the passive spreader flaps, to bring the passive spreader flaps together. The purpose of the active spreader arms and passive spreader flaps is to facilitate the creating of a larger working area adjacent to bone or bone tissues being treated. The spreader arms and flaps may optionally be covered by an expandable material, such as latex, for example, with a central through hole permitting operation of the device, to cover the spreader arms and flaps to prevent tissues from being pressed into cavities of the telescoping expander sleeve.

It should also be appreciated that one or more devices can be inserted through the same dilation introducer, and that the dilation introducer can be repositioned within the same incision for fixation of multiple devices. In addition, fiber optic devices may be inserted through or integrated with the dilation introducer for visual inspection of the target area. While particular locking features have been described for the different embodiments of the dilation introducer, any combination of locking features or alternate locking features may be utilized. The outer dilator tube may not be locked, and a handle on the outer dilator tube may simply be used as a stop. It should also be appreciated that while the invention has been described as being used in the context of orthopedic surgery, and more particularly for implantation of bone fixation devices, the dilation introducer of the invention can also be useful in dilation of soft tissue for percutaneous, minimally invasive surgical procedures such as nephrostomy, neurosurgery, heart valve repair or replacement, gastrointestinal surgery such as for gall bladder or gall stone surgery, hernia removal, transjugular intrahepatic portal-systemic shunt (TIPS) procedures for treatment of the liver, and the like.

The following surgical methods are described for purpose of illustration and by way of example and are not meant to be limiting. Modified methods for utilizing the dilation introducer for spinal surgery, hip surgery, other orthopedic surgery, and other surgical procedures will be evident to those skilled in the art, without departing from the spirit and scope of the invention.

A generally applicable surgical method for progressive soft tissue dilation from a skin entry point to a deep surgical target can start with a clinician identifying a skin entry point, a deep target, and a desirable trajectory between the skin entry point and the deep target. The deep target may be, for example a bony landmark or other anatomic structure to be treated. A skin incision can be made at this time, or alternatively after the insertion of a guide wire. A dilation introducer with a cannulated first or inner dilator for passage of a guide wire is utilized, and the guide wire is first passed through the soft tissues from the skin entry point to the deep surgical target, preferably with intraoperative imaging performed to guide safe and accurate placement. The skin incision can be lengthened to be at least equal to the outer diameter of the outermost dilator tube to be used for the surgical procedure. An incision can be made in the fascia, at least equal to the outer diameter of the outermost dilator tube to be used for the surgical procedure. The first or inner dilator is inserted over the guide wire, preferably with the dilation introducer in a locked configuration, and the tip of the first dilator is passed to the deep surgical target. The guide wire may be removed at this step or later in the procedure if desired by the clinician. The first dilator is unlocked from at least the second dilator tube, and the second dilator tube is distally passed over the first dilator towards the deep surgical target. An additional dilator tube, such as a third dilator tube, is then unlocked from at least the second dilator tube, and the additional dilator tube is passed over the second dilator tube towards the deep target. Preferably, correct positioning of the dilator tubes is confirmed again by intraoperative imaging, for example fluoroscopy or intraoperative X-Ray. The first and second dilator tubes are then removed, leaving only the outermost dilator tube in place. After the surgical procedure has been completed, the outermost dilator tube is removed and the fascia and skin closed in the usual fashion.

In another embodiment, a non-cannulated first or inner dilator is used. The method starts with the clinician identifying a skin entry point, a deep target, and a desirable trajectory between the skin entry point and the deep target. The deep target may be, for example a bony landmark or other anatomic structure to be treated. An incision is made in the skin and in the fascia, at least equal in length to the outer diameter of the outermost dilator tube to be used for the surgical procedure. The non-cannulated first or inner dilator is passed, preferably with intraoperative image guidance, towards the deep target. The first dilator is unlocked from at least the second dilator tube, and the second dilator tube is passed over the first dilator toward the deep surgical target. The additional dilator tube is then unlocked from the second dilator tube, and the additional dilator tube is passed over the second dilator tube toward the deep target. Preferably, correct positioning is confirmed again by intraoperative imaging, for example fluoroscopy or intraoperative X-Ray. The first and second dilator tubes are then removed, as well as any additional dilator tubes, leaving only the outermost dilator tube in place. After the surgical procedure has been performed, the outermost dilator tube is removed and the fascia and skin closed in the usual fashion.

Figure 24:
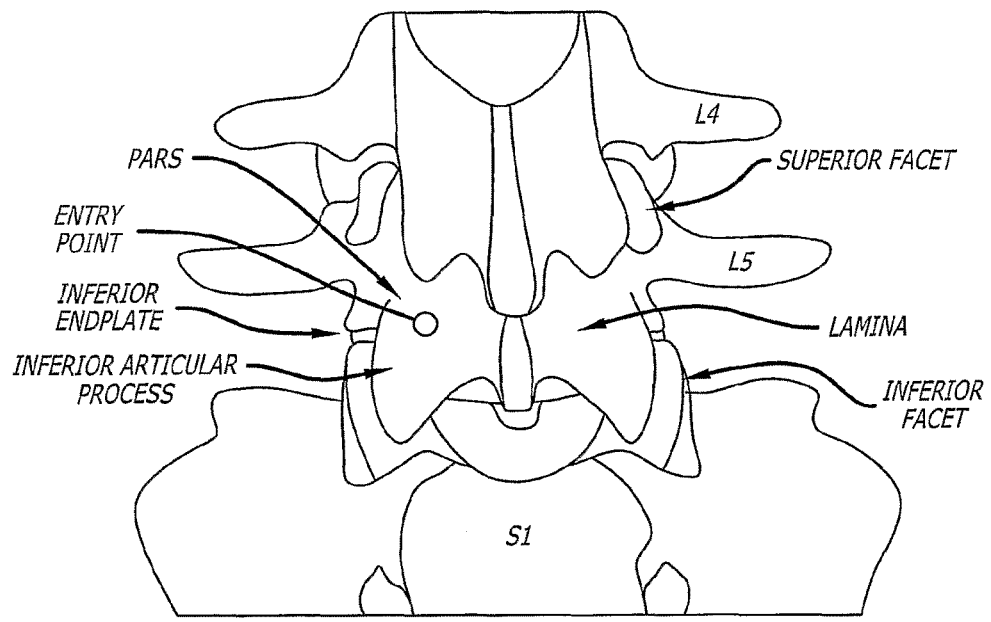
FIG. 24 is a schematic diagram illustrating location of a starting point for insertion of a bone fixation device according to the method of the invention.
Figure 25:
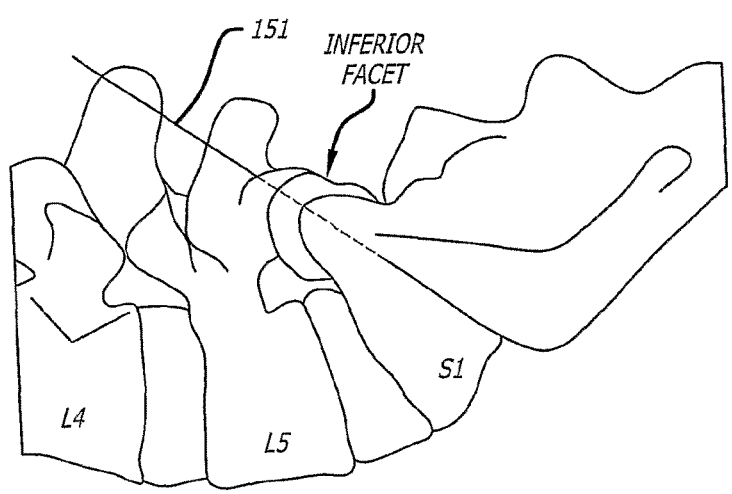
FIG. 25 is a schematic diagram of a lateral view illustrating location of a trajectory for insertion of a bone fixation device according to the method of the invention.
Figure 26:
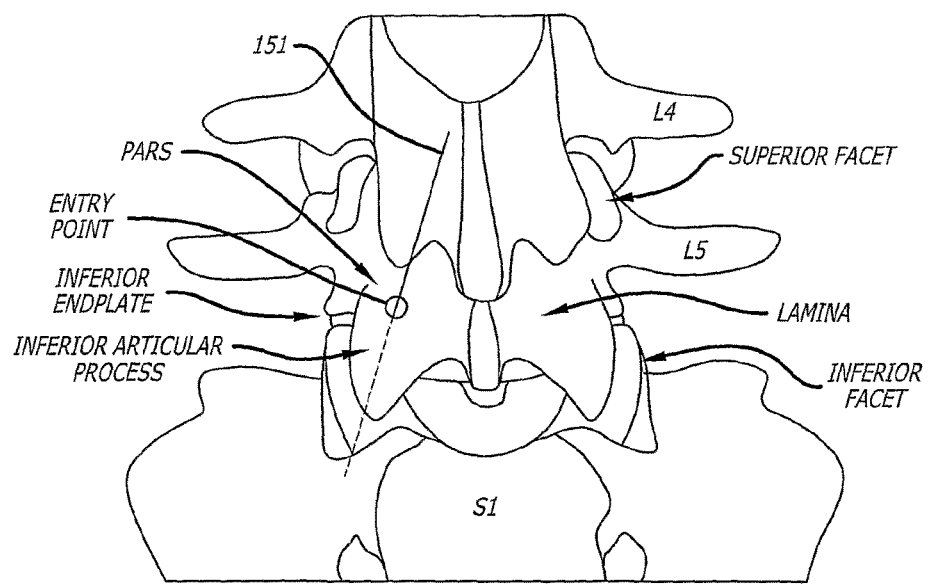
FIG. 26 is a schematic diagram of an anterior view illustrating location of a trajectory for insertion of a bone fixation device according to the method of the invention.

Referring to FIGS. 24-26, a surgical method for spinal instrumentation, such as spinal fusion, utilizing the dilation introducer apparatus and a bone fixation device such as a bone fixation device available under the trade name BONE-LOK from Triage Medical, Inc. of Irvine, Calif., is described. In addition, the present systems can be used with one or more of the bone fixation devices disclosed in U.S. Pat. Nos. 6,685,706; 6,648,890; 6,632,224; 6,511,481; and 6,348,053, and U.S. Pat. Pub. Nos. 20050033289; 20040260297; 20040260289; 20040199165; 20040199162; 20040181222; 20040138665; 20040127906; 20040106925; 20040010257; 20030097132; 20030069582; 20020143335; 20020143334; 20020143333; 20010049530; and 20010049529. Alternatively, other types of bone screws or fixation devices may also be suitable. The method of the invention involves dilating a patient's soft tissue down to bone tissue to be treated in orthopedic surgery, and entails an incision and fluoroscopy to locate an entry point on the bone tissue to be treated. The method described is by way of example and equally applicable to insertion of various pedicle screws into the spine.

Another method can comprise selecting an entry point into the bone, for example a facet joint. The target bone entry point and trajectory angle is then localized by intraoperative imaging, for example by fluoroscopy. A small incision is made in the skin, and the tip of a guide wire or K-wire 151 is, as shown in FIG. 25, is driven through the soft tissue of the patient at an advantageous angle down to the target. The skin incision is then lengthened, to approximately 17 mm for example. A similar incision is made in the fascia, using the guide wire as the midpoint of the incision. A first dilator tube of the dilation introducer is then passed over the guide wire until the tip of the dilation introducer reaches the target point on the bone. The guide wire is then driven into the facet and into the pedicle of the patient, with verification of the trajectory and depth by fluoroscopy. The second dilator tube of the dilation introducer is then released and passed over the first dilator tube to allow it to progress to the bone, allowing removal of the first dilator tube. This is repeated for the remaining, progressively wider telescoping dilator tubes, to progressively expand the patient's soft tissue down to the entry point on the bone tissue to be treated, and leaving an outer dilator tube in place. A depth gauge may then be used to verify that the appropriate depth has been reached. In some embodiments, the first dilator tube is preferably removed together with the second dilator tube, all at once.

In this embodiment, a pre-drill can thereafter be advanced to the desired location, which is then also verified by fluoroscopy. A cortex drill can be advanced until its positive stop engages, and the distal tip of a tap is driven into the bone until it reaches the appropriate depth, which is then also verified by fluoroscopy. The drill can be connected through an AO style quick connect, or a Jacobs chuck, as long as they are fully cannulated, to a ratcheting handle which is also preferably cannulated. A bone fixation device is then driven into the bone until it reaches the appropriate depth, which is then also verified by fluoroscopy. The bone fixation device is compressed to achieve appropriate stabilization, which is then also verified by fluoroscopy. Once compression of the bone fixation device has been achieved, the pull pin is removed, the guide wire is removed, and the remaining outer dilator tube is removed, and the incision can be closed normally.

In yet another embodiment the method further includes using a high speed drill to decorticate the facet and adjacent cortical bone, once the outer dilator tube is in place. A self tapping pedicle screw of appropriate diameter and length can then be advanced into the pedicle. The procedure is repeated for the adjacent spinal level and the pedicle screws are then connected to a rod or plate as well described in the art.

In yet another embodiment, the dilation introducer may be used for spinal microsurgery without using a guide wire. An incision is made through skin and fascia overlying the appropriate disc level as determined by intraoperative imaging, for example X-Ray or fluoroscopy. The first dilator tube is advanced through the paraspinal muscles, preferably under intraoperative image guidance such as flouroscopy, to the appropriate interlaminar space. The progressively larger diameter dilator tubes are advanced and the correct disc space is again confirmed. All of the dilator tubes are removed, except for the outermost dilator tube. Optionally, a microscope, surgical loupe eyewear, or other magnifying and/or illuminating aid is now brought into position. A routine microdiscectomy procedure is then performed, the dilation tube removed, and the wound closed in the usual fashion.

In still another embodiment, a patient with a spinal instability may be positioned face down on an operating table. A trocar may then be inserted through a tissue tract and advanced to a first vertebral body. A guide wire may then be advanced through the trocar and into the first vertebral body. The guide wire is preferably inserted into the pedicle of the vertebral body, through the pars (the region between the lamina and inferior articular processes). The dilation introducer of the present invention may be inserted over the guide wire and utilized to enlarge the tissue tract. A surgical sheath may then be advanced over the outer dilator tube left in place for further procedures. A drill may be advanced over the guide wire and through the sheath to drill an opening in the vertebral body for insertion of a bone stabilization device, or the step of drilling may omitted when a self-tapping or self-drilling bone stabilization device is to be applied. The body of the bone fixation or stabilization device may then be advanced over the guide wire through the outer dilator tube and surgical sheath until it engages the vertebral body, after which an insertion tool may be used to place the bone fixation or stabilization device as needed, after which the surgical site may be closed and dressed. This procedure can be done with or without compression, and is performed bilaterally. This procedure can be understood to be a dynamic stabilization procedure that uses an extension limiting device.

In a further embodiment, the present systems can be used effectively in hip surgeries. One example of a method using the present systems in a hip surgery can be practiced as follows. A physician can determine a trajectory and location for an initial guide pin. A small incision (e.g., a small stab incision) can be made in the skin. A guide pin can be placed into a bone of the hip at the desired trajectory and location for the tissue dilation system. In certain situations, the guide pin can be inserted into the a bone of the hip. A second incision can then be made through the skin and fascia. In certain situations, the second incision may have a length of about 40 mm. One of the present tissue dilation systems, such as the systems illustrated in FIGS. 30-33, can be inserted through the second incision over the guide pin and up to the bone surface. More specifically, the first dilation tube of the tissue dilation system can be inserted so that the distal end of the first dilation tube contacts a surface of the hip bone. The positioning of the first dilation tube can be confirmed using fluoroscopy, or other conventional technique. The second dilator tube can then be released and advanced to further dilate the soft tissue near the first dilation tube. An imaging technique, such a fluoroscopy can then be used to confirm the desired placement. The third dilation tube can be released and advanced to further dilate the tissue near the second dilation tube. Placement of the third dilation tube can be confirmed using the imaging techniques described herein. A fourth dilation tube (e.g., the outermost dilation tube or the dilation tube with a handle extending therefrom) can then be released and advanced to further dilate the tissue near the third dilation tube. Placement can be confirmed with an imaging technique, such as fluoroscopy. A parallel guide wire insert can then be inserted through the fourth dilation tube with a hole of the guide wire insert receiving the guide pin. The guide wire insert can be locked into position by rotating the handle or the guide wire insert. Confirmation of the locked position can be achieved by aligning indicia or other markings on the handle and the guide wire insert. One or more additional guide pins can be placed into the bone, as desired. For example, the one or more additional guide pins can be placed through the holes of the guide wire insert. The center guide pin can be removed or left in place, as desired by the physician. The parallel guide wire insert can then be removed from the fourth dilation tube. The remaining guide pins can be advanced to a final position in the bone, if necessary. A bone fixation device or bone anchor, such as a BoneLok™ 7.3 mm HP device or conventional lag screws can then be inserted through the fourth dilation tube and used to fix a portion of the hip. The fourth dilation tube can then be removed from the patient, and the wound can be closed. The patient is allowed to recover as usual.

In view of the disclosure herein, various aspects of the present tissue dilation systems can be summarized.

For example, it can be understood that the present systems involve telescoping dilation tubes, and that the systems can have an initial locked or substantially fixed assembled configuration for initial placement of the dilation introducer against a patient's tissue to be treated, and an, unlocked, collapsed configuration for dilating the patient's soft surrounding tissue to a desired degree of dilation to permit minimally invasive surgical procedures on the patient's tissue. As the telescoping dilation introducer is inserted, each individual dilator tube is successively released and advanced to progressively expand the patient's soft tissue down to the tissue to be treated. While there are many applications of the dilation introducer disclosed herein, the introducer is particularly applicable to fusion of bones in orthopedic surgery using minimally invasive techniques, or for providing access to hips in orthopedic surgery, and the like.

The present systems can be used in minimally invasive procedures utilizing the telescoping dilation introducer to insert a bone fixation device into a patient's spine for posterior spine fusion or into a hip, or other bone structure. While some posterior spine fusion procedures currently take up to two hours to complete, and requires a six inch incision, with the present systems and methods, comparable surgery can be completed in less than thirty minutes if desired, and/or can reduce the chance of damage to soft tissue by providing a dilation port having a diameter of 13 mm or less, if desired. However, procedures using the present systems may require more than thirty minutes to complete, and/or may form dilation ports having diameters greater than 13 mm. Similar and other benefits can be obtained with the present systems for different surgical procedures.

While the present invention is particularly useful for the purposes of orthopedic surgery, those skilled in the art will recognize that the invention can also be used for the treatment of a variety of internal organs or structures when it is desired to minimize the size of an opening in the patient's soft tissue and the resultant damage and trauma to tissue surrounding the operation site. By gentle successive dilation of a surgical incision using the dilation introducer, exposure of deep structures is obtained with little or no cutting or tearing of the soft tissue.

The present invention also relates to the use of the present tissue dilation systems in a medical or surgical procedure, for example procedures involving the spine and/or hip, and other orthopedic procedures. For example, an embodiment of the invention can be understood to be a telescopic percutaneous tissue dilation system, as described herein, for use as a medical or surgical device. Another embodiment can be understood to be the use of a first dilation tube, a second dilation tube, and a dilation tube retention assembly, as described herein, for the manufacture of a medical device, or surgical device, for dilating tissue in a patient. Yet another embodiment of the invention can be understood to be a combination of a first dilation tube, a second dilation tube, and a dilation tube retention assembly, as described herein, for use as a medical device, or a surgical device for dilating tissue in a patient. The present systems can comprise a plurality of tissue dilation tubes and/or devices, and one or more locking devices, one or more unlocking devices, and any combination thereof.

All references, articles, patents, applications and publications set forth above are incorporated herein by reference in their entireties.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A percutaneous telescopic tissue dilation system, comprising: a first dilation tube having a proximal end and a distal end; a second dilation tube having a proximal end, a distal end, and a lumen extending from the proximal end to the distal end, the lumen being dimensioned to accommodate at least a portion of the first dilation tube; a dilation tube retention assembly effective in retaining the second dilation tube in a substantially fixed position relative to the first dilation tube prior to dilation of tissue of an individual, and in releasing the second dilation tube from the substantially fixed position to facilitate movement of the second dilation tube towards the distal end of the first dilation tube to dilate tissue of a patient; and a third dilation tube having a lumen dimensioned to accommodate at least a portion of the second dilation tube, wherein the first dilation tube defines a lumen configured to receive a guide wire that is configured to guide the first dilation tube toward a target structure, and wherein the dilation tube retention assembly is effective in retaining the third dilation tube in a substantially fixed position relative to at least one of the first dilation tube and the second dilation tube, and wherein the dilation tube retention assembly includes at least one locking member that is configured to retain the second dilation tube in the substantially fixed position relative to the first dilation tube.

2. The system of claim 1, wherein the first dilation tube and the second dilation tube are preassembled in a locked configuration prior to dilation of the tissue of the patient.

3. The system of claim 1, wherein the dilation tube retention assembly comprises at least one locking clip removably connected to at least one of the first dilation tube and the second dilation tube.

4. The system of claim 1, wherein the dilation tube retention assembly comprises at least one locking pin engageable with at least one of the first dilation tube and the second dilation tube.

5. The system of claim 1, wherein the dilation tube retention assembly comprises at least one bayonet pin extending from an outer surface of at least one of the first dilation tube and the second dilation tube, and a corresponding number of bayonet pin receptacles provided on an interior surface of a dilation tube and rotatably engageable with the bayonet pins.

6. The system of claim 1, wherein the dilation tube retention assembly comprises a handle that effective in urging the dilation system from a locked configuration to an unlocked configuration.

7. The system of claim 1, further comprising the guide wire, wherein the guide wire extends from the distal end of the first dilation tube.

8. The system of claim 7, wherein the guide wire has a distal end having a maximal cross-sectional distance greater than a maximal cross-sectional distance of a region proximally located to the guide wire distal end.

9. The system of claim 1, further comprising a guide wire insert dimensioned to be inserted into the dilation tube having the largest lumen, the guide wire insert comprising a plurality of longitudinal bores effective in directing a plurality of guide wires parallel to each other from the tissue dilation system.

10. The system of claim 9, wherein the guide wire insert has a distal end configured to matingly engage with a bone surface of the patient.

11. The system of claim 10, wherein the guide wire insert has a beveled distal end.

12. The system of claim 9, wherein the guide wire insert comprises a locking device effective in retaining the guide wire insert in a locked configuration relative to the dilation tube in which it is placed.

13. The system of claim 1, further comprising an illumination source effective in illuminating a region in proximity to the distal end of the tissue dilation system.

14. The system of claim 1, further comprising an imaging system effective in imaging an area in proximity to the distal end of the tissue dilation system and transmitting the image to a remote location.

15. The system of claim 1, wherein the dilation tube retention assembly is further effective in retaining the third dilation tube in a substantially fixed position relative to one or both of the first dilation tube and the second dilation tube, and in releasing the third dilation tube from the one or both of the first dilation tube and the second dilation tube to facilitate movement of the third dilation tube towards the distal end of the one or both of the first dilation tube and the second dilation tube.

16. A method of producing a percutaneous telescopic tissue dilation system, comprising: inserting a first dilation tube into a lumen of a second dilation tube, wherein the first dilation tube has a lumen sized and configured to receive a guide wire; inserting the second dilation tube into a lumen of a third dilation tube; and engaging a dilation tube retention assembly with the first dilation tube and second dilation tube to maintain at least one of the first dilation tube and the second dilation tube in a substantially fixed position, wherein the dilation tube retention assembly is effective in retaining the third dilation tube in a substantially fixed position relative to at least one of the first dilation tube and the second dilation tube, wherein the dilation tube retention assembly includes at least one locking member that is configured to retain the second dilation tube in the substantially fixed position relative to the first dilation tube.

17. The method of claim 16, further comprising placing the combination of the first dilation tube and second dilation tube into a lumen of a third dilation tube.

18. The method of claim 17, wherein the third dilation tube comprises a handle extending from the third dilation tube.

19. A method of dilating tissue of a patient, comprising:
placing a telescopic tissue dilation system against a tissue region of a patient, the telescopic tissue dilation system comprising a first dilation tube located in a lumen of a second dilation tube, and a dilation tube retention assembly engageable with at least one of the first dilation tube and the second dilation tube;

advancing a guide wire into the patient towards a target structure;

advancing the first dilation tube over the guide wire and into the patient towards the target structure to provide dilation of the tissue around the first dilation tube;

releasing the second dilation tube from a substantially fixed position;

advancing the second dilation tube into the patient towards the target structure to provide greater dilation of the tissue compared to the dilation of the tissue around the first dilation tube; and advancing a third dilation tube into the patient towards the target structure over the second dilation tube.

20. The method of claim 19, wherein the final advancing step comprises advancing the third dilation tube over the second dilation tube into the patient towards the target structure.

21. The method of claim 20, wherein the method further comprises releasing the third dilation tube from a substantially fixed position before advancing the third dilation tube.

22. The method of claim 19, wherein the guide wire guide has a beveled distal end surface, and the method further comprises placing the beveled distal end surface against a bone surface so that the beveled distal end surface is flush with the bone surface.

23. The method of claim 19, further comprising a step of drilling bone contacted by the tissue dilation system.

24. The method of claim 19, further comprising illuminating the distal end region of one of the dilation tubes.

25. The method of claim 19, further comprising imaging an area in proximity to the distal end of the tissue dilation system.

26. The method of claim 19, wherein the advancing step comprises inserting the guide wire through one of a bore of a guide wire insert so as to direct the guide wire from the tissue dilation system.

27. The method of claim 19, further comprising the step of inserting the guide wire insert into the dilation tube having the largest lumen.

28. The method of claim 27, wherein the bore is one of a plurality of longitudinal bores effective in directing a plurality of guide wires parallel to each other from the tissue dilation system.

29. The method of claim 19, wherein the retention assembly is further engageable with the third dilation tube and one or both of the first and second dilation tubes so as to retain the third dilation tube in a substantially fixed position relative to one or both of the first and second dilation tubes.

30. The method of claim 19, wherein the dilated tissue provides an access path to the spine.

* * * * *